(12) United States Patent
Rosen et al.

(10) Patent No.: US 9,867,693 B2
(45) Date of Patent: Jan. 16, 2018

(54) INTRAOCULAR LENS THAT IMPROVES OVERALL VISION WHERE THERE IS A LOCAL LOSS OF RETINAL FUNCTION

(71) Applicant: AMO Groningen B.V., Groningen (NL)

(72) Inventors: Robert Rosen, Groningen (NL); Hendrik A Weeber, Groningen (NL); Carmen Canovas Vidal, Groningen (NL); Marrie Van Der Mooren, Engelbert (NL); Dora Sellitri, Groningen (NL)

(73) Assignee: AMO Groningen B.V., Groningen (NL)

( * ) Notice: Subject to any disclaimer, the term of this patent is extended or adjusted under 35 U.S.C. 154(b) by 0 days.

(21) Appl. No.: 14/644,082

(22) Filed: Mar. 10, 2015

(65) Prior Publication Data

US 2015/0250583 A1    Sep. 10, 2015

Related U.S. Application Data

(60) Provisional application No. 61/950,757, filed on Mar. 10, 2014, provisional application No. 61/987,647, filed on May 2, 2014.

(51) Int. Cl.
*A61F 2/16* (2006.01)
*A61B 3/14* (2006.01)
*A61B 3/028* (2006.01)

(52) U.S. Cl.
CPC .......... *A61F 2/1656* (2013.01); *A61B 3/028* (2013.01); *A61B 3/14* (2013.01); *A61F 2/1602* (2013.01);
(Continued)

(58) Field of Classification Search
CPC ........ A61F 2/16; A61F 2/1613; A61F 2/1637; A61F 2/164; A61F 2/1654; A61F 2/1656;
(Continued)

(56) References Cited

U.S. PATENT DOCUMENTS 3,367,734 A    2/1968    Bystricky et al.
4,581,031 A    4/1986    Koziol et al.
(Continued)

FOREIGN PATENT DOCUMENTS

EP    0343067 A1    11/1989
EP    0457553 A2    11/1991
(Continued)

OTHER PUBLICATIONS

International Search Report and Written Opinion for Application No. PCT/IB2015/000989, mailed on Sep. 8, 2015, 13 pages.
(Continued)

*Primary Examiner* — Paul Prebilic
(74) *Attorney, Agent, or Firm* — Abbott Medical Optics Inc.

(57) ABSTRACT

Systems and methods are provided for improving overall vision in patients suffering from a loss of vision in a portion of the retina (e.g., loss of central vision) by providing symmetric or asymmetric optic with aspheric surface which redirects and/or focuses light incident on the eye at oblique angles onto a peripheral retinal location. The intraocular lens can include a redirection element (e.g., a prism, a diffractive element, or an optical component with a decentered GRIN profile) configured to direct incident light along a deflected optical axis and to focus an image at a location on the peripheral retina. Optical properties of the intraocular lens can be configured to improve or reduce peripheral errors at the location on the peripheral retina. One or more surfaces of the intraocular lens can be a toric surface, a higher order aspheric surface, an aspheric Zernike surface or a Biconic Zernike surface.

10 Claims, 31 Drawing Sheets

(52) U.S. Cl.
CPC ............ *A61F 2/164* (2015.04); *A61F 2/1613* (2013.01); *A61F 2/1637* (2013.01); *A61F 2/1645* (2015.04); *A61F 2/1648* (2013.01); *A61F 2/1605* (2015.04); *A61F 2/1618* (2013.01); *A61F 2/1654* (2013.01); *A61F 2002/1681* (2013.01); *A61F 2240/002* (2013.01)

(58) Field of Classification Search
CPC ..... A61F 2250/0053; A61F 2250/0091; G02C 7/04; G02C 7/068; G02C 2202/20; G02C 2202/22
See application file for complete search history.

(56) References Cited

U.S. PATENT DOCUMENTS

| | | |
|---|---|---|
| 4,624,538 A | 11/1986 | MacFarlane |
| 4,637,697 A | 1/1987 | Freeman |
| 4,642,112 A | 2/1987 | Freeman |
| 4,648,878 A | 3/1987 | Kelman |
| 4,655,565 A | 4/1987 | Freeman |
| 4,666,446 A | 5/1987 | Koziol et al. |
| 4,778,462 A | 10/1988 | Grendahl |
| 4,795,462 A | 1/1989 | Grendahl |
| 4,798,608 A | 1/1989 | Grendahl |
| 4,798,609 A | 1/1989 | Grendahl |
| 4,828,558 A | 5/1989 | Kelman |
| 4,932,970 A | 6/1990 | Portney |
| 4,995,714 A | 2/1991 | Cohen |
| 4,995,715 A | 2/1991 | Cohen |
| 5,016,977 A | 5/1991 | Baude et al. |
| 5,056,908 A | 10/1991 | Cohen |
| 5,066,301 A | 11/1991 | Wiley |
| 5,089,023 A | 2/1992 | Swanson |
| 5,096,285 A | 3/1992 | Silberman |
| 5,114,220 A | 5/1992 | Baude et al. |
| 5,117,306 A | 5/1992 | Cohen |
| 5,120,120 A | 6/1992 | Cohen |
| 5,121,979 A | 6/1992 | Cohen |
| 5,121,980 A | 6/1992 | Cohen |
| 5,144,483 A | 9/1992 | Cohen |
| 5,225,858 A | 7/1993 | Portney |
| 5,229,797 A | 7/1993 | Futhey et al. |
| 5,354,334 A | 10/1994 | Fedorov et al. |
| 5,549,669 A | 8/1996 | Jansen |
| 5,652,638 A | 7/1997 | Roffman et al. |
| 5,683,457 A | 11/1997 | Gupta et al. |
| 5,699,142 A | 12/1997 | Lee et al. |
| 5,728,156 A | 3/1998 | Gupta et al. |
| 5,748,282 A | 5/1998 | Freeman |
| 5,760,871 A | 6/1998 | Kosoburd et al. |
| 5,777,719 A | 7/1998 | Williams et al. |
| 5,796,462 A | 8/1998 | Roffman et al. |
| 5,968,094 A | 10/1999 | Werblin et al. |
| 6,126,283 A | 10/2000 | Wen et al. |
| 6,126,286 A | 10/2000 | Portney |
| 6,142,625 A | 11/2000 | Sawano et al. |
| 6,183,084 B1 | 2/2001 | Chipman et al. |
| 6,197,057 B1 | 3/2001 | Peyman et al. |
| 6,210,005 B1 | 4/2001 | Portney |
| 6,338,559 B1 | 1/2002 | Williams et al. |
| 6,457,826 B1 | 10/2002 | Lett |
| 6,464,355 B1 | 10/2002 | Gil |
| 6,474,814 B1 | 11/2002 | Griffin |
| 6,488,708 B2 | 12/2002 | Sarfarazi |
| 6,491,721 B2 | 12/2002 | Freeman et al. |
| 6,527,389 B2 | 3/2003 | Portney |
| 6,533,416 B1 | 3/2003 | Fermigier et al. |
| 6,533,814 B1 | 3/2003 | Jansen |
| 6,536,899 B1 | 3/2003 | Fiala |
| 6,537,317 B1 | 3/2003 | Steinert et al. |
| 6,547,822 B1 | 4/2003 | Lang |
| 6,554,859 B1 | 4/2003 | Lang et al. |
| 6,557,992 B1 | 5/2003 | Dwyer et al. |
| 6,609,793 B2 | 8/2003 | Norrby et al. |
| 6,705,729 B2 | 3/2004 | Piers et al. |
| 6,808,262 B2 | 10/2004 | Chapoy et al. |
| 6,830,332 B2 | 12/2004 | Piers et al. |
| 6,846,326 B2 | 1/2005 | Zadno-Azizi et al. |
| 6,851,803 B2 | 2/2005 | Wooley et al. |
| 6,913,620 B2 | 7/2005 | Lipshitz |
| 6,923,539 B2 | 8/2005 | Simpson et al. |
| 6,923,540 B2 | 8/2005 | Ye et al. |
| 6,986,578 B2 | 1/2006 | Jones |
| 7,025,456 B2 | 4/2006 | Morris et al. |
| 7,025,460 B2 | 4/2006 | Smitth, III |
| 7,036,931 B2 | 5/2006 | Lindacher et al. |
| 7,048,760 B2 | 5/2006 | Cumming |
| 7,061,693 B2 | 6/2006 | Zalevsky |
| 7,073,906 B1 | 7/2006 | Portney |
| 7,137,702 B2 | 11/2006 | Piers et al. |
| 7,156,516 B2 | 1/2007 | Morris et al. |
| 7,186,266 B2 | 3/2007 | Peyman |
| 7,188,949 B2 | 3/2007 | Bandhauer et al. |
| 7,238,201 B2 | 7/2007 | Portney et al. |
| 7,287,852 B2 | 10/2007 | Fiala |
| 7,293,873 B2 | 11/2007 | Dai et al. |
| 7,365,917 B2 | 4/2008 | Zalevsky |
| 7,377,640 B2 | 5/2008 | Piers et al. |
| 7,410,500 B2 | 8/2008 | Claoue |
| 7,441,894 B2 | 10/2008 | Zhang et al. |
| 7,475,986 B2 | 1/2009 | Dai et al. |
| 7,503,655 B2 | 3/2009 | Smith, III |
| 7,615,073 B2 | 11/2009 | Deacon et al. |
| 7,665,842 B2 | 2/2010 | Ho et al. |
| 7,766,482 B2 | 8/2010 | Smith, III et al. |
| 7,871,162 B2 | 1/2011 | Weeber |
| 7,997,727 B2 | 8/2011 | Ho et al. |
| 8,057,034 B2 | 11/2011 | Ho et al. |
| 8,062,361 B2 | 11/2011 | Nguyen et al. |
| 8,201,943 B2 | 6/2012 | Hammer et al. |
| 8,206,442 B2 | 6/2012 | Sel et al. |
| 8,262,728 B2 | 9/2012 | Zhang et al. |
| 8,382,832 B2 | 2/2013 | Deacon et al. |
| 8,430,508 B2 | 4/2013 | Weeber |
| 8,540,365 B2 | 9/2013 | Varnas |
| 8,862,447 B2 | 10/2014 | Weeber |
| 9,345,570 B2 | 5/2016 | Sieber et al. |
| 2002/0044255 A1 | 4/2002 | Ye |
| 2002/0101564 A1 | 8/2002 | Herrick |
| 2002/0105617 A1 | 8/2002 | Norrby et al. |
| 2002/0118337 A1 | 8/2002 | Perrott et al. |
| 2002/0176049 A1* | 11/2002 | Sakai ..................... G02C 7/02 351/159.74 |
| 2003/0076478 A1 | 4/2003 | Cox |
| 2003/0171808 A1 | 9/2003 | Phillips |
| 2004/0021824 A1 | 2/2004 | Ye et al. |
| 2004/0085515 A1 | 5/2004 | Roffman et al. |
| 2004/0106992 A1 | 6/2004 | Lang et al. |
| 2004/0111153 A1 | 6/2004 | Woods et al. |
| 2004/0150789 A1 | 8/2004 | Jones |
| 2004/0156014 A1 | 8/2004 | Piers et al. |
| 2004/0230299 A1 | 11/2004 | Simpson et al. |
| 2005/0096226 A1 | 5/2005 | Stock et al. |
| 2005/0128432 A1 | 6/2005 | Altmann |
| 2005/0203619 A1 | 9/2005 | Altmann |
| 2005/0267575 A1 | 12/2005 | Nguyen et al. |
| 2006/0009816 A1 | 1/2006 | Fang et al. |
| 2006/0030938 A1 | 2/2006 | Altmann |
| 2006/0034003 A1 | 2/2006 | Zalevsky |
| 2006/0055883 A1 | 3/2006 | Morris et al. |
| 2006/0058874 A1 | 3/2006 | Peli |
| 2006/0066808 A1 | 3/2006 | Blum et al. |
| 2006/0098162 A1 | 5/2006 | Bandhauer et al. |
| 2006/0098163 A1 | 5/2006 | Bandhauer et al. |
| 2006/0109421 A1 | 5/2006 | Ye et al. |
| 2006/0116763 A1 | 6/2006 | Simpson |
| 2006/0116764 A1 | 6/2006 | Simpson |
| 2006/0116765 A1 | 6/2006 | Blake et al. |
| 2006/0158611 A1 | 7/2006 | Piers et al. |
| 2006/0176572 A1 | 8/2006 | Fiala |
| 2006/0238702 A1 | 10/2006 | Glick et al. |
| 2006/0244904 A1 | 11/2006 | Hong et al. |

(56) References Cited

U.S. PATENT DOCUMENTS

| | | | |
|---|---|---|---|
| 2006/0247766 A1 | 11/2006 | Marin | |
| 2007/0052920 A1 | 3/2007 | Stewart et al. | |
| 2007/0093891 A1 | 4/2007 | Tabernero et al. | |
| 2007/0129803 A1 | 6/2007 | Cumming et al. | |
| 2007/0171362 A1 | 7/2007 | Simpson et al. | |
| 2007/0182917 A1* | 8/2007 | Zhang | A61F 2/1654 351/159.11 |
| 2007/0182924 A1 | 8/2007 | Hong et al. | |
| 2007/0198083 A1 | 8/2007 | Sel et al. | |
| 2007/0268453 A1 | 11/2007 | Hong et al. | |
| 2008/0030677 A1 | 2/2008 | Simpson | |
| 2008/0161913 A1 | 7/2008 | Brady et al. | |
| 2008/0161914 A1 | 7/2008 | Brady et al. | |
| 2008/0269883 A1 | 10/2008 | Das et al. | |
| 2008/0269885 A1 | 10/2008 | Simpson et al. | |
| 2008/0269886 A1 | 10/2008 | Simpson et al. | |
| 2008/0269890 A1 | 10/2008 | Simpson et al. | |
| 2008/0312738 A1 | 12/2008 | Wanders | |
| 2009/0018652 A1 | 1/2009 | Hermans et al. | |
| 2009/0062911 A1 | 3/2009 | Bogaert | |
| 2009/0164008 A1 | 6/2009 | Hong et al. | |
| 2009/0187242 A1 | 7/2009 | Weeber et al. | |
| 2009/0198326 A1 | 8/2009 | Zhou et al. | |
| 2009/0204211 A1 | 8/2009 | Angelopoulos et al. | |
| 2009/0210054 A1 | 8/2009 | Weeber et al. | |
| 2009/0234448 A1 | 9/2009 | Weeber et al. | |
| 2009/0268155 A1 | 10/2009 | Weeber | |
| 2009/0268158 A1 | 10/2009 | Weeber | |
| 2009/0292354 A1 | 11/2009 | Gontijo et al. | |
| 2009/0295295 A1 | 12/2009 | Shannon et al. | |
| 2009/0323020 A1 | 12/2009 | Zhao et al. | |
| 2010/0016961 A1 | 1/2010 | Hong et al. | |
| 2010/0100177 A1 | 4/2010 | Zhao | |
| 2010/0100178 A1 | 4/2010 | Weeber et al. | |
| 2010/0157240 A1 | 6/2010 | Schmid et al. | |
| 2010/0161048 A1 | 6/2010 | Schaper, Jr. | |
| 2010/0188636 A1 | 7/2010 | Pinto et al. | |
| 2010/0286771 A1* | 11/2010 | Zhang | A61F 2/1654 623/6.3 |
| 2011/0149236 A1 | 6/2011 | Weeber | |
| 2011/0153014 A1 | 6/2011 | Zhang et al. | |
| 2011/0279912 A1 | 11/2011 | Fiala | |
| 2012/0277857 A1 | 11/2012 | Purchase et al. | |
| 2013/0013060 A1 | 1/2013 | Zadno-Azizi et al. | |
| 2013/0211515 A1 | 8/2013 | Blum et al. | |
| 2013/0226294 A1 | 8/2013 | Van Der Mooren et al. | |
| 2014/0022649 A1 | 1/2014 | Eckhardt | |
| 2014/0253877 A1* | 9/2014 | Li | A61F 2/1637 351/212 |
| 2015/0005877 A1* | 1/2015 | Wanders | A61F 2/1648 623/6.33 |
| 2015/0250583 A1 | 9/2015 | Rosen et al. | |
| 2015/0250585 A1 | 9/2015 | Rosen et al. | |
| 2015/0265399 A1 | 9/2015 | Rosen et al. | |
| 2015/0297342 A1 | 10/2015 | Rosen et al. | |
| 2015/0320547 A1 | 11/2015 | Rosen et al. | |
| 2016/0067037 A1 | 3/2016 | Rosen et al. | |
| 2016/0161364 A1 | 6/2016 | Alarcon et al. | |

FOREIGN PATENT DOCUMENTS

| | | |
|---|---|---|
| EP | 458508 A2 | 11/1991 |
| EP | 681198 A1 | 11/1995 |
| EP | 0926531 A1 | 6/1999 |
| EP | 949529 A2 | 10/1999 |
| EP | 1424049 A1 | 6/2004 |
| EP | 1818023 A1 | 8/2007 |
| EP | 1284687 B1 | 12/2007 |
| EP | 1310267 B1 | 1/2008 |
| EP | 1424049 B1 | 6/2009 |
| WO | 9222264 A1 | 12/1992 |
| WO | 9303409 A1 | 2/1993 |
| WO | 0019906 A1 | 4/2000 |
| WO | 0163344 A1 | 8/2001 |
| WO | 0182839 A1 | 11/2001 |
| WO | 0189424 A1 | 11/2001 |
| WO | 0221194 A2 | 3/2002 |
| WO | 03000154 A2 | 1/2003 |
| WO | 03009053 A1 | 1/2003 |
| WO | 03022137 A2 | 3/2003 |
| WO | 2004034129 A1 | 4/2004 |
| WO | 2004049979 A1 | 6/2004 |
| WO | 2004068214 A1 | 8/2004 |
| WO | 2004090611 A2 | 10/2004 |
| WO | 2004096014 A2 | 11/2004 |
| WO | 2005019906 A1 | 3/2005 |
| WO | 2006025726 A1 | 3/2006 |
| WO | 2006047698 A1 | 5/2006 |
| WO | 2006060477 A2 | 6/2006 |
| WO | 2006060480 A2 | 6/2006 |
| WO | 2007092948 A1 | 8/2007 |
| WO | 2007133384 A2 | 11/2007 |
| WO | 2008045847 A2 | 4/2008 |
| WO | 2008065362 A1 | 6/2008 |
| WO | 2009076670 A1 | 6/2009 |
| WO | 2009142961 A1 | 11/2009 |
| WO | 2012074742 A1 | 6/2012 |
| WO | 2012083143 A1 | 6/2012 |
| WO | 2013028992 A1 | 2/2013 |
| WO | 2013059041 A1 | 4/2013 |
| WO | 2013105855 A1 | 7/2013 |
| WO | 2013185855 A1 | 12/2013 |
| WO | 2015136375 A2 | 9/2015 |
| WO | 2015136380 A2 | 9/2015 |

OTHER PUBLICATIONS

International Search Report and Written Opinion for Application No. PCT/IB2015/001027, mailed on Sep. 8, 2015, 14 pages.

International Search Report and Written Opinion for Application No. PCT/IB2015/001244, mailed on Nov. 8, 2015, 14 pages.

International Search Report and Written Opinion for Application No. PCT/IB2015/002000, mailed on Feb. 12, 2016, 12 pages.

Diffractive Lenses for Extended Depth of Focus and Presbyopic Correction, Presentation from Wavefront Congress held on Feb. 15, 2008, Rochester, New York.

International Search Report and Written Opinion for Application No. PCT/IB2015/001588, mailed on Oct. 15, 2015, 11 pages.

International Search Report and Written Opinion for Application No. PCT/US2012/0523211, mailed on Dec. 21, 2012, 14 pages.

International Search Report and Written Opinion for Application No. PCT/US2014/020343, mailed on May 15, 2014, 10 pages.

Alfonso J.F., et al., "Prospective Study of the Acri.LISA Bifocal Intraocular Lens," Journal of Cataract Refractive Surgery, Nov. 2007, vol. 33 (11), pp. 1930-1935.

Atchison D.A., et al., "Shape of the Retinal Surface in Emmetropia and Myopia," Investigative Ophthalmology & Visual Science, Aug. 2005, vol. 46 (8), pp. 2698-2707.

Baskaran K., et al., "Benefit of Adaptive Optics Aberration Correction at Preferred Retinal Locus," Optometry and Vision Science, Sep. 2012, vol. 89 (9), pp. 1417-1423, (pp. 1 to 7).

Buralli D.A., et al, "Optical Performance of Holographic Kinoforms," Applied Optics, Mar. 1989, vol. 28 (5), pp. 976-983.

Canovas C., et al., "Hybrid Adaptive-Optics Visual Simulator," Optical Letters, Jan. 15, 2010, vol. 35 (2), pp. 196-198.

Cohen A.L., "Practical Design of a Bifocal Hologram Contact Lens or Intraocular Lens," Applied Optics, Jul. 1, 1992, vol. 31 (19), pp. 3750-3754.

Doskolovich L.L., et al., "Special Diffractive Lenses," Lens and Optical Systems Design, Apr. 1992, vol. 1780, pp. 393-402.

Escudero-Sanz I., et al., "Off-Axis Aberrations of a Wide-Angle Schematic Eye Model," Journal of the Optical Society of America. A, Optics, Image Science, and Vision, Aug. 1999, vol. 16 (8), pp. 1881-1891.

Hoffmann, P.C., et al., "Analysis of Biometry and Prevalence Data for Corneal Astigmatism in 23 239 Eyes," Journal of Cataract and Refractive Surgery, Sep. 2010, vol. 36(9), pp. 1479-1485.

Jaeken B., et al., "Comparison of the Optical Image Quality in the Periphery of Phakic and Pseudophakic Eyes," Investigative Oph-

(56) References Cited

OTHER PUBLICATIONS thalmology & Visual Science, May 1, 2013, vol. 54 (5), pp. 3594-3599.
Jafari-Nodoushan M., et al., "Control-Flow Checking Using Branch Instructions," IEEE/IFIP International Conference On Embedded and Ubiquitous Computing, Dec. 17-20, 2008, pp. 66-72.
Lewis P., et al., "Resolution of Static and Dynamic Stimuli in the Peripheral Visual Field," Vision Research, Aug. 15, 2011, vol. 51 (16), pp. 1829-1834.
Liou H.L., et al., "Anatomically Accurate, Finite Model Eye for Optical Modeling," Journal of Optical Society of America, Aug. 1997, vol. 14 (8), pp. 1684-1695.
Lundstroma L., et al., "Symmetries in Peripheral Ocular Aberrations," Journal of Modern Optics, Mar. 16, 2011, vol. 58 (19-20), pp. 1690-1695.
Marsack J.D., et al., "Metrics of Optical Quality Derived from Wave Aberrations Predict Visual Performance," Journal of Vision, Apr. 2004, vol. 4 (4), pp. 322-328.
Monsoriu J.A., et al., "Devil's Lenses," Optics Express, Oct. 17, 2007, vol. 15 (21), pp. 13858-13864.
Norrby S., et al., "Model Eyes for Evaluation of Intraocular Lenses," Applied Optics, Sep. 7, 2007, vol. 46 (26), pp. 6595-6605.
Oh N., et al., "Control-Flow Checking by Software Signatures," IEEE Transactions on Reliability, Mar. 2, 2002, vol. 51 (2), pp. 111-122.
Piers P.A., et al., "Eye Models for the Prediction of Contrast Vision in Patients with New Intraocular Lens Designs," Optics Letters, Apr. 1, 2004, vol. 29 (7), pp. 733-735.
Piers P.A., et al., "Theoretical Comparison of Aberration-Correcting Customized and Aspheric Intraocular Lenses," Journal of Refractive Surgery, Apr. 2007, vol. 23 (4), pp. 374-384.
Rosen R., et al., "Adaptive Optics for Peripheral Vision," Journal of Modern Optics, Jul. 10, 2012, vol. 59 (12), pp. 1064-1070.
Liou H.L., et al., "The Prediction of Spherical Aberration with Schematic Eyes," Ophthalmic and Physiological Optics, Jan. 1996, vol. 16 (4), pp. 348-354.
Rosen R., et al., "Evaluating the Peripheral Optical Effect of Multifocal Contact Lenses," Ophthalmic and Physiological Optics, Nov. 2012, vol. 32 (6), pp. 527-534.
Rosen R., et al., "Have We Misinterpreted the Study of Hoogerheide et al. (1971)?," Optometry and Vision Science, Aug. 2012, vol. 89 (8), pp. 1235-1237.
Rosen R., et al., "Sign-dependent Sensitivity to Peripheral Defocus for Myopes Due to Aberrations," Investigative Ophthalmology & Visual Science, Oct. 17, 2012, vol. 53 (11), pp. 7176-7182.
Rosen R., et al., "Influence of Optical Defocus on Peripheral Vision," Visual Psychophysics and Physiological Optics, Jan. 2011, vol. 52 (1), pp. 318-323.
Rosen R., "Peripheral Vision: Adaptive Optics and Psychophysics," Doctoral Thesis Department of Applied Physics Royal Institute of Technology Stockholm, Sweden Apr. 2013, 86 pages.
Siedlecki D., et al., "Radial Gradient index Intraocular Lens: a Theoretical Model," Journal of Modern Optics, Feb. 20-Mar. 10, 2008, vol. 55 (4-5), pp. 639-647.
Terwee T., et al., "Visualization of the Retinal Image in an Eye Model With Spherical and Aspheric, Diffractive, and Refractive Multifocal Intraocular Lenses," Journal of Refractive Surgery, Mar. 2008, vol. 24 (3), pp. 223-232.
Van Den Berg T.J., "Analysis of Intraocular Straylight, Especially in Relation to Age," Optometry and Vision Science, Feb. 1995, vol. 72 (2), pp. 52-59.
Van Meeteren A., "Calculations on the Optical Modulation Transfer Function of the Human Eye for White Light," Optica Acta, May 1974, vol. 21 (5), pp. 395-412.
Villegas E.A., et al., "Correlation between Optical and Psychophy, Sical Parameters as a Function of Defocus," Optometry and Vision Science, Jan. 1, 2002, vol. 79 (1), pp. 60-67.
International Search Report and Written Opinion for Application No. PCT/IB2017/000318, dated Aug. 4, 2017, 14 pages.

* cited by examiner

   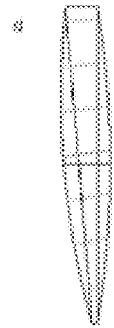 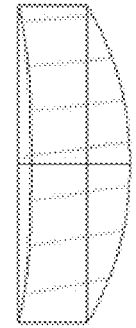
FIG. 7A     FIG. 7B     FIG. 7C     FIG. 7D     FIG. 7E
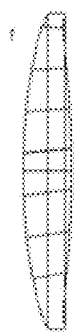  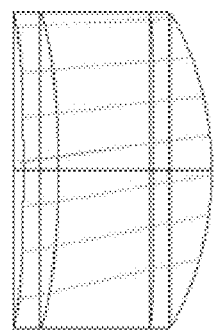 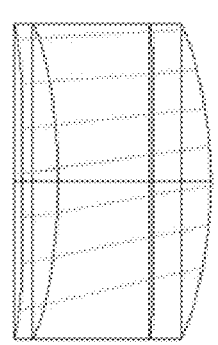
FIG. 7F     FIG. 7G     FIG. 7H     FIG. 7I
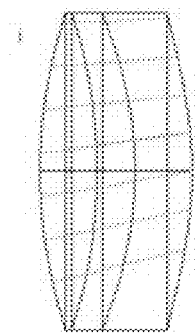 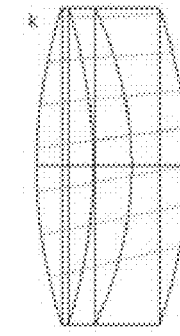 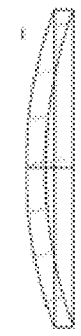 
FIG. 7J     FIG. 7K     FIG. 7L     FIG. 7M

INTRAOCULAR LENS THAT IMPROVES OVERALL VISION WHERE THERE IS A LOCAL LOSS OF RETINAL FUNCTION

CROSS-REFERENCE TO RELATED APPLICATIONS

This application claims benefit under 35 U.S.C. §119(e) of U.S. Provisional Application No. 61/950,757, filed on Mar. 10, 2014, titled "INTRAOCULAR LENS THAT IMPROVES OVERALL VISION WHERE THERE IS A LOSS OF CENTRAL VISION." This application also claims benefit under 35 U.S.C. §119(e) of U.S. Provisional Application No. 61/987,647, filed on May 2, 2014. The entire content of each of the above identified applications is incorporated by reference herein in its entirety for all it discloses and is made part of this specification.

This application is also related to U.S. application Ser. No. 14/644,101, filed concurrently herewith on Mar. 10, 2015, titled "DUAL-OPTIC INTRAOCULAR LENS THAT IMPROVES OVERALL VISION WHERE THERE IS A LOCAL LOSS OF RETINAL FUNCTION,". This application is also related to U.S. application Ser. No. 14/644,110, filed concurrently herewith on Mar. 10, 2015, titled "ENHANCED TORIC LENS THAT IMPROVES OVERALL VISION WHERE THERE IS A LOCAL LOSS OF RETINAL FUNCTION,". This application is also related to U.S. application Ser. No. 14/644,107, filed concurrently herewith on Mar. 10, 2015, titled "PIGGYBACK INTRAOCULAR LENS THAT IMPROVES OVERALL VISION WHERE THERE IS A LOCAL LOSS OF RETINAL FUNCTION,". The entire content of each of the above identified applications is incorporated by reference herein in its entirety for all it discloses and is made part of this specification.

BACKGROUND

Field

This disclosure generally relates to using an intraocular lens to improve overall vision where there is a local loss of retinal function (e.g., loss of central vision due to a central scotoma), and more particularly to using an intraocular lens to focus light incident at oblique angles on the patient's eye onto a location of the peripheral retina.

Description of Related Art

Surgery on the human eye has become commonplace in recent years. Many patients pursue eye surgery to treat an adverse eye condition, such as cataract, myopia and presbyopia. One eye condition that can be treated surgically is age-related macular degeneration (AMD). Other retinal disorders affect younger patients. Examples of such diseases include Stargardt disease and Best disease. Also, a reverse form of retinitis pigmentosa produces an initial degradation of central vision. A patient with AMD suffers from a loss of vision in the central visual field due to damage to the retina. Patients with AMD rely on their peripheral vision for accomplishing daily activities. A major cause of AMD is retinal detachment which can occur due to accumulation of cellular debris between the retina and the vascular layer of the eye (also referred to as "choroid") or due to growth of blood vessels from the choroid behind the retina. In one type of AMD, damage to the macula can be arrested with the use of medicine and/or laser treatment if detected early. If the degradation of the retina can be halted a sustained vision benefit can be obtained with an IOL. For patients with continued degradation in the retina a vision benefit is provided at least for a time.

SUMMARY

The systems, methods and devices of the disclosure each have several innovative aspects, no single one of which is solely responsible for the desirable attributes disclosed herein.

Ophthalmic devices that magnify images on the retina can be used to improve vision in patients suffering from AMD. Such ophthalmic devices can include a high optical power loupe or a telescope. Intraocular lenses (IOLs) that magnify images on the retina can also be implanted to improve vision in patients suffering from AMD. Such IOLs are based on a telescopic effect and can magnify images between about 1.3 times and about 2.5 times, which will improve resolution at the cost of a reduced visual field. However, such IOLs may not provide increased contrast sensitivity.

Various embodiments disclosed herein include ophthalmic devices (such as, for example, IOLs, contact lenses, etc.) that take into consideration the retinal structure and image processing capabilities of the peripheral retina to improve vision in patients suffering from AMD. The ophthalmic devices described herein can be lightweight and compact. Various embodiments of the ophthalmic devices described herein can focus incident light at a preferred area of the peripheral retina. Various embodiments of the ophthalmic devices described herein can correct for optical errors occurring in the image formed in the area of the peripheral retina due to optical effects such as oblique astigmatism and coma.

The embodiments described herein are directed to ophthalmic lenses, such as an IOL, and a system and method relating to providing ophthalmic lenses that can improve visual acuity and/or contrast sensitivity when there is a loss of central vision by focusing incident light onto an area on the peripheral retina where vision is best. Such ophthalmic lenses can include refractive structures such as prisms and diffractive structures such as gratings to focus incident light onto the preferred retinal location.

One aspect of the subject matter described in this disclosure can be implemented in an intraocular lens configured to improve vision for eyes having no or reduced foveal vision. The intraocular lens comprises a first zone having an optical axis which intersects the retina of the eye at a location external to the fovea; and a second zone having an optical axis which intersects the retina of the eye at the fovea, wherein the first zone has a power that is greater than the second zone. Embodiments further include an intraocular lens comprised of an optic configured to provide multi-refraction for focusing light on an area surrounding a PRL. The intraocular lens may be comprised of two refractions, wherein one of the two refractions is in the horizontal field and the other of the two refractions is in the vertical field. It is also envisioned that the multi-refraction may be comprised of a continuous refraction for a horizontal line below or above a scotoma. Or, the multi-refraction may be comprised of a horizontal line on both sides of the scotoma. It is further envisioned that one surface of the optic may be comprised of either a multifocal pattern or an extended depth of focus pattern.

Another aspect of the subject matter described in this disclosure can be implemented in a method for improving vision where there is no or reduced foveal vision using an intraocular lens with at least two zones. The method comprising: determining a deflected optical axis which intersects a retina of a user at a preferred retinal locus; modifying a first zone of the intraocular lens to redirect incident light along the deflected optical axis; modifying a second zone of the intraocular lens to direct incident light along an undeflected optical axis which intersects a retina of a user at the fovea; and adjusting a power of the first zone to be greater than a power of the second zone.

One aspect of the subject matter described in this disclosure can be implemented in an intraocular lens configured to improve vision where there is a loss of retinal function (e.g., a loss of foveal vision), the intraocular lens comprising: a redirection element configured to redirect incident light along a deflected optical axis which intersects a retina of a user at a preferred retinal locus. The redirection element comprises a surface with a slope profile that is tailored such that, in use, the intraocular lens: redirects incident light along the deflected optical axis; focuses the incident light at the preferred retinal locus; and reduces optical wavefront errors, wherein the slope profile is tailored to redirect and focus the incoming rays on the preferred retinal locus. The slope profile can be tailored based at least in part on a solution to an analytical equation that is a function of a distance from the IOL vertex to the original focus (l), an index of refraction of the IOL ($n_l$), an index of refraction of the aqueous environment ($n_{aq}$), an angle inside the eye to the preferred retinal locus relative to a back vertex of the IOL ($a_p$), a radial position of the IOL (x), and/or the posterior radius of curvature of the IOL (r), the analytical equation given by the following:

$$\text{slope}(x) = -\cos^{-1}\left(\frac{n_{aq}\cos\alpha - n_l\cos\beta}{\sqrt{n_{aq}^2 + n_l^2 - 2n_{aq}n_l\sin\alpha\sin\beta - 2n_{aq}n_l\cos\alpha\cos\beta}}\right),$$

wherein $$\alpha = \tan^{-1}\left(\frac{l\sin a_p - x}{l\cos a_p - r - \sqrt{r^2 - x^2}}\right),$$

and wherein $$\beta = \sin^{-1}\left(\frac{n_{aq}}{n_l}\sin\left(\tan^{-1}\left(\frac{-x}{l - r - \sqrt{r^2 - x^2}}\right) + \sin^{-1}\left(\frac{x}{r}\right)\right)\right).$$

In some implementations, the slope profile can be tailored based at least in part on an analytical solution to an equation describing an eye of a patient. In some implementations, the slope profile can be tailored based at least in part on simulations performed using ray tracing techniques. In some implementations, the slope profile can be determined analytically using an equation that incorporates an axial length to the preferred retinal locus, an angle of the deflected optical axis relative to an undeflected optical axis, and a radial position of the preferred retinal locus. In various implementations, the slope profile can be tailored using an iterative procedure that adjusts a portion of the slope profile to account for a thickness of the redirection element.

The redirection element can comprise a plurality of zones. Each zone can have a slope profile that is tailored based at least in part on the solution to an equation (e.g., the analytical equation given above). In various implementations, a thickness of the redirection element can be less than or equal to 0.5 mm. In various implementations, a curvature of a posterior surface of the intraocular lens is configured to provide a focused image at the fovea of the retina of the patient. In various implementations, the redirection element can be a separate, additional surface on the intraocular lens. In some implementations, the redirection element can be a ring structure. In some implementations, the redirection element can cover a central portion of the intraocular lens. The central portion can have a diameter that is greater than or equal to 1.5 mm and less than or equal to 4.5 mm. In various implementations, a posterior surface of the intraocular lens can include the redirection element, and an anterior surface of the intraocular lens can include a second redirection element comprising a plurality of zones, each zone having a slope. In some implementations, a posterior surface and/or an anterior surface of the intraocular lens can be toric, aspheric, higher order aspheric, a Zernike surface or some other complex surface. In various implementations, the posterior surface and/or the anterior surface of the IOL can be configured to reduce astigmatism and coma in the focused image produced at the preferred retinal locus. In various implementations, a portion of the IOL can include the redirection element and another portion of the IOL can be devoid of the redirection element. In such implementations, the portion of the IOL including the redirection element can have an optical power that is different from the portion of the IOL that is devoid of the redirection element.

Another aspect of the subject matter described in this disclosure can be implemented in a method for improving vision where there is no or reduced foveal vision using an intraocular lens and a redirection element having a tailored slope profile. The method comprising: determining a deflected optical axis which intersects a retina of a user at a preferred retinal locus; calculating a tailored slope profile for the redirection element, the tailored slope profile comprising a plurality of slope values calculated at a corresponding plurality of points on a surface of the intraocular lens; determining optical aberrations at the preferred retinal locus based at least in part on redirecting light using the redirection element with the tailored slope profile; adjusting the slope profile to account for a thickness of the redirection element; and determining whether a quality of an image produced by the redirection element with the adjusted tailored slope profile is within a targeted range.

One aspect of the subject matter described in this disclosure can be implemented in a method of using an intraocular lens to improve optical quality at a preferred retinal locus, the method comprising: obtaining an axial length along an optical axis from a cornea to a retina; obtaining an axial length along an axis which deviates from the optical axis and intersects the retina at the preferred retinal locus. The method further comprises determining a corneal power based at least in part on measurements of topography of the cornea; estimating an axial position of the intraocular lens wherein the intraocular lens with initial optical properties at the estimated axial position is configured to provide a focused image at a fovea. The method further comprises adjusting the initial optical properties of the intraocular lens to provide adjusted optical properties, the adjusted optical properties based at least in part on the axial length along the optical axis, the axial length along the deviated axis to the preferred retinal locus, and the corneal power, wherein the adjusted optical properties are configured to reduce peripheral errors at the preferred retinal location in relation to the intraocular lens with the initial optical properties.

Another aspect of the subject matter described in this disclosure can be implemented in an ophthalmic device configured to deflect incident light away from the fovea to a desired location of the peripheral retina. The device comprises an optical lens including an anterior optical surface configured to receive the incident light, a posterior optical surface through which incident light exits the optical lens and an axis intersecting the anterior surface and posterior surface, the optical lens being rotationally symmetric about the axis. The device further comprises an optical component disposed adjacent the anterior or the posterior surface of the optical lens, the optical component having a surface with a refractive index profile that is asymmetric about the axis.

One aspect of the subject matter described in this disclosure can be implemented in an ophthalmic device comprising an optical lens including an anterior optical surface configured to receive the incident light, a posterior optical surface through which incident light exits the optical lens and an optical axis intersecting the anterior surface and posterior surface. The device further comprises an optical component disposed adjacent the anterior or the posterior surface of the optical lens, the optical component including a diffractive element, wherein the optical component is configured to deflect incident light away from the fovea to a desired location of the peripheral retina.

Various implementations disclosed herein are directed towards an intraocular device (e.g, an intraocular lens, an ophthalmic solution, a laser ablation pattern, etc.) that improves visual acuity and contrast sensitivity for patients with central visual field loss, taking into account visual field, distortion or magnification of the image. The device can be configured to improve visual acuity and contrast sensitivity for patients with AMD through specific correction of the optical errors for the still healthy retina that the patient uses for viewing. The device can be configured to correct peripheral errors of the retina with or without providing added magnification. The device can be configured to correct peripheral errors of the retina either without field loss or in combination with magnification. The device can be configured to include a near vision zone. The device can be configured to include multiple optical zones with add power. In various implementations, wherein the device is configured to focus light incident in a large patch including a plurality of angles of incidence is focused in a relatively small area of the retina such that the image has sufficient contrast sensitivity. In various implementations, light incident from a plurality of angles of incidence are focused by the device as an extended horizontal reading zone above or below the fovea. In various implementations, light incident from a plurality of angles of incidence are focused by the device in an area surrounding the fovea and extending upto the full extent of the peripheral visual field. In various implementations, the device is configured to provide sufficient contrast sensitivity for light focused at the fovea for patients with early stages of macular degeneration.

Various implementations of the device can include a redirection element that is configured to redirect incident light towards a peripheral retinal location. Various implementations of the device can include symmetric lenses surfaces with aspheric surfaces. Various implementations of the device can include asymmetric lenses surfaces with aspheric surfaces. Various implementations of the device can include asymmetric/symmetric lenses surfaces with aspheric surfaces having curvatures such that when implanted in the eye a distance between the anterior surface of the lens and the pupil is between 2 mm and about 4 mm and the image formed at a peripheral retinal location at an eccentricity between 7-13 degrees has an average MTF greater than 0.7 for a spatial frequency of about 30 cycles/mm. The aspheric surfaces in various implementations the device can include higher order aspheric terms. In various implementations, the device can include a symmetric optical element with a first surface and a second surface intersected by an optical axis. The thickness of the device along the optical axis can vary between 0.5 mm and about 2.0 mm. The first and the second surfaces can be aspheric. In various implementations, the aspheric surfaces can include higher order aspheric terms.

In various implementations, the device can be configured as a piggyback lens that can be providing in addition to an existing lens that is configured to provide good foveal vision. The piggyback lens can be symmetric or asymmetric. The piggyback lens can be configured to be implanted in the sulcus or in the capsular bag in front of the existing lens.

In various implementations, the device can be configured as a dual optic intraocular lens having a first lens and a second lens. One or both surfaces of the first and the second lens can be aspheric. In various implementations, one or both surfaces of the first and the second lens can include higher order aspheric terms. In various implementations of the dual optic intraocular lens, the optic proximal to the closer to the cornea can have a high positive power and can be configured to be moved either axially in response to ocular forces to provide accommodation. In various implementations of the device described herein, the refractive power provided by optic can be changed in response to ocular forces. The change in the refractive power can be brought about through axial movement or change in the shape of the optic. Various implementations of the device described herein can include a gradient index lens. One or more surfaces of the optics included in various implementations of the device described herein can be diffractive to provide near vision. The optical zones of various implementations of the device described herein can be split for different retinal eccentricities.

Another aspect of the subject matter disclosed herein includes a power calculation diagnostic procedure that measures corneal topography, eye length, retinal curvature, peripheral eye length, pupil position, capsular position, or any combination thereof in order to determine characteristic of the intraocular lens device that improves visual acuity and contrast sensitivity for patients with central visual field loss.

Implementations of intraocular devices described herein can include one or more optics with a large optical zone. The implementations of intraocular devices described herein are configured to focus obliquely incident light in a location of the peripheral retina at an eccentricity between about 5-25 degrees (e.g., eccentricity of 10 degrees, eccentricity of 15 degrees, eccentricity of 20 degrees, etc.). For patient with a well-developed preferred retinal location (PRL), various implementations of the intraocular device can be configured to focus incident light at the PRL. For patients without a well-developed PRL, the implementations of intraocular device described herein can help in the formation of the PRL. This disclosure also contemplates the use of diagnostic devices to determine a region of the peripheral retina which provides the best vision, determining the power of the intraocular device at various locations with the region of the peripheral retina and determining an intraocular device that would correct optical errors including defocus, astigmatism, coma, spherical aberration, chromatic aberration (longitudinal and transverse) at the region of the peripheral retina. When determining the intraocular device that would correct optical errors at the region of the peripheral retina, different figures of merit can be used to characterize the optical performance of different configurations of the intraocular device and the intraocular device that provides the best performance can be selected. The different figures of merit can include MTF at spatial frequencies appropriate for the retinal areas, weighting of retinal areas, neural weighting, and weighting of near vision function.

Another aspect of the subject matter described in this disclosure can be implemented in an intraocular lens configured to improve vision for a patient's eye. The IOL comprises an optic comprising a first surface and a second surface opposite the first surface, the first surface and the second surface intersected by an optical axis. The optic is symmetric about the optical axis. The first and the second surface of the optic are aspheric. The optic is configured to improve image quality of an image produced by light incident on the patient's eye at an oblique angle with respect to the optical axis and focused at a peripheral retinal location disposed at a distance from the fovea. The image quality is improved by reducing oblique astigmatism at the peripheral retinal location.

The image quality can also be improved by reducing coma at the peripheral retinal location. The oblique angle can be between about 1 degree and about 25 degrees. The peripheral retinal location can be disposed at an eccentricity of about 1 degree to about 25 degrees with respect to the fovea in the horizontal or the vertical plane. For example, the peripheral retinal location can be disposed at an eccentricity between about 7 degrees and about 13 degrees in the horizontal plane. As another example, the peripheral retinal location can be disposed at an eccentricity between about 1 degree and about 10 degrees in the vertical plane. At least one of the surfaces of the first or second viewing element can be aspheric. At least one of the surfaces of the first or second viewing element can be a toric surface, a higher order aspheric surface, an aspheric Zernike surface or a Biconic Zernike surface. An image formed by the IOL at the peripheral retinal location can have a modulation transfer function (MTF) of at least 0.2 (e.g., at least 0.3, at least 0.4, at least 0.5. at least 0.6, at least 0.7, at least 0.8, at least 0.9 or values there between) for a spatial frequency of 30 cycles/mm for both the tangential and the sagittal foci. An image formed by the IOL at the fovea can have a MTF of at least 0.2 (e.g., at least 0.3, at least 0.4, at least 0.5. at least 0.6, at least 0.7, at least 0.8, at least 0.9 or values there between) for a spatial frequency of 100 cycles/mm for both the tangential and the sagittal foci.

The optic can be a meniscus lens with a vertex curving inwards from edges of the optic. One of the first or second surface can include redirecting elements. The redirecting elements can have a slope profile as described herein. The redirecting element can comprise one or more diffractive elements and/or one or more prismatic features. In various implementations, the optic can include diffractive features, prismatic features, echellettes etc. to further improve the image quality at the peripheral retinal location. For example, the first and/or the second viewing element can include diffractive features to provide increases depth of focus.

Another aspect of the subject matter described in this disclosure can be implemented in a method of designing an intraocular lens (IOL) configured to be implanted in a patient's eye. The method comprises determining a first surface profile of the optic and determining a second surface profile of the optic. The determined surface profiles are such that the optic has an optical power that reduces optical errors in an image produced at a peripheral retinal location disposed at a distance from the fovea, wherein the image is produced by focusing light incident on the patient's eye at an oblique angle with respect to an optical axis intersecting the patient's eye at the peripheral retinal location. The first surface profile and the second surface profile can be aspheric.

The optical power of the IOL that reduces optical errors at the peripheral retinal location can be obtained from a measurement of an axial length along an axis which deviates from the optical axis and intersects the retina at the peripheral retinal location. The optical power of the IOL that reduces optical errors at the peripheral retinal location can be obtained from an estimate of an axial length along an axis which deviates from the optical axis and intersects the retina at the peripheral retinal location, the estimate based on measured ocular characteristics of the patient obtained using a diagnostic instrument. The measured ocular characteristics can include axial length along the optical axis, corneal power based at least in part on measurements of topography of the cornea, pre-operative refractive power and other parameters. The image produced at the peripheral retinal location can have reduced peripheral astigmatism and/or coma.

Another aspect of the subject matter disclosed herein can be implemented in a method of selecting an intraocular lens (IOL) configured to be implanted in a patient's eye. The method comprises obtaining at least one characteristic of the patient's eye using a diagnostic instrument; and selecting an IOL having an optical power that reduces optical errors in an image produced at a peripheral retinal location of the patient's eye disposed at a distance from the fovea, wherein the IOL is configured to produce an image by focusing light incident on the patient's eye at an oblique angle with respect to an optical axis intersecting the patient's eye at the peripheral retinal location. The optical power of the IOL is obtained and/or optimized based on the obtained characteristic. A first surface of the IOL can be aspheric. The IOL can be symmetric about the optical axis. A second surface of the IOL can be aspheric. The image can have reduced coma and/or astigmatism. The oblique angle can be between about 1 degree and about 25 degrees. The IOL can be configured such that the image has a modulation transfer function (MTF) of at least 0.3 for a spatial frequency of 30 cycles/mm for both tangential and sagittal foci. The IOL can be configured to provide at least 0.5 Diopter of astigmatic correction at the peripheral retinal location The obtained characteristic can include at least one of axial length along the optical axis of the patient's eye, corneal power based at least in part on measurements of topography of the cornea, an axial length along an axis which deviates from the optical axis and intersects the retina at the peripheral retinal location, a shape of the retina or a measurement of optical errors at the peripheral retinal location. In some implementations, the optical power can be obtained from an estimate of an axial length along an axis which deviates from the optical axis and intersects the retina at the peripheral retinal location. The estimate can be based on the axial length along the optical axis of the patient's eye and corneal power.

At least one of the surfaces of the first viewing element or the second viewing element can include a redirecting element. The redirecting element can have a tailored slope profile as discussed herein. The redirecting element can include a diffractive feature and/or a prismatic feature.

The methods and systems disclosed herein can also be used to customize IOLs based on the geometry of a patient's retina, the extent of retinal degeneration and the geometry and condition of other structures in the patient's eye. Various embodiments described herein can also treat other conditions of the eye such as cataract and correct for presbyopia, myopia and/or astigmatism in addition to improving visual acuity and/or contrast sensitivity of peripheral vision.

The methods and systems described herein to deflect incident light away from the fovea to a preferred retinal location (PRL) can also be applied to spectacle lenses, contact lenses, or ablation patterns for laser surgeries (e.g., LASIK procedures).

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

Example implementations disclosed herein are illustrated in the accompanying schematic drawings, which are for illustrative purposes only.

FIG. 4A-1 is a diagram of an eye implanted with an intraocular lens that deflects incident light to a preferred retinal location (PRL). FIG. 4A-2 is a ray trace illustrating rays originating from the posterior surface of a lens.

FIG. 5D-1 and FIG. 5D-2 illustrate regions of peripheral retina where the optic illustrated in FIG. 5A can improve image quality. FIG. 5D-3 shows the area around a preferred retinal location (PRL) towards which incident light from the off-axis object is directed by the IOL 500.

FIG. 7A shows a cross-section view of an embodiment of a standard intraocular lens (IOL) configured to provide improved vision at a location of the peripheral retina.

FIG. 7B shows a cross-section view of an embodiment of an enhanced toric IOL configured to provide improved vision at a location of the peripheral retina.

FIG. 7C shows a cross-section view of an embodiment of a symmetric single optic IOL configured to provide improved vision at a location of the peripheral retina.

FIG. 7D shows a cross-section view of an embodiment of an asymmetric single optic IOL configured to provide improved vision at a location of the peripheral retina.

FIG. 7E shows a cross-section view of an embodiment of a thick symmetric IOL configured to provide improved vision at a location of the peripheral retina.

FIG. 7F shows a cross-section view of an embodiment of a moved symmetric IOL configured to provide improved vision at a location of the peripheral retina.

FIG. 7G shows a cross-section view of an embodiment of a moved asymmetric IOL configured to provide improved vision at a location of the peripheral retina.

FIG. 7H shows a cross-section view of an embodiment of a dual optic IOL configured to provide improved vision at a location of the peripheral retina.

FIG. 7I shows a cross-section view of an embodiment of a dual optic IOL configured to provide improved vision at a location of the peripheral retina and at the fovea.

FIG. 7J shows a cross-section view of an embodiment of an accommodating dual optic IOL configured to provide improved vision at a location of the peripheral retina.

FIG. 7K shows a cross-section view of an embodiment of an accommodating dual optic IOL configured to provide improved vision at a location of the peripheral retina and at the fovea.

FIG. 7L shows a cross-section view of an embodiment of a symmetric piggyback IOL configured to provide improved vision at a location of the peripheral retina and at the fovea.

FIG. 7M shows a cross-section view of an embodiment of an asymmetric piggyback IOL configured to provide improved vision at a location of the peripheral retina and at the fovea.

Like reference numbers and designations in the various drawings indicate like elements.

DETAILED DESCRIPTION

It is to be understood that the figures and descriptions have been simplified to illustrate elements that are relevant for a clear understanding of embodiments described herein, while eliminating, for the purpose of clarity, many other elements found in typical lenses, lens systems and lens design methods. Those of ordinary skill in the arts can recognize that other elements and/or steps are desirable and may be used in implementing the embodiments described herein.

The terms "power" or "optical power" are used herein to indicate the ability of a lens, an optic, an optical surface, or at least a portion of an optical surface, to focus incident light for the purpose of forming a real or virtual focal point. Optical power may result from reflection, refraction, diffraction, or some combination thereof and is generally expressed in units of Diopters. One of ordinary skill in the art will appreciate that the optical power of a surface, lens, or optic is generally equal to the refractive index of the medium (n) of the medium that surrounds the surface, lens, or optic divided by the focal length of the surface, lens, or optic, when the focal length is expressed in units of meters.

The angular ranges that are provided for eccentricity of the peripheral retinal location in this disclosure refer to the visual field angle in object space between an object with a corresponding retinal image on the fovea and an object with a corresponding retinal image on a peripheral retinal location.

Figure 1:
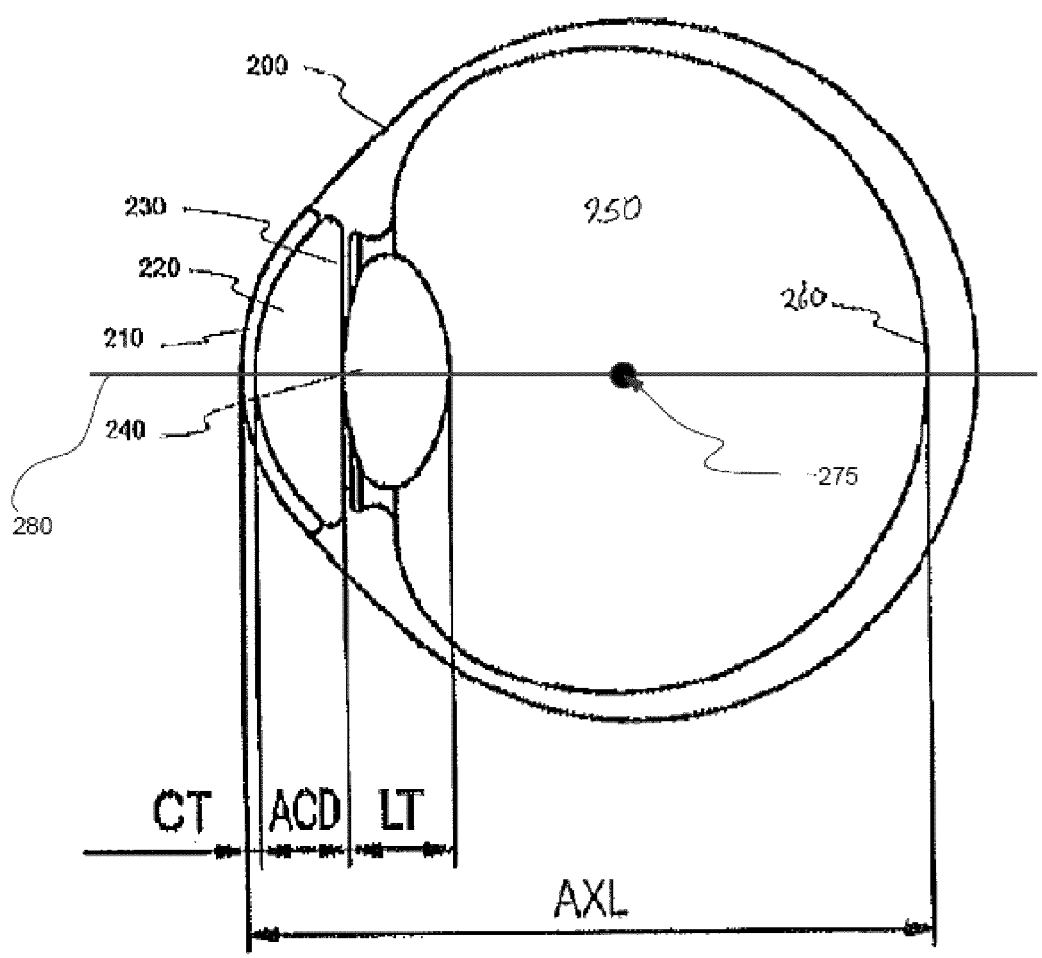
FIG. 1 is a diagram illustrating the relevant structures and distances of the human eye.

FIG. 1 is a schematic drawing of a human eye 200. Light enters the eye from the left of FIG. 1, and passes through the cornea 210, the anterior chamber 220, a pupil defined by the iris 230, and enters lens 240. After passing through the lens 240, light passes through the vitreous chamber 250, and strikes the retina, which detects the light and converts it to a signal transmitted through the optic nerve to the brain (not shown). The eye 200 is intersected by an optical axis 280. The cornea 210 has corneal thickness (CT), which is the distance between the anterior and posterior surfaces of the center of the cornea 210. The corneal center of curvature 275 can coincide with geometric center of the eye 200. The anterior chamber 220 has an anterior chamber depth (ACD), which is the distance between the posterior surface of the cornea 210 and the anterior surface of the lens 240. The lens 240 has lens thickness (LT) which is the distance between the anterior and posterior surfaces of the lens 240. The eye has an axial length (AXL) which is the distance between the center of the anterior surface of the cornea 210 and the fovea 260 of the retina, where the image is focused. The LT and AXL vary in eyes with normal accommodation depending on whether the eye is focused on near or far objects.

The anterior chamber 220 is filled with aqueous humor, and optically communicates through the lens 240 with the vitreous chamber 250. The vitreous chamber 250 is filled with vitreous humor and occupies the largest volume in the eye. The average adult eye has an ACD of about 3.15 mm, although the ACD typically shallows by about 0.01 mm per year. Further, the ACD is dependent on the accommodative state of the lens, i.e., whether the lens 240 is focusing on an object that is near or far.

Figure 2:
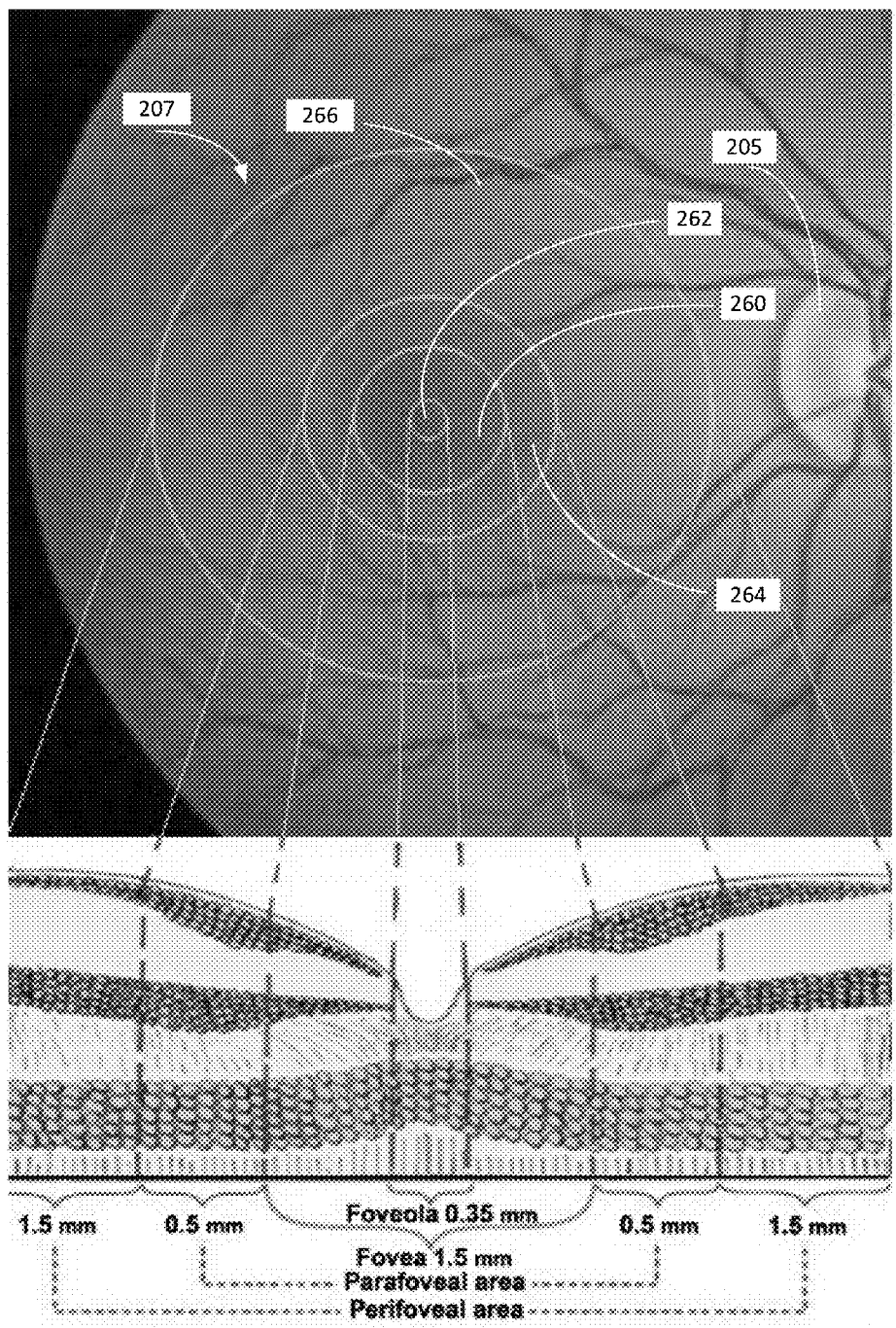
FIG. 2 illustrates different regions of the retina around the fovea.

FIG. 2 illustrates different regions of the retina around the fovea 260. The retina includes a macular region 207. The macular region 207 has two areas: central and peripheral. Light focused on the central area contributes to central vision and light focused on the peripheral area contributes to peripheral vision. The central region is used to view objects with higher visual acuity, and the peripheral region is used for viewing large objects and for capturing information about objects and activities in the periphery, which are useful for activities involving motion and detection.

The macular region 207 is approximately 5.5 mm in diameter. The center of the macular region 207 is approximately 3.5 mm lateral to the edge of the optic disc 205 and approximately 1 mm inferior to the center of the optic disc 205. The shallow depression in the center of the macula region 207 is the fovea 260. The fovea 260 has a horizontal dimension (diameter) of approximately 1.5 mm. The curved wall of the depression gradually slopes to the floor which is referred to as the foveola 262. The diameter of the foveola 262 is approximately 0.35 mm. The annular zone surrounding the fovea 260 can be divided into an inner parafoveal area 264 and an outer perifoveal area 266. The width of the parafoveal area 264 is 0.5 mm and of the perifoveal area 266 is 1.5 mm.

For the general population incident light is focused on the fovea 260. However, in patients suffering from AMD, a scotoma develops in the foveal region which leads to a loss in central vision. Such patients rely on the region of the peripheral retina around the fovea (e.g., the macular region 207) to view objects. For example, patients with AMD can focus incident light on the PRL either by using a magnifying lens that enlarges the image formed on the retina such that a portion of the image overlaps with a portion of the peripheral retina around the fovea or by rotating the eye or the head, thus using eccentric fixation such that light from the object incident at oblique angles is focused on a portion of the peripheral retina around the fovea. The visual outcome for patients suffering from AMD can be improved if optical refractive errors resulting from oblique incidence of light or coma were corrected. In some AMD patients, a portion of the peripheral retina around the fovea may have has greater visual acuity and contrast sensitivity compared to other portions of the peripheral retina. This portion is referred to as the preferred retinal location (PRL). The visual outcome for such patients may be improved if incident light were focused at the PRL and the ophthalmic solutions corrected for optical refractive errors at the PRL. This is explained in detail below.

Figure 3A:
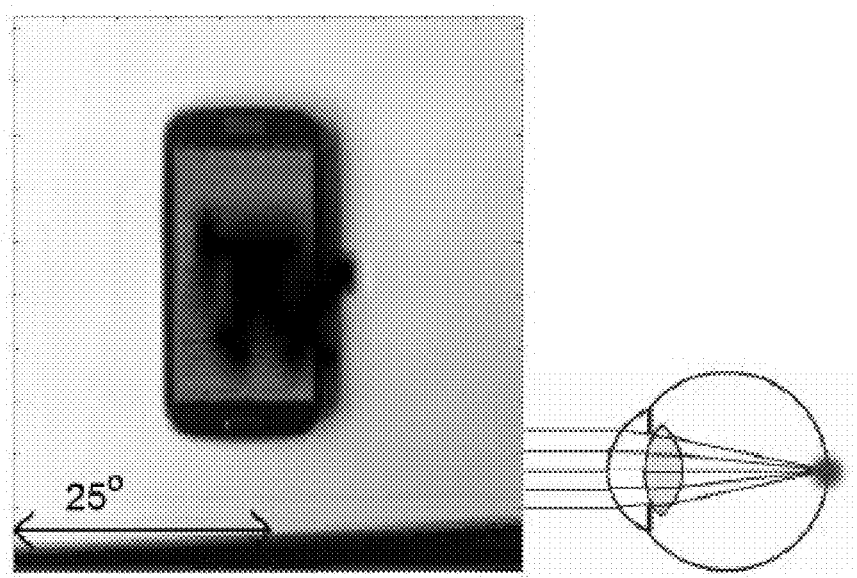
FIGS. 3A-3K illustrate simulated vision with a central scotoma along with ophthalmic device embodiments. A ray diagram lies to the right of each simulation.
Figure 3B:
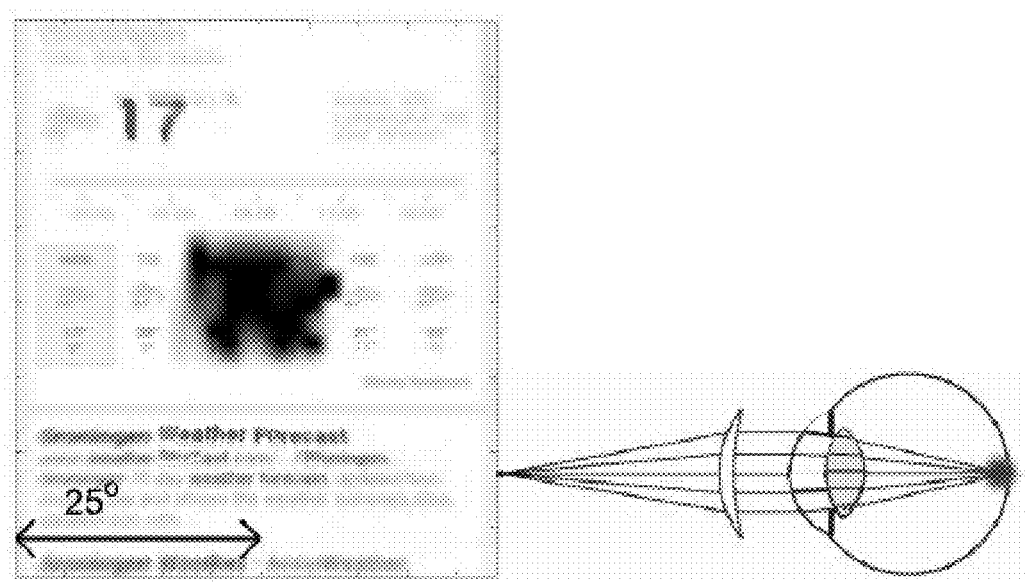
Figure 3C:
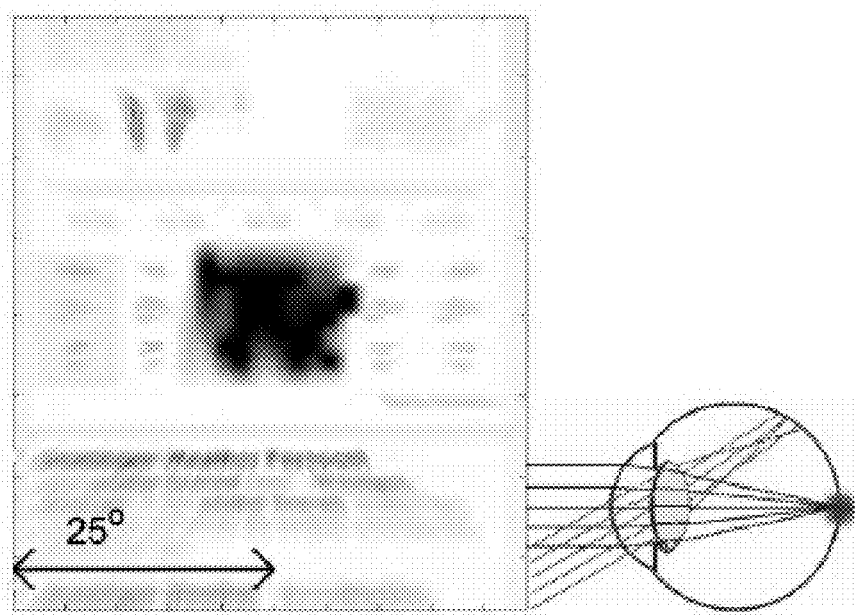

Consider a patient suffering from AMD who desires to view a smart phone at a normal distance (23 cm simulated here). In such a patient, the scotoma will block out the view as seen in FIG. 3A. One solution to improve the visual outcome is to bring the object of interest closer to the eye. This requires a magnifying glass to place the object optically at infinity. FIG. 3B illustrates the simulated view of a smart phone viewed with the aid of a magnifying glass by a patient with a central scotoma. The effect of the magnifying glass is to reduce the object distance and enlarge the size of the image formed on the retina such that it overlaps with a portion of the peripheral retina around the fovea. For the purpose of simulations, it is assumed that the magnifying glass is used and hence the phone is assumed to be at a distance of 7.5 cm. If the patient has cataract in addition to AMD and is implanted with a standard IOL, the peripheral errors will increase. FIG. 3C shows the simulated view of a smart phone viewed by a patient implanted with a standard IOL and who also suffers from AMD. A comparison of FIGS. 3B and 3C illustrates that the smart phone screen appears more blurry when viewed by a patient implanted with a standard IOL due to the increase in peripheral errors.

Figure 3D:
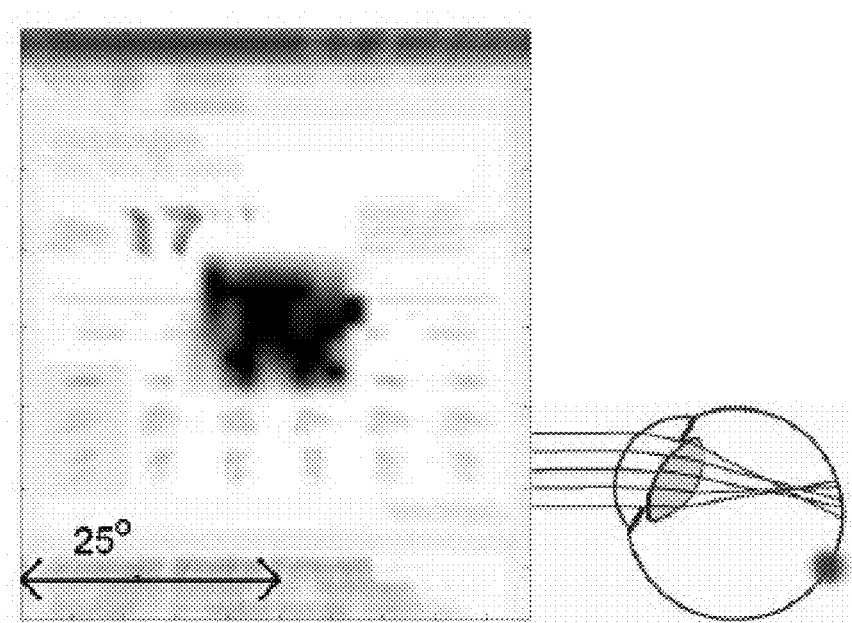

Another solution to improve visual outcome is to utilize eccentric fixation to focus light from a visual interest on to a portion of the peripheral retina. FIG. 3D illustrates a simulated view of a smart phone viewed using eccentric fixation to focus light from the smart phone screen to a position on the peripheral retina located about 12.5 degrees away from the fovea. Since, the image formed at the position on the peripheral retina is formed by light that is obliquely incident, refractive errors arising from the oblique incidence of light may degrade the visual quality. Accordingly, ophthalmic solutions that can correct optical refractive errors arising from oblique incidence of light may benefit AMD patients who rely on eccentric fixation to view objects.

Figure 3E:
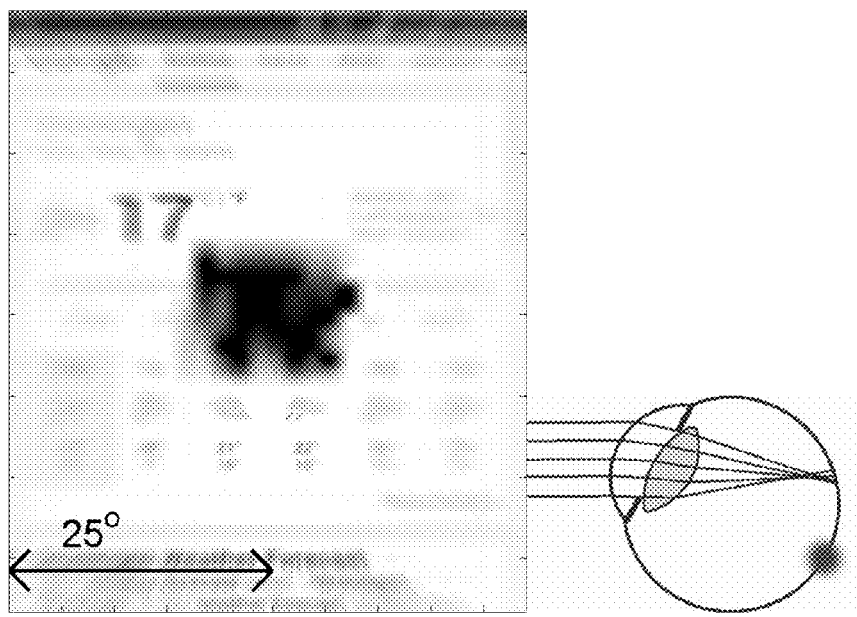

By selecting an IOL with appropriate refractive properties, the image quality at a peripheral retinal location can be improved. For example, the IOL in FIG. 3E is selected to correct about 2.5 D of astigmatism and about 0.7 D of sphere. A comparison of FIGS. 3E and 3D shows that the simulated image in FIG. 3E is less blurry than the simulated image in FIG. 3D.

Figure 3F:
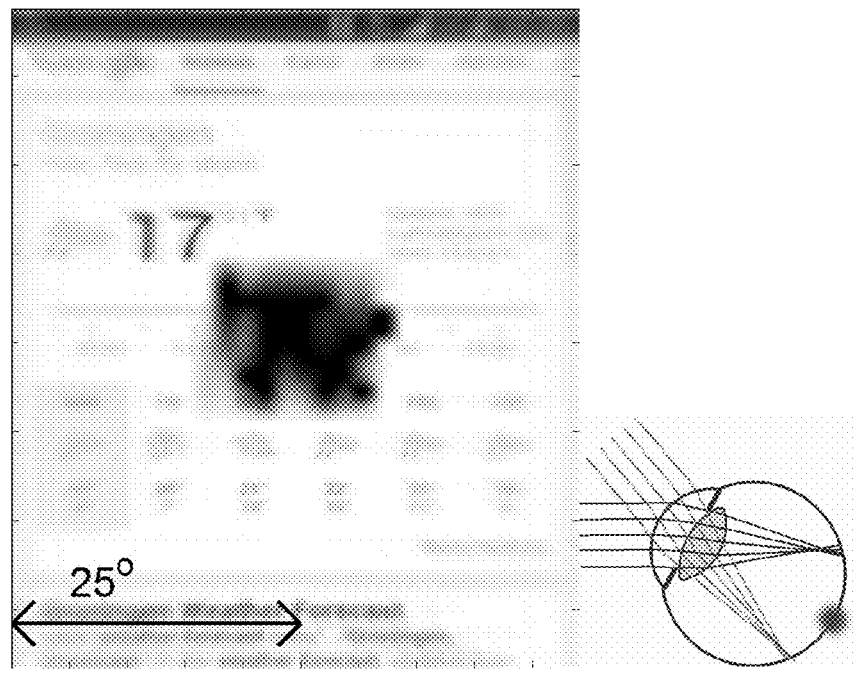

To increase contrast sensitivity in different portions of the retina including the PRL, it may be advantageous to increase the depth of field. It is found that if large amounts of aberrations, e.g. greater than about 0.5 µm of spherical aberration for a 5 mm pupil, are imposed, the eye becomes more tolerant to the refractive errors, at the slight cost of image quality at the PRL. This is illustrated in FIG. 3F.

Figure 3G:
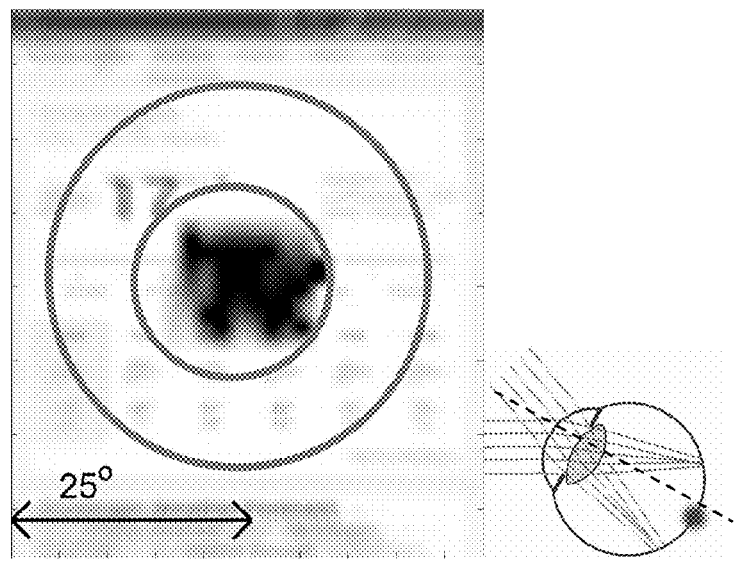

Another method to increase contrast sensitivity in different portions of the retina including the PRL includes providing multi-refraction for the area surrounding the PRL. In many cases, due to the symmetry of the eye, it can be sufficient to provide two refraction zones: one for the horizontal field and one for the vertical field. Each refractive zone can be symmetrically disposed around the fovea. For example, one refractive zone can be disposed about a location that is at an angle of about 12.5 degrees with respect to an optical axis 2501 intersecting the cornea and the retina and passing through the fovea. In various implementations, the two refractive zones can be disposed asymmetrically with respect to the optical axis 2501. Together, the two refractive zones can create a circle of good vision around the scotoma, as illustrated in FIG. 3G. The area between the two circles 2505 and 2510 represents the area of increased contrast sensitivity in FIG. 3G.

Figure 3H:
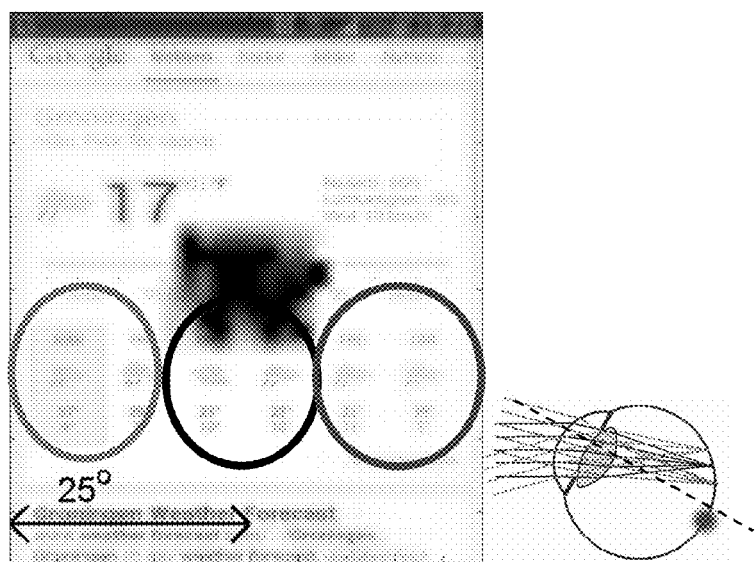

Based on this, an IOL configured for reading can create a continuous or piece-wise continuous linear refractive region disposed above or below the scotoma. The linear refractive region can include multiple refractive zones. FIG. 3H illustrates an implementation of a linear refractive region including three refractive zones 2515, 2520 and 2535 created by an IOL that is configured for reading.

Figure 3I:
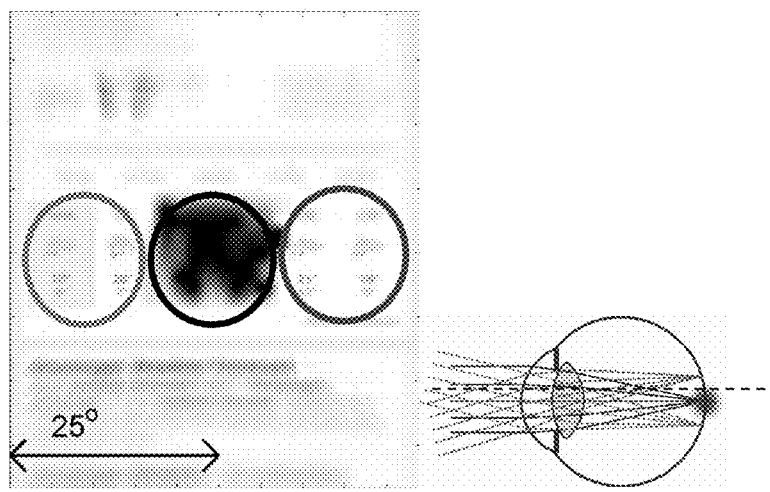

The implementation of the IOL illustrated in FIG. 3H relies on eccentric fixation to move the visual field of interest above or below the scotoma. However, some patients may not desire to use eccentric fixation. For such patients, an IOL configured for reading can provide a linear refraction region on both sides of the scotoma. In various implementations, an IOL providing a linear refraction region on both sides of the scotoma can be accomplished just a single refractive correction, due to the symmetry of the peripheral errors, as shown in FIG. 3I.

Figure 3J:
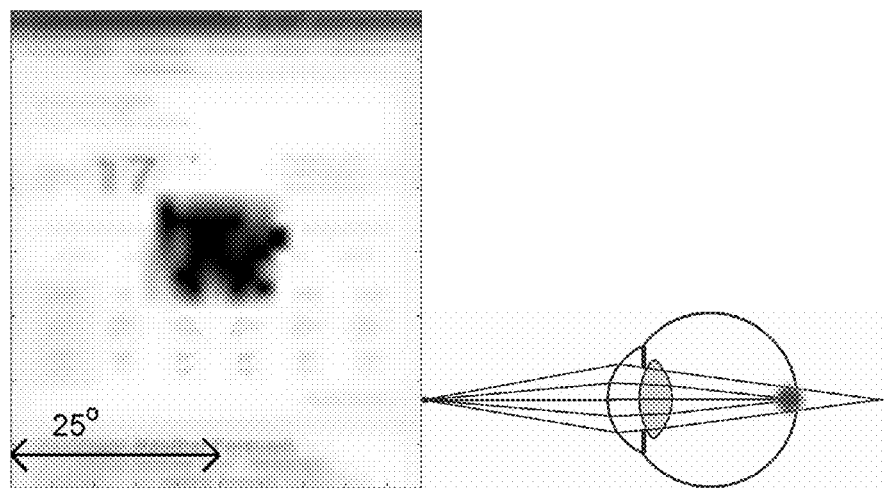
Figure 3K:
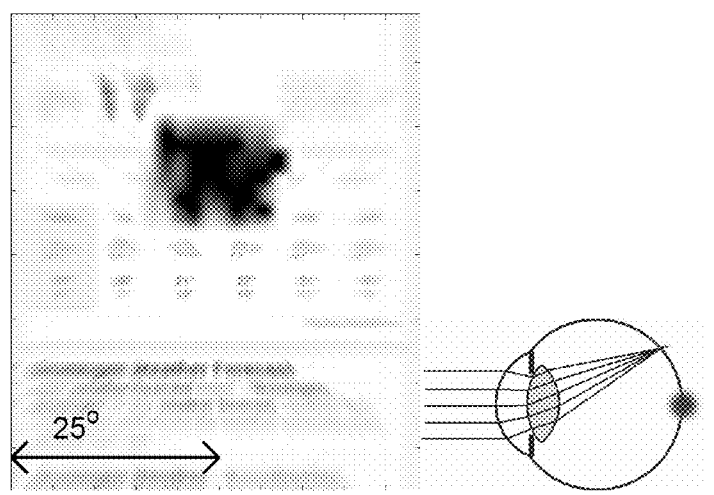

So far, it has been assumed that the patient wears a magnifying aid when looking at close objects (a single strong lens, also called a loupe). However, all the implementations mentioned above can be configured to provide good vision even without the aid of a magnifying element. All the implementations discussed above can be combined with a multifocal approach, where part of the IOL is powered for a far distance, and another part is powered for a very close distance, as shown in FIG. 3J. Furthermore, all the implementations mentioned above can also be combined with the redirection solution, described in here with reference to FIGS. 8-28. For example, FIG. 3K illustrates an implementation of an IOL that includes a redirection element such that light incident along a direction that is substantially parallel to the optical axis of the eye is focused at a PRL. In such implementations, the patient does not have to rely on eccentric fixation to have increased contrast sensitivity.

Figures 1, 4A:
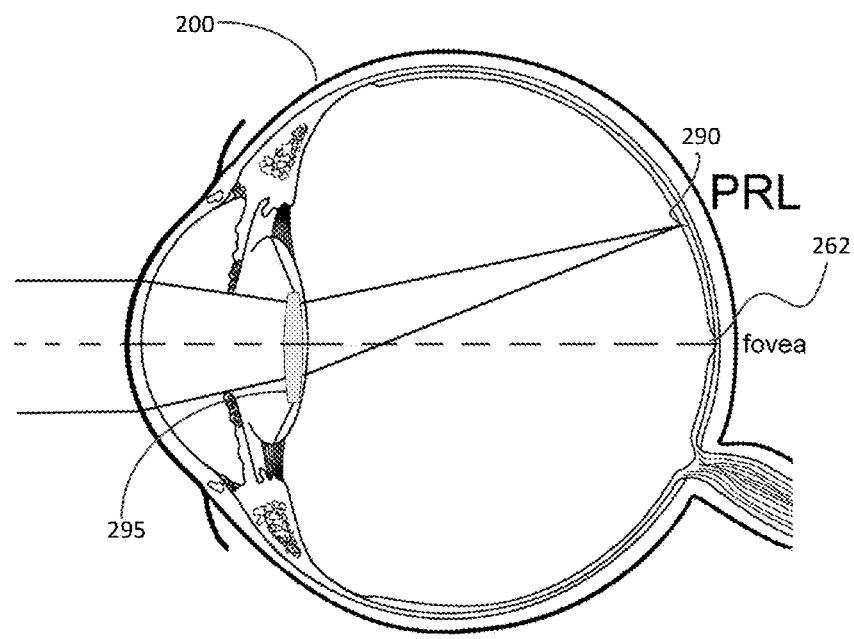
Figures 2, 4A:
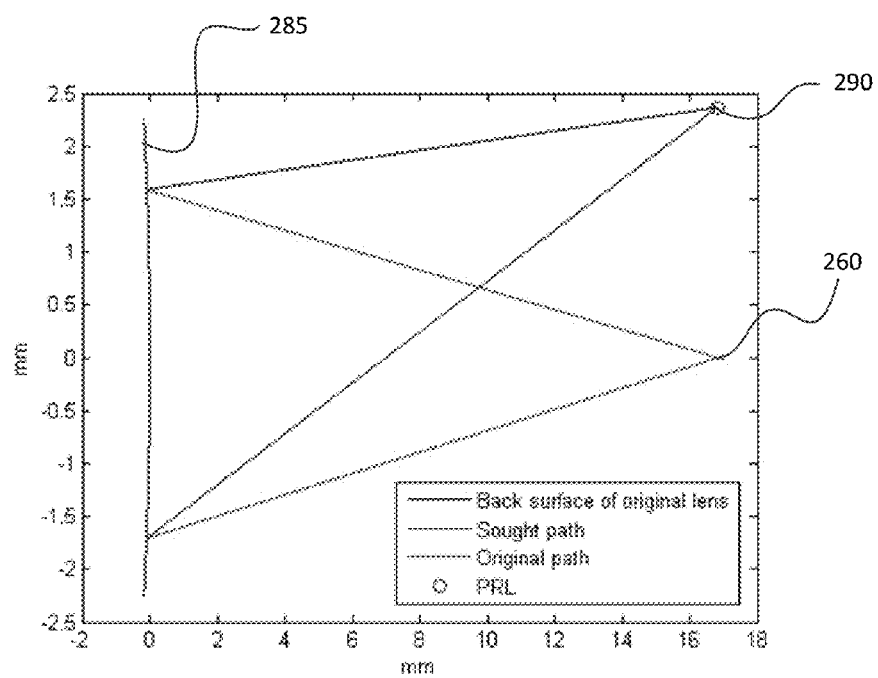

As discussed above, some patient may have a well-developed PRL and may prefer focusing incident light on the PRL. Such patients can benefit from an IOL that can focus light at the PRL instead of the fovea. FIG. 4A-1 is a diagram of the eye 200 implanted with an IOL 295 that deflects incident light away from the fovea 260 to the PRL 290. FIG. 4A-2 is a ray trace illustrating rays originating from the posterior surface 285 of a lens, such as, for example, the natural lens 240 or an intraocular lens configured to provide good foveal vision. The lens is configured such that the rays originating from the posterior surface 285 of the lens are focused on the fovea 260. Patients suffering from AMD suffer from central vision loss and rely on peripheral vision to accomplish their daily tasks. Usually, in such patients a portion 290 of the peripheral area of the macular regions 207 has greater acuity and contrast sensitivity compared to other portions of the peripheral area. The portion 290 of the peripheral area of the macular regions 207 that has greater acuity and contrast sensitivity compared to other portions of the peripheral area is referred to as the preferred retinal location (PRL). Since, patients with AMD are not able to perceive images produced by light focused at the fovea 260, it is advantageous if incident light is deflected away from the fovea 260 to the PRL 290. Accordingly, such patients can benefit from an IOL that can focus light at the PRL 290 instead of the fovea 260.

For most patients, the PRL 290 is at a distance less than or equal to about 3.0 mm from the fovea 260. Accordingly, the IOL 295 can be configured to deflect incident light by an angle between about 3.0 degrees and up to about 30 degrees such that it is focused at a preferred location within a region at a distance of about 3.0 mm around the fovea 260. The IOL 295 can be customized for a patient by determining the PRL for each patient and then configuring the IOL 295 to deflect incident light such that it is focused at the PRL. The method to find the PRL of any patient is based on perimetry. One perimetry method to locate the PRL is Goldmann Perimetry. The perimetry method to locate the PRL includes measuring the visual field of a patient. For example, the patient can be asked to fixate on a cross and flashes of lights are presented at various parts in the field and the responses are recorded. From the recorded responses, a map of how sensitive the peripheral retina is can be created. The patient can be trained to consistently use the healthy and more sensitive portions of the retina. The perimetry method can be further enhanced by microperimetry, as used by e.g. the Macular Integrity Assessment (MAIA) device, where the retina is tracked in order to place the stimuli consistently and eye movement are accounted for.

Figure 4B:
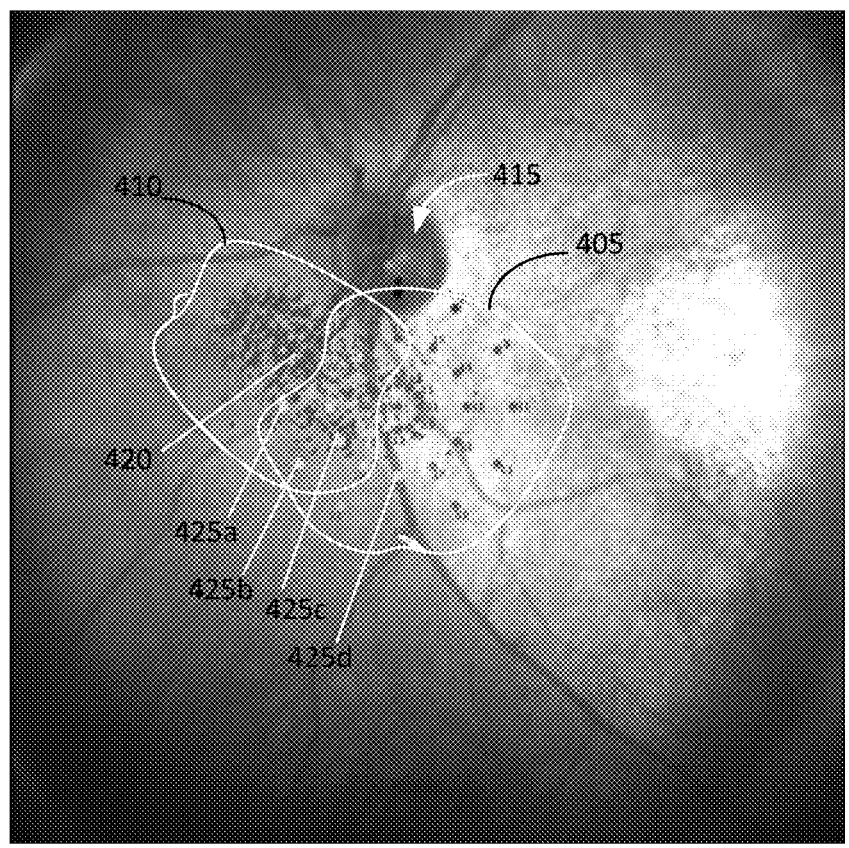
FIG. 4B illustrates an image obtained by a PRL diagnostic device.

The PRL can also be located subjectively, by asking the patient to fixate as they want into an OCT-SLO instrument. The instrument can obtain one or more images of the retina and determining which portions of retina are used more than the other. One method of determining the portions of retina that are used more includes imposing the parts of fixation onto an image of the retina. The OCT-SILO instrument can also be used to obtain normal images of the retina. FIG. 4B illustrates an image obtained using the perimetry method and the fixation method. FIG. 4B shows a photo of the retina with a central scotoma 415. The red-yellow-orange dots in the region marked 405 are the results of the perimetry. Perimetry results indicate that spots closer to the scotoma 415 perform worse that spots farther away from the scotoma 415. The many small teal dots in the region marked 410 are the fixation points, and the lighter teal point 420 is the average of the dots in the region 410. Based on the measurements, the PRL can be located at either point 420 or one some of the yellow points 425a-425d. Accordingly, an IOL 295 can be configured to focus an image at one of the points 420 or 425a-425d. The determination of the PRL for a patient having both cataract and AMD can be made by methods other than the methods described above.

Since, AMD patients rely on their peripheral vision to view objects, their quality of vision can be improved if optical errors in the peripheral vision are identified and corrected. Optical power calculation for an IOL configured for foveal vision is based on measuring eye length and corneal power. However, power calculation for an IOL that focuses objects in an area of the peripheral retina around the fovea can depend on the curvature of the retina as well as the oblique astigmatism and coma that is associated with the oblique incidence of light in addition to the eye length and the corneal power.

Methods that are used by an optometrist to measure optical power for spectacle lenses or contact lenses for non AMD patients with good foveal vision are not practical for measuring optical power for ophthalmic solutions (e.g., IOL, spectacle lenses, contact lenses) for peripheral vision. Optometrists use various machines such as autorefractors, as well as a method called subjective refraction wherein the patient reads lines on the wall chart. The response is then used to gauge which trial lenses to put in, and the lenses that give the best results are used. However, such a method is not practical to determine which ophthalmic solution is best for a patient with AMD who relies on peripheral vision to view objects since, the performance estimates are rendered unreliable by the phenomenon of aliasing (a phenomenon which makes striped shirts look wavy on some television sets with poor resolution), the difficulty of fixation and general fatigue associated with orienting the head/eye to focus objects on the peripheral retina. Instead, the methods used to evaluate the optical power of ophthalmic solutions for AMD patients rely on peripheral wavefront sensors to estimate peripheral optical errors. Peripheral wavefront sensors illuminate a small patch of the PRL using lasers and evaluate how the light reflected and coming out of the eye is shaped through an array of micro-lenses. For example, if the light coming out of the eye is converging, the patient is myopic at the PRL.

In various patients suffering from AMD as well as cataract, the natural lens 240 can be removed and replaced with the IOL 295, or implanted in the eye 200 in addition to another IOL placed previously or at the same time as the IOL 295. In some patients suffering from AMD, the IOL 295 can be implanted in the eye 200 in addition to the natural lens 240. In FIG. 4A-1, the IOL 295 is implanted in the capsular bag. Where possible, the IOL 295 is placed as close to the retina as possible. However, in other implementations, the IOL 295 can be implanted within the capsular bag in front of another IOL or in front of the capsular bag. For example, the IOL 295 can be configured as an iris, sulcus or anterior chamber implant or a corneal implant. By selecting an IOL 295 with appropriate refractive properties, the image quality at the PRL 290 can be improved.

The visual outcome at the PRL is poor as compared to the foveal visual due to a decreased density of ganglion cells at the PRL and/or optical errors and artifacts that arise due to oblique incidence of light (e.g., oblique astigmatism and coma). As discussed above, patients with AMD can receive substantial improvement in their vision when refractive errors at the PRL are corrected. Many of the existing embodiments of IOLs that are configured to improve visual outcome for a patient are not configured to correct for refractive errors in the image generated at the PRL.

Various embodiments of the IOLs disclosed herein are configured to focus light at a location on the peripheral retina to produce good quality images, for example, images produced at the location on the peripheral retina can have a quality that is substantially similar to the quality of images produced at the fovea. The images produced at the location on the peripheral retina by the IOLs disclosed herein can have reduced artifacts from optical effects such as oblique astigmatism, coma or other higher order aberrations. Other embodiments are based on the fact that the location on the peripheral retina is not used in the same way as the fovea. For example, it may be harder to maintain fixation on the PRL, so it may be advantageous to increase the area of the retina where incident light is focused by the IOL in order to have sufficient visual acuity and/or contrast sensitivity even when fixation is not maintained and/or when the eye is moved linearly as in during reading. As such, the retinal area of interest can cover areas where the refraction differs substantially due to differences e.g. in retinal curvature and oblique astigmatism. Various embodiments of IOLs described herein can be used to direct and/or focus light entering the eye along different directions at different locations of the retina. Simulation results and ray diagrams are used to describe the image forming capabilities of the embodiments described herein. To simulate the images formed by various embodiments of IOLs described herein, it is assumed that a central scotoma results in a blackened out middle area and that the rest of the image quality is degraded by average amounts of peripheral refractive errors, astigmatism and coma. Additionally, the limitations imposed by ganglion cells are simulated. Any combination of multi-refraction correction is simulated as well.

As used herein, an IOL refers to an optical component that is implanted into the eye of a patient. The IOL comprises an optic, or clear portion, for focusing light, and may also include one or more haptics that are attached to the optic and serve to position the optic in the eye between the pupil and the retina along an optical axis. In various implementations, the haptic can couple the optic to zonular fibers of the eye. The optic has an anterior surface and a posterior surface, each of which can have a particular shape that contributes to the refractive properties of the IOL. The optic can be characterized by a shape factor that depends on the radius of curvature of the anterior and posterior surfaces and the refractive index of the material of the optic. The optic can include cylindrical, aspheric, toric, or surfaces with a slope profile configured to redirect light away from the optical axis and/or a tight focus.

It is envisioned that the solution herein can be applied to any eccentricity. For example, in some patients, a location that is disposed at a small angle from the fovea can be used as the PRL while in some other patients, a location that is disposed at an angle of about 30 degrees from the fovea can be used as the PRL. This is further explained below with reference to FIG. 5D which shows a cross-section view of an eye with a central scotoma at the fovea 260 and implanted with an implementation of an IOL 500. The IOL 500 can including an optic have an anterior surface configured to receive incident light from an object 516 and a posterior surface configured to redirect light out of the IOL towards a preferred retinal location (PRL) 520 on the retina. As discussed above the PRL 520 can be disposed at an angle with respect to an optical axis 280 of the eye. In various implementations, the angle θ that the PRL 2610 makes with the optical axis 280 can vary between a small angle (e.g., 2-5 degrees) and about 45-60 degrees.

Additionally, various implementations of optics disclosed herein that are configured to improve contrast sensitivity at the PRL can be combined with a diagnostics system that identifies the best potential PRL after correction of refractive errors. Normally, optical errors can restrict the patient from employing the best PRL, making them prefer neurally worse but optically better region. Since various implementations of optics disclosed herein can correct optical errors at the PRL, it may be advantageous to find the best PRL for the patient with a method that is not degraded by optical errors (e.g. adaptive optics). Various implementations of optics disclosed herein can be designed by taking advantage of the symmetries that exists with regards to peripheral refractive errors in many patients.

Symmetric Lens to Generate an Image at a Location of the Peripheral Retina for AMD Patients Patients with AMD who do not have a well-developed PRL could potentially be provided with a symmetric lens that is configured to focus light incident at different oblique angles with respect to the optical axis 280 of the eye of the patient to their corresponding location of the peripheral retina. The lens can be symmetric about an optical axis of the lens such that the image quality in a region around the optical axis is uniform. The lens could also be configured to correct errors resulting from oblique incidence of light such as oblique astigmatism and/or peripheral coma for every direction.

Figure 5A:
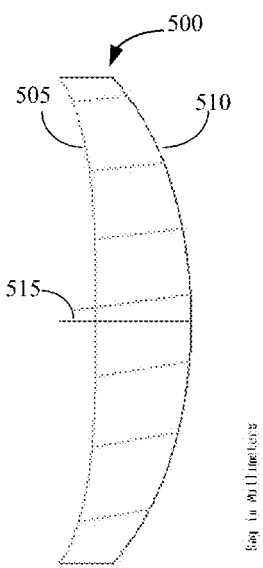
FIG. 5A illustrates an implementation of an optic including at least one aspheric surface that can improve the visual outcome for a patient with AMD.

FIG. 5A illustrates an implementation of an optic 500 that that is configured to focus light incident at oblique angles with respect to the optical axis 280 of the eye of the patient at a location of the peripheral retina. The optic 500 has a first surface 505 and a second surface 510. An optical axis 515 passes through the geometric center of the optic 500 and joins the center of curvatures of the first and second surfaces. The optic 500 illustrated in FIG. 5A is symmetric about the optical axis 515 such that the image quality in a region around the optical axis is uniform. This disclosure also includes implementations of an optic that can be configured to be asymmetric about an optical axis of the optic 500 such that the image quality in a particular location with respect to the optical axis is better than the image quality at a different location.

The optic 500 can be included in an intraocular lens (IOL) that can be implanted in the eye of a patient. For example, the optic 500 can be included in an IOL that is configured to be inserted between the pupil/iris of the patient and the capsular bag (e.g., in the sulcus of the eye). As another example, the optic 500 can be included in an IOL that is configured to be implanted in the capsular bag of the patient's eye. The IOL including the optic 500 can be implanted in the patient's eye such that the optical axis 515 of the optic 500 is coincident with the optical axis 280 of the patient's eye. The IOL including the optic 500 can be implanted in the patient's eye such that the optical axis 515 of the optic 500 is offset and/or tilted with respect to the optical axis 280 of the patient's eye. When implanted, the first surface 505 can face the cornea of the patient's eye and the second surface 510 can face the retina. Accordingly, in various implementations, the first surface 505 can be referred to as the anterior surface and the second surface 510 can be referred to as the posterior surface. Alternately, when implanted the first surface 505 can face the retina of the patient's eye and the second surface 510 can face the cornea. The thickness of the optic 500 along the optical axis 515 can be less than 1.5 mm. For example, the thickness of the optic along the optical axis can vary between about 0.25 mm and about 0.4 mm, about 0.3 mm and about 0.5 mm, about 0.4 mm and about 0.6 mm, about 0.5 mm and about 0.7 mm, about 0.6 mm and about 0.8 mm, about 0.7 mm and about 0.9 mm, 0.9 mm and about 1.0 mm, about 0.95 mm and about 1.25 mm, about 1.2 mm and about 1.5 mm or values therebetween.

The first surface 505 and/or the second surface 510 can be spheric, aspheric, conic, etc. The first surface 505 and/or the second surface 510 can be described mathematically by a polynomial function in either Cartesian or polar coordinates.

For example, the first surface 505 and/or the second surface 510 can be described mathematically by equation (1) below:

$$z = \frac{cr^2}{1 + \sqrt{1-(1+k)c^2r^2}} + \sum_{i=1}^{6} \alpha_i r^{2i} \quad (1)$$

where z is the sag of the surface, c is the curvature of the surface, r the radial distance from the optical axis 515, k the conic constant and $\alpha_1$, $\alpha_2$, $\alpha_3$, $\alpha_4$, $\alpha_5$, and $\alpha_6$, the aspheric coefficients. Without any loss of generality, the curvature of the surface can be correlated to the inverse of the radius of curvature R. The surface described by equation (1) above is symmetric about the optical axis and thus does not have any angular dependency. Accordingly, the optical effect (and/or image quality) is independent of angular location.

When the aspheric coefficients are zero, the first surface 505 and/or the second surface 510 can be considered to be a conic. Since each of the first surface 505 and the second surface 510 surface can be described by eight (8) parameters including the curvature c, the conic constant k and the six aspheric coefficients $\alpha_1$, $\alpha_2$, $\alpha_3$, $\alpha_4$, $\alpha_5$, and $\alpha_6$, fourteen (14) degrees of freedom are available when designing the lens. This allows sufficient flexibility to achieve correction of peripheral optical errors at any location on the peripheral retina including a specific location on the peripheral retina (e.g., the PRL).

The values of the surface parameters such as radius of curvature, aspheric coefficients, conic constant, etc. can be different for the first surface 505 and the second surface 510 of the optic 500 can be different. For example, the surface that faces the cornea can have a high conic constant (e.g., between 10 and 1000) and the surface that faces the retina can have a low conic constant (e.g., between 0 and 10). The curvature of the posterior surface of the optic 500 that faces the retina can be higher than the curvature of the anterior surface that faces the cornea. For example, the anterior surface can be flat or close to flat in some implementations. Accordingly, the optic 500 can have a meniscus shape such that vertex of the optic 500 is curved inwards from the edge of the optic 500.

In various implementations, the radius of curvature of the first and the second surface of the optic 500 be between about −4 mm and flat. The conic constant of the first and the second surface of the optic 500 can have a value between 0 and 1000. The aspheric coefficient $\alpha_1$ can have a value between about −10E-03 and 10E-03. The aspheric coefficient $\alpha_2$ can have a value between about −5E-03 and 5E-03. The aspheric coefficient $\alpha_3$ can have a value between about −10E-04 and about 10E-04. The aspheric coefficient $\alpha_4$ can have a value between about −10E-05 and about 10E-05. The aspheric coefficient $\alpha_5$ can have a value between about −5E-05 and about 5E-05. The aspheric coefficient $\alpha_6$ can have a value between about −10E-07 and about 10E-07.

One method of determining the first surface 505 and the second surface 510 of the optic 500 includes selecting values for the six parameters that describe the first surface 505 and the second surface 510 that reduces or minimizes one or more optical errors (or increases or maximizes one or more figures of merit) at a desired location of the peripheral retinal for one or more angles of incidence. Since, the available degrees of freedom are large (e.g., 12 or 14), it is possible that a local minima for the optical errors is achieved by the determined surface profile instead of the absolute minima. Thus, the determined surface may not be the optimal surface. The process of determining the surface profile that provides the most reduction in optical errors at a desired location of the peripheral retinal for one or more angles of incidence can be improved by choosing appropriate starting values for the different parameters and an appropriate figure of merit to characterize the optical performance. Some possible figures of merit that effectively characterize the optical performance of the optic for patients with AMD can include modulus of the optical transfer function (MTF). The MTF for the optic 500 can be calculated for both sagittal rays and tangential rays originating from an object disposed with respect to the intersection of the optic and the optical axis of the eye. Accordingly, two MTF curves are calculated one for sagittal rays and the other for tangential rays. For an image to have good quality and sufficient contrast sensitivity, the MTF for both the tangential rays and the sagittal rays should be above a threshold. The MTF is calculated for various off-axis positions of the object represented by coordinates along the x-direction and the y-direction in a Cartesian coordinate system in which the point of intersection of the optic and the optical axis of the eye is disposed at the origin of the Cartesian coordinate system and the optical axis is along the z-direction. In various implementations, the point of intersection of the optic and the optical axis of the eye can coincide with the geometric of the optic and/or the geometric center of a surface of the optic.

The MTF of the optic refers to how much of the contrast ratio in the object is preserved when the object is imaged by the optic. A MTF value of 1.0 indicates that the optic does not degrade the contrast ratio of the object and a MTF value of 0 indicates that the contrast ratio is degraded such that adjacent lines in the object cannot be resolved when the object is imaged by the optic. Accordingly, MTF is a measure of contrast sensitivity or sharpness. Another figure of merit can include average MTF for a range of retinal locations and eccentricities, either close to a single PRL or for multiple PRLs for the patient, and with spatial frequencies chosen to match the retinal sampling. Other figures of merit can include area under the MTF curve for different spatial frequencies, average MTF for a range of spatial frequencies or combinations of the figures of merit listed here.

Appropriate starting values of curvature include values of curvature that provide increased on-axis refractive correction. Appropriate starting values of aspheric coefficients $\alpha_1$, $\alpha_2$, $\alpha_3$, $\alpha_4$, $\alpha_5$, and $\alpha_6$ can be chosen from Seidel theory so as to minimize (or substantially reduce) oblique astigmatism and coma through interaction with the distance between IOL and pupil.

One method of determining the optic that provides the best performance at a desired location of the peripheral retinal for one or more angles of incidence can include starting from an optic that is meniscus shaped and then optimizing the different parameters described above for the two surfaces to improve one or more figures of merit (e.g., improve the peripheral MTF). The optimization process can be done on an electronic processor (e.g., a computer, a computing device, etc.) using simulation programs such as OSLO, ZEMAX, CODE V, or a proprietary simulator. The figures of merit can be appropriately weighted to include and/or emphasize the peripheral region at a distance equal to the distance between the PRL and the fovea. In some implementations, the figures of merit can exclude image quality at the fovea to further improve peripheral quality. In some implementations, the figures of merit can include image quality at the fovea as well as at a particular location of the peripheral retina and/or a region around the fovea. As discussed below, the first and the second surfaces 505 and 510 of the optic 500 can be selected using an eye model that is based on population average values for various parameters of the eye. Alternately, the first and the second surfaces 505 and 510 of the optic 500 can be selected using an eye model that is specific to a patient. Some of the patient's eye characteristics that can be taken into consideration to determine first and the second surfaces 505 and 510 of the optic 500 can include: (i) Corneal radius of curvature and asphericity; (ii) Axial length; (iii) Retinal curvature; (iv) Anterior chamber depth; and/or (v) Expected lens position.

An advantage of an optic including first and second surfaces having surface characteristic described above is that once the characteristics of the first and second surfaces have been determined, the optic can be fabricated as a single optical component with uniform refractive index. Additionally, the symmetrical nature of the optic can confer a number of advantages in the diagnostics and surgery procedure as discussed below. For example, as discussed above, a patient who does not have a well-established PRL can benefit from a lens including an optic similar to optic 500 described above since the patient can choose the orientation and the eccentricity that provides the best visual outcome. The optic 500 can improve the peripheral optical quality generally for a patient without a well-established PRL at a position that provides the best visual outcome for the patient so that the patient can develop the PRL at that position. Some of the lenses that are configured for use by patients with AMD can degrade quality of vision at the fovea. However, as discussed below, the optic 500 can be configured to provide good image quality at the fovea as well as a location of the peripheral retina. So it may be attractive to consider an optic similar to the optic 500 above for a patient with beginning AMD, where some other implementations of lenses that configured to improve image quality at a peripheral retina location may degrade foveal image quality to unacceptable levels. Since the onset of AMD is generally later than cataract, there may be a large group of patients undergoing cataract surgery who have early signs of AMD, and thus later would benefit from a lens including an optic similar to optic 500 and for whom the on-axis performance (foveal image quality) of the alternative lens configuration would be unacceptable. Additionally, the surgeon does not need to orient an IOL including an optic similar to the optic 500 when implanting it. Furthermore, the optic 500 can be configured to have a thickness that can provide manufacturing benefits as compared to other lens designs. Additionally, the surfaces of the optic 500 can be configured to be devoid of tilt which can also provide manufacturing benefits.

Figure 5B:
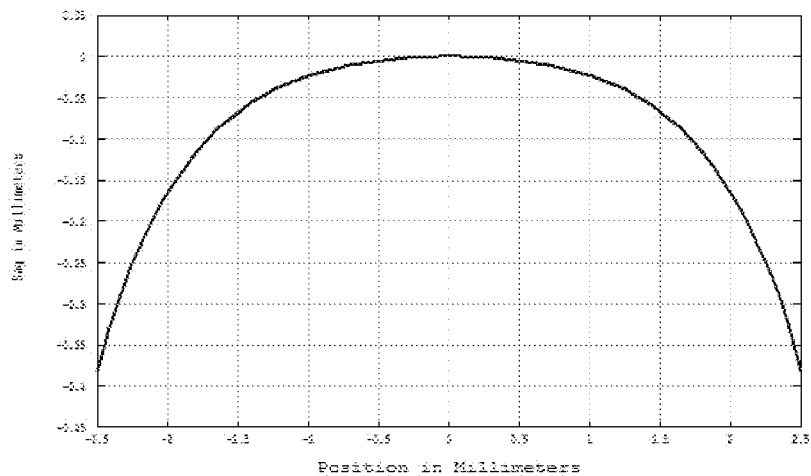
FIG. 5B illustrates the surface profile of the aspheric surface of the lens illustrated in FIG. 5A in a first meridian.
Figure 5C:
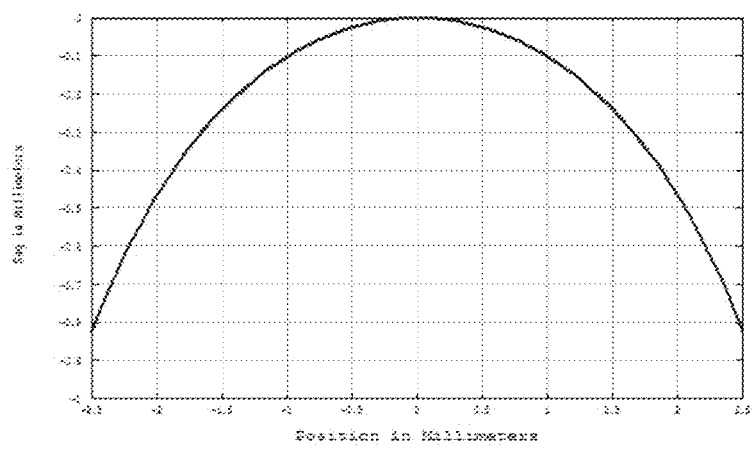
FIG. 5C illustrates the surface profile of the aspheric surface of the lens illustrated in FIG. 5A in a second meridian.

As discussed above, the surface sag of the first surface 505 and/or the second surface 510 can be varied by selecting different values of the curvature, conic constant, and other parameters in equation (1). FIG. 5B illustrates the surface sag of the first surface 505 for an implementation of the optic 500 and FIG. 5C illustrates the surface sag of the second surface 510 for the implementations of the optic 500. It is noted that from FIGS. 5B and 5C that the first and second surface 505 and 510 are aspheric.

Depending on the patient's refractive needs, the first surface 505 and/or the second surface 510 of the optic 500 can be convex or concave. For example, in the illustrated implementation, both the first surface 505 and the second surface 510 are convex. However, in other implementations, the first surface 505 can be concave and/or the second surface 510 can be concave. The shape and curvature of the first surface 505 and/or second surface 510 can be selected based on the patient's visual requirements as well the patient's ocular characteristics.

In various implementations, the optic 500 can be configured such that the refractive properties of the optic 500 can be changed in response to the eye's natural process of accommodation. For example, the optic 500 can comprise a deformable material that can compress or expand in response to ocular forces applied by the capsular bag and/or the ciliary muscles. For example, the optic 500 can be configured to change their shape in response to ocular forces in the range between about 1 gram to about 10 grams, 5 to 10 grams, 1 to 5 grams, about 1 to 3 grams or values therebetween to provide an optical power change between about 0.5 Diopters and about 6.0 Diopters. In various implementations, the optic 500 can comprise materials such as acrylic, silicone, polymethylmethacrylate (PMMA), block copolymers of styrene-ethylene-butylene-styrene (C-FLEX) or other styrene-base copolymers, polyvinyl alcohol (PVA), polystyrenes, polyurethanes, hydrogels, etc. The optic 500 can comprise structures and materials that are described in U.S. Publication No. 2013/0013060 which is incorporated by reference herein in its entirety.

As discussed above, the optic 500 can be incorporated in an IOL that is provided with a haptic that holds the IOL in place when implanted in the eye. The haptic can comprise a biocompatible material that is suitable to engage the capsular bag of the eye, the iris 230, the sulcus and/or the ciliary muscles of the eye. For example, the haptic can comprise materials such as acrylic, silicone, polymethylmethacrylate (PMMA), block copolymers of styrene-ethylene-butylene-styrene (C-FLEX) or other styrene-base copolymers, polyvinyl alcohol (PVA), polystyrene, polyurethanes, hydrogels, etc. In various implementations, the haptic can include a one or more arms that are coupled to the optic 500. For example, the haptic can be configured to have a structure similar to the structure of the biasing elements disclosed in U.S. Publication No. 2013/0013060 which is incorporated by reference herein in its entirety. In various implementations, the haptic can include one or more arms that protrude into the optic 500. In various implementations, the haptic can be configured to move the optic 500 along the optical axis of the eye in response to ocular forces applied by the capsular bag and/or the ciliary muscles. For example, the haptic can include one or more hinges to facilitate axial movement of the optic. As another example, the haptic can include springs or be configured to be spring-like to effect movement of the optic 500. In this manner, the axial position of the optic 500 can be varied in response to ocular forces to provide vision over a wide range of distances. An IOL that is configured to change the axial position of the optic and/or shape and size of the optic in response to ocular forces applied by the capsular bag and/or ciliary muscles can be referred to as an accommodating lens.

The optic 500 is configured such that light incident on the cornea at oblique angles to the optical axis 280 of the eye is focused on a location of the peripheral retina away from the fovea. The light can be incident in the vertical field of view or the horizontal field of view. For example, the optic 500 can be configured to focus light incident at oblique angles between about 5 degrees and about 30 degrees with respect to the optical axis 280 of the eye, between about 10 degrees and about 25 degrees with respect to the optical axis 280 of the eye, between about 15 degrees and about 20 degrees with respect to the optical axis 280 of the eye, or there between at a location on the peripheral retina away from the fovea. As discussed above, the optic 500 can also be configured such that light incident on cornea along a direction parallel to the optical axis is focused on the fovea for those patients with early AMD who still have some foveal vision. For example, some patients may have parts of the fovea covered by a scotoma instead of a central scotoma. Such patients may have some residual foveal vision and can benefit from incident light being focused at the fovea by the optic 500. Additionally, the optic 500 can also be configured to accommodate to focus objects located at different distances on to the retina (e.g., at a location on the periphery of the retina and/or the fovea) in response to ocular forces exerted by the capsular bag and/or ciliary muscles.

The implementations of the optic 500 described in this disclosure can be configured to correct lower order errors (e.g. sphere and cylinder), higher order aberrations (e.g., coma, trefoil) or both resulting from the oblique incidence of light in the image formed at a location of the peripheral retina. The characteristic of the first surface 505 and/or the second surface 510 of the optic 500, the thickness of the optic 500, etc. can be designed such that the optic 500 can focus light incident at a plurality of oblique angles (e.g., between about −25 degree and about +25 degrees with respect to the optical axis of the eye) in an area around a location on the peripheral retina spaced away from the fovea with sufficient visual contrast. This is explained in further detail below with respect to FIG. 5D.

Figure 5D:
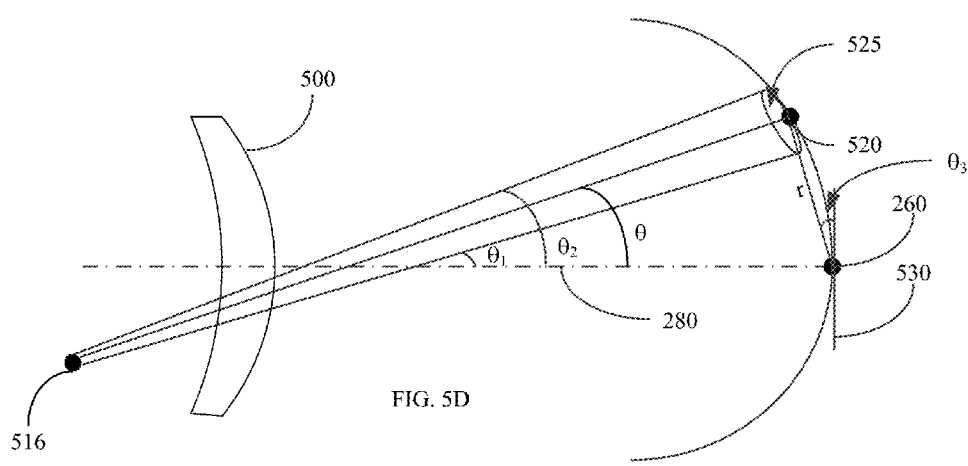
FIG. 5D shows a cross-section view of an eye with a central scotoma at the fovea and implanted with an implementation of an IOL including the optic illustrated in FIG. 5A.
Figures 1, 5D:
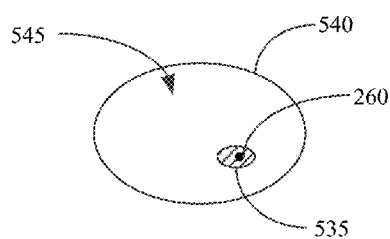
Figures 2, 5D:
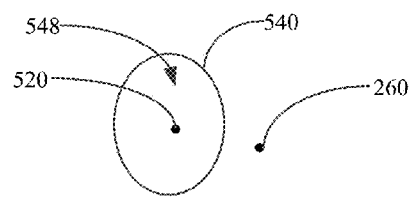

FIG. 5D shows a cross-section view of an eye with a central scotoma at the fovea 260 and implanted with an implementation of an IOL including the optic 500 illustrated in FIG. 5A. Light from an object is incident in a range of oblique angles between $\theta_1$ and $\theta_2$ with respect to the optical axis 280 and are focused by the optic 500 in an area 525 disposed around a location 520 on the peripheral retina disposed away from the fovea 260. For most patients $\theta_1$ can be between 3 degrees and 5 degrees and $\theta_2$ can be between 10 degrees and 35 degrees. The location 520 can be located at a distance r from the fovea 260 along a direction that makes an angle $\theta_3$ with respect to a tangential line 530 intersecting the retina at the fovea 260 and lying in the tangential plane. Although, not shown in FIG. 5D, the location 520 can be located at a distance r from the fovea 260 along a direction that makes an angle $\theta_4$ with respect to a tangential line (not shown) intersecting the retina at the fovea 260 and lying in the sagittal plane. The angles $\theta_3$ and $\theta_4$ can have a value greater than or equal to 0 degrees and less than 30 degrees. The distance r can have a value between about 0.5 mm and about 4 mm.

Figures 3, 5D:
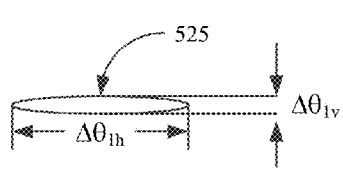

The area 525 can be described as the region between a first region which is the base of a cone having a semi angle of $\theta_1$ degrees with respect to the optical axis 280 and a second region which is the base of a cone having a semi angle of about $\theta_2$ degrees with respect to the optical axis 280. Accordingly, the angular width of the area 525 is given by $(\theta_2-\theta_1)$. For most patients, the angular width of the area 525 can be between about 5 degrees and about 30 degrees. Without any loss of generality, the area 525 can include locations that are within about 2-5 mm from the fovea 260. The area 525 can have an angular extent $\Delta\theta_{1h}$ in the horizontal plane and an angular extent $\Delta\theta_{1v}$ in the vertical plane, as shown in FIG. 5D-3. In various implementations, the angular extent $\Delta\theta_{1v}$ can be zero or substantially small such that the area 525 is a horizontal line above or below the fovea 260. Alternately, the angular extent $\Delta\theta_{1h}$ can be zero or substantially small such that the area 525 is a vertical line to the left or the right of the fovea 260. In some embodiments, the angular extent $\Delta\theta_{1v}$ and the angular extent $\Delta\theta_{1h}$ can be equal such that the area 525 is circular. In some other implementations, the angular extent $\Delta\theta_{1h}$ and the angular extent $\Delta\theta_{1v}$ can be unequal such that the area 525 is elliptical. In various implementations, the angular extent $\Delta\theta_{1v}$ and the angular extent $\Delta\theta_{1h}$ have values such that the area 525 includes the fovea 260. However, in other implementations, the angular extent $\Delta\theta_{1v}$ and the angular extent $\Delta\theta_{1h}$ can have values such that the area 525 does not include the fovea 260.

In various implementations, the optic 500 can be configured to focus incident light at the PRL 520. However, in various implementations, the IOL 500 can be configured to focus the incident light in front of or behind the PRL 520 such that the incident light is defocused at the PRL 520 as shown in 3J.

As discussed above, the optic 500 is symmetric such that the image quality in an annular region around the fovea is uniform. Such an optic can be used by patients who do not have a well-developed PRL. Such patients can orient their eyes and/or heads to select the position that affords the best visual quality. The annular region can be between a first region and a second region. The first region can be the base of a cone having a semi angle of $\theta_1$ degrees with respect to the optical axis 280 and the second region can be the base of a cone having a semi angle of about $\theta_2$ degrees with respect to the optical axis 280. Accordingly, the angular width of the annular region is given by $(\theta_2-\theta_1)$. For most patients $\theta_1$ can be between 3 degrees and 5 degrees and $\theta_2$ can be between 10 degrees and 35 degrees. Accordingly, for most patients, the angular width of the annular region can be between about 5 degrees and about 30 degrees. Without any loss of generality, the annular region can include locations that are within about 2-5 mm from the fovea.

Generally, patients with AMD experience greater improvement in their vision when refractive errors arising from the oblique astigmatism and coma are corrected for image formed at a location in the peripheral retina than patients without AMD at similar retinal eccentricities. Accordingly, the characteristics of the first surface 505, the second surface 510, the thickness of the optic 500 and its orientation when implanted in the eye can be adjusted such that the refractive errors due to relative peripheral defocus, oblique astigmatism and coma in an image produced at a location of the peripheral retina by the optic 500 are reduced. The optic 500 can also be configured to provide good visual quality at the fovea 260 for those patients who have early stage AMD.

In contrast to optics and IOLs that are configured to improve image quality at the fovea, the optic 500 is configured to improve image quality in a region of the peripheral retina that is offset from the fovea. For example, the optic 500 can be configured to improve image quality in an annular zone surrounding the fovea 260 as shown in FIG. 5D-1. The annular zone can include an area 545 between an inner periphery 535 surrounding the fovea and an outer periphery 540 surrounding the fovea 260. The inner periphery 535 can include retinal locations at an eccentricity between about 1 degree and about 10 degrees. Without any loss of generality, as used herein, the term eccentricity refers to the angle between a normal to the retina at the location of interest and the optical axis of the eye which intersects the retina at the fovea. Accordingly, the fovea is considered to have an eccentricity of about 0 degrees. The outer periphery 540 can include retinal locations at an eccentricity between about 3 degrees and about 25 degrees. Although in FIG. 5D-1 the optic 500 is not configured to improve image quality in the foveal region, in various implementations, the area 545 in which the optic 500 is configured to improve image quality can extend to the foveal region and include the fovea 260 for patient who have residual foveal vision. In such implementations, the optic 500 can be configured to provide good image quality at the fovea as well as at peripheral retinal locations at an eccentricity between about 1 degree and about 25 degrees. In various implementations, the region 545 can be symmetric about the fovea 260. In some implementations, a projection of the region 545 on a plane tangential to the retina at the fovea 260 can be circular, oval or any other shape.

As another example, the optic 500 can be configured to improve image quality in a region 548 surrounding a preferred retinal location (e.g., location 520 as shown in FIG. 5D) offset from the fovea as shown in FIG. 5D-2. The preferred retinal location can be located at an eccentricity between about 1 degree and about 25 degrees. The region 548 surrounding the preferred retinal location 520 can include retinal locations at an eccentricity between about 1 degree and about 25 degrees.

As discussed above, the image quality at the region of the peripheral retina can be improved by optimizing the image quality produced by the optic 500 such that optical errors (e.g., peripheral astigmatism, coma, trefoil, etc.) are reduced at the peripheral retinal region. For example, the image quality at the peripheral retinal region can be increased by correcting optical errors at the peripheral retinal region, correcting for corneal astigmatism at the peripheral retinal region, reducing optical errors resulting from oblique astigmatism at the peripheral retinal region, reducing coma at the peripheral retinal region and/or reducing other higher order aberrations at the peripheral retinal region.

The improvement in the image quality at the peripheral retinal region provided by the optic 500 can be measured using different figures of merit discussed above. For example, an optic (e.g., the optic 500) that is configured to improve image quality in the peripheral retinal region can provide a MTF greater than a threshold value ($MTF_{THR}$) at one or more spatial frequencies for an image produced at the desired peripheral retinal region. Similarly, an optic that is configured to improve image quality in the foveal region can provide a MTF greater than a threshold value ($MTF_{THR}$) at one or more spatial frequencies for an image produced at the foveal region. The threshold value ($MTF_{THR}$) can be subjective and be determined based on the patient's needs and ophthalmic condition. For example, some patients may be satisfied with an image quality having a MTF greater than 0.1 for spatial frequencies between 10 cycles/mm and 50 cycles/mm. Some other patients may desire a MTF greater than 0.5 for spatial frequencies between 1 cycle/mm and 100 cycles/mm. Accordingly, the threshold MTF value ($MTF_{THR}$) can vary depending on the lens design and the patient's needs. The increase in MTF value can be correlated with an improvement in the patient's ability to read various lines in an eye chart. For example, without any loss of generality, an increase in MTF from 0.7 to 0.8 can correspond to about 15% contrast sensitivity improvement, or 1 line of visual acuity (VA). Similarly, an increase in MTF from 0.7 to 0.9 can correspond to about 30% increase in contrast sensitivity or 2 lines VA.

Figure 5E:
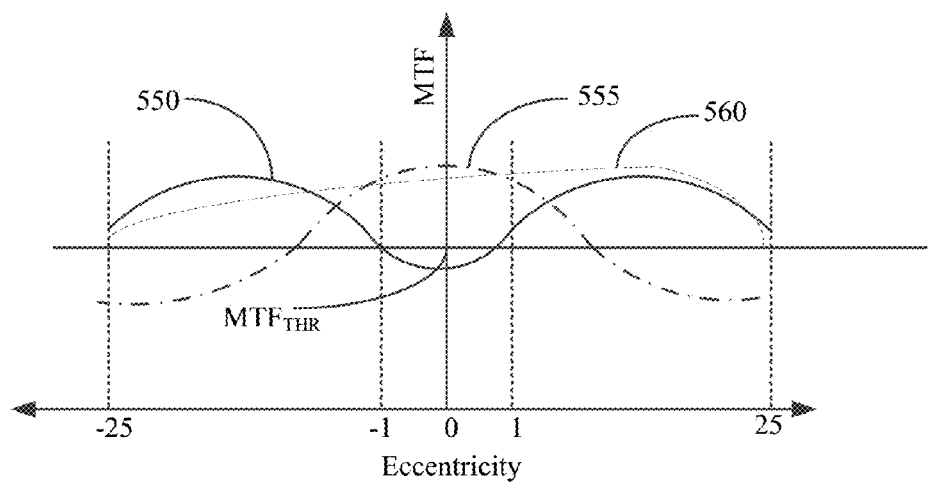
FIG. 5E graphically illustrates the variation in image quality versus eccentricity for an implementation of an optic configured to improve image quality at a peripheral retinal location and an optic configured to improve image quality at the fovea.

FIG. 5E which shows the variation in image quality versus eccentricity for an implementation of an optic configured to improve image quality at a peripheral retinal region and an optic configured to improve image quality at the fovea region. Curve 550 shows the variation of MTF versus eccentricity for an optic configured to improve image quality at a peripheral retinal region while curve 555 shows the variation of MTF versus eccentricity for an optic configured to improve image quality at the foveal region. As shown in FIG. 5E the optic configured to improve image quality at a peripheral retinal region provides a MTF greater than a threshold value ($MTF_{THR}$) at one or more spatial frequencies at an eccentricity between 1 degree and 25 degrees and −1 degree and −25 degrees such that an image produced in the peripheral retinal region at an eccentricity between 1 degree and 25 degrees and −1 degree and −25 degrees has sufficient contrast sensitivity. In various implementations, the optic may be configured to improve image quality at a peripheral retinal region at the expense of foveal vision. For example, the optic configured to improve image quality at a peripheral retinal region may provide a MTF less than the threshold value ($MTF_{THR}$) in the foveal region (e.g., at an eccentricity between −1 degree and 1 degree). In contrast, an optic configured to improve foveal vision will provide an MTF greater than the threshold value ($MTF_{THR}$) for an image produced in the foveal region. In some implementations, the optic configured to improve image quality at a peripheral retinal region may also be configured to provide a MTF value greater than the threshold value ($MTF_{THR}$) at the foveal region as shown by curve 560.

One way to configure the optic 500 to reduce optical errors at a peripheral retinal region is to determine the surface profiles of the optic 500 that reduce optical errors due to oblique astigmatism and coma at the peripheral retinal region when light incident on the eye obliquely with respect to the optical axis 280 is focused by the IOL system 500 at the peripheral retinal region. Using a lens designing system various surface characteristics of the first and/or second surface 505 and 510 of the optic 500 can be determined that reduce optical errors at a peripheral location of the retina. The various surface characteristics can include curvatures, surface sags, radius of curvatures, conic constant, axial thickness, area of the optical zone, diffractive features, echellettes and/or prismatic features provided with the optic, etc. In various implementations, a portion of the first surface or the second surface can include redirecting elements described herein and that are similar to the prismatic features and/or diffractive features described in U.S. Provisional Application No. 61/950,757, filed on Mar. 10, 2014, titled "INTRAOCULAR LENS THAT IMPROVES OVERALL VISION WHERE THERE IS A LOSS OF CENTRAL VISION," which is incorporated by reference herein in its entirety. The redirecting elements can be configured to redirect light incident on the eye along the optical axis and/or at an angle to the optical axis to one or more locations on the retina.

The surface characteristics can be determined using an eye model that is based on average population statistics. Alternately, the surface characteristics can be determined by using an eye model that is specific to each patient and constructed using a patient's individual ocular characteristics. Some of the ocular characteristics that can be taken into consideration when determining the characteristics of the surfaces of the optic 500 can include corneal radius of curvature and asphericity, axial length, retinal curvatures, anterior chamber depth, expected lens position, location of image on the peripheral retina, size of the scotoma, optical and physical characteristics of the existing lens, peripheral aberrations, etc. As discussed above, depending on the patient's needs, the first and/or the second surface 505, 510 of the optic 500 can be symmetric and/or include higher (e.g., second, fourth, sixth, eighth) order aspheric terms. The first and/or second surface 505, 510 of the optic 500 can be parabolic, elliptical, a Zernike surface, an aspheric Zernike surface, a toric surface, a biconic Zernike surface, etc.

The optic 500 can be configured to provide an optical power between about 0.5 Diopter and +34.0 Diopter. For example, the optic 500 can be configured to provide an optical power between about 0.5 Diopter and about 5.0 Diopter, between about 1.0 Diopter and 6.0 Diopter, between about 2.0 Diopter and about 7.0 Diopter, between about 3.0 Diopter and 8.0 Diopter, between about 4.0 Diopter and 9.0 Diopter, between about 5.0 Diopter and 10.0 Diopter, between about 10.0 Diopter and about 15.0 Diopter, between about 15.0 Diopter and about 20.0 Diopter, between about 20.0 Diopter and 25.0 Diopter, between about 25.0 Diopter and about 30.0 Diopter and between about 30.0 Diopter and 34.0 Diopter. The optic 500 can be configured to provide cylindrical power between about 0.5 to about 5.0 Diopters to provide astigmatic correction. In various implementations, the optic 500 can be multifocal having multiple optical zones configured to provide a range of add powers between 0.5 Diopter and about 6.0 Diopter. In various implementations, the optic 500 can include filters and/or coatings to absorb short wavelengths that can damage the retina further. For example, in some implementations, the optic 500 can include a blue blocking filter.

Figure 6A:
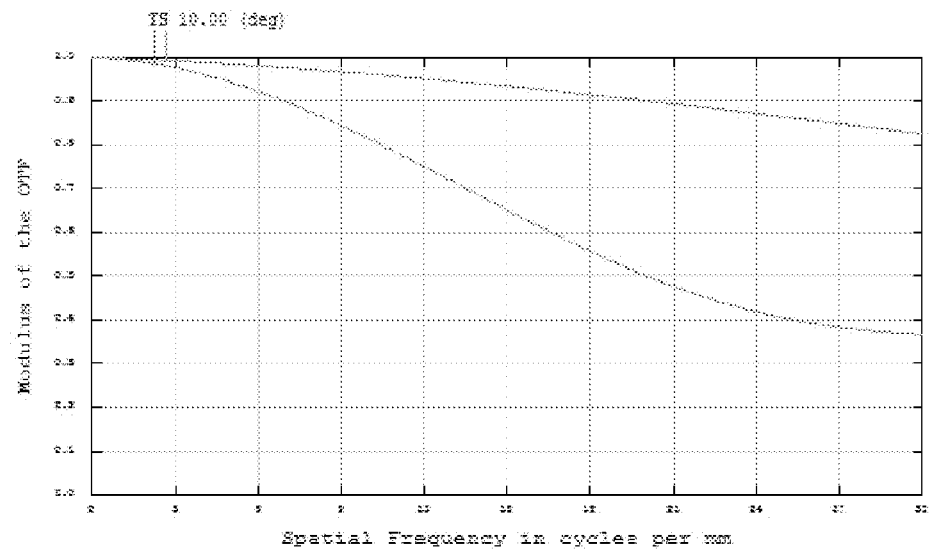
FIG. 6A shows the modulation transfer function for a standard toric IOL that provides good foveal vision at an eccentricity of 10 degrees.
Figure 6B:
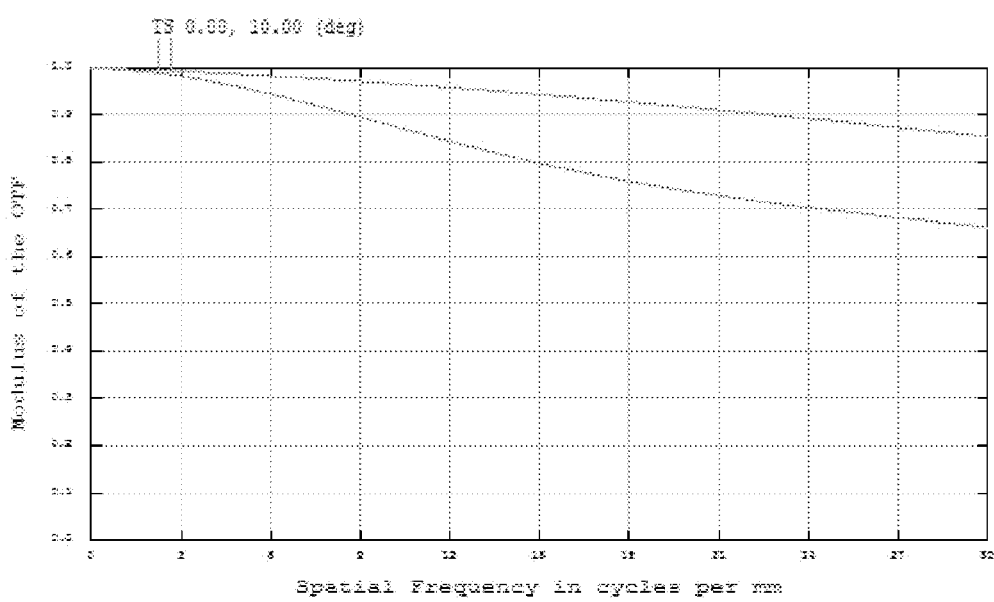
FIG. 6B shows the modulation transfer function provided by an enhanced toric IOL with astigmatic correction at an eccentricity of 10 degrees.
Figure 6C:
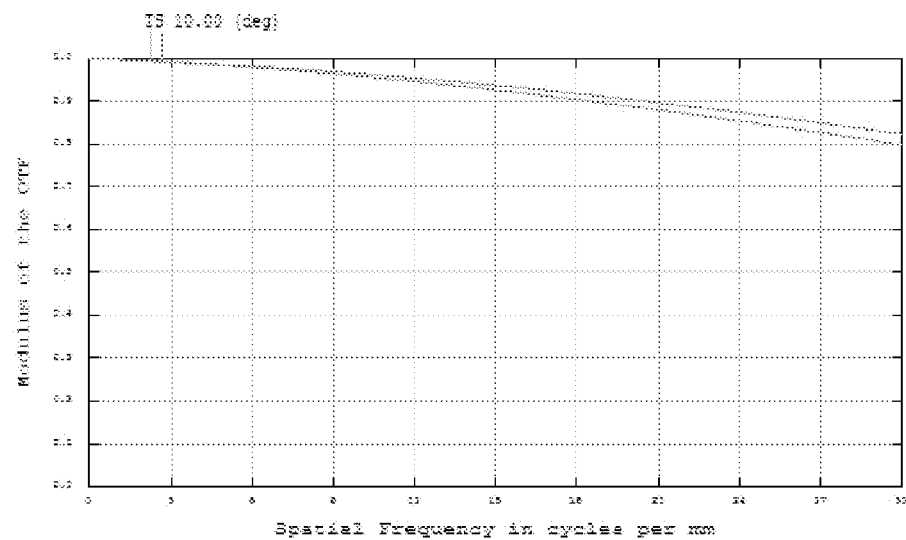
FIG. 6C shows the modulation transfer function provided by the optic illustrated in FIG. 5A at an eccentricity of 10 degrees.

FIG. 6A illustrates the MTF at a PRL located at an eccentricity of 10 degrees for different spatial frequencies between 0 cycles/mm and 30 cycles/mm for a standard toric IOL (e.g., TECNIS®). As discussed above, the MTF is calculated (or simulated) for both sagittal rays and tangential rays. The MTF can be calculated (or simulated) using an optical simulation program such as, for example, OSLO, ZEMAX, CODE V, etc. As observed from FIG. 6A, the MTF at the PRL is less than 0.4 for a spatial frequency of 30 cycles/mm for sagittal focus, while the modulus of the OTF is less than 0.9 for a spatial frequency of 30 cycles/mm for tangential focus. The patient can benefit from increase in the MTF for at least the sagittal focus. FIG. 6B illustrates the MTF at the PRL for different spatial frequencies between 0 cycles/mm and 30 cycles/mm when the patient is implanted with a standard toric IOL that is configured to provide optimal astigmatic correction for the periphery. From FIG. 6B, it is noted that the MTF for both tangential and sagittal foci is improved as compared to a standard toric IOL and is between 0.6 and 0.7 for tangential foci for spatial frequency of 30 cycles/mm and between 0.8 and 0.9 for sagittal foci for spatial frequency of 30 cycles/mm. An optic 500 whose first and second surface can be described by equation (1) provided above can provide a MTF greater than 0.8 for both tangential and sagittal foci for spatial frequency of 30 cycles/mm as observed from FIG. 6C. Accordingly, the optic 500 described above can improve the image quality (e.g., contrast ratio of the image) at peripheral retinal location. In various implementations, the optic 500 can be configured to provide a MTF at a spatial frequency of 30 cycles/mm greater than 0.5, greater than 0.6, greater than 0.7, greater than 0.8, or greater than 0.9. For example, the optic 500 can be configured to provide a MTF at a spatial frequency of 30 cycles/mm greater than 0.5, greater than 0.6, greater than 0.7, greater than 0.8 and greater than 0.9 for eccentricities between about 7 degrees and 13 degrees from the fovea.

Figure 6D:
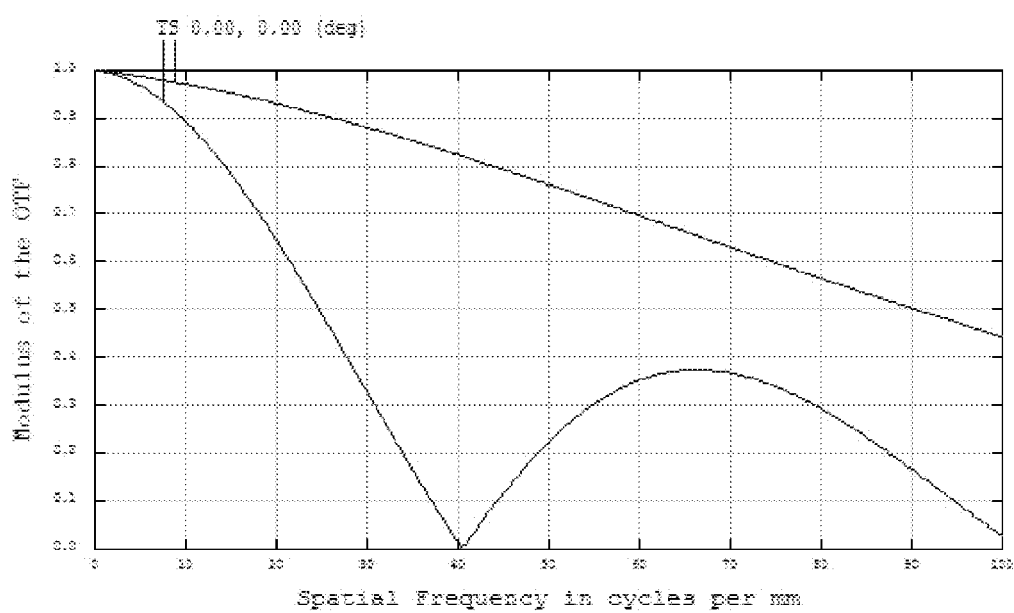
FIG. 6D shows the modulation transfer function provided by the enhanced toric IOL at the fovea.
Figure 6E:
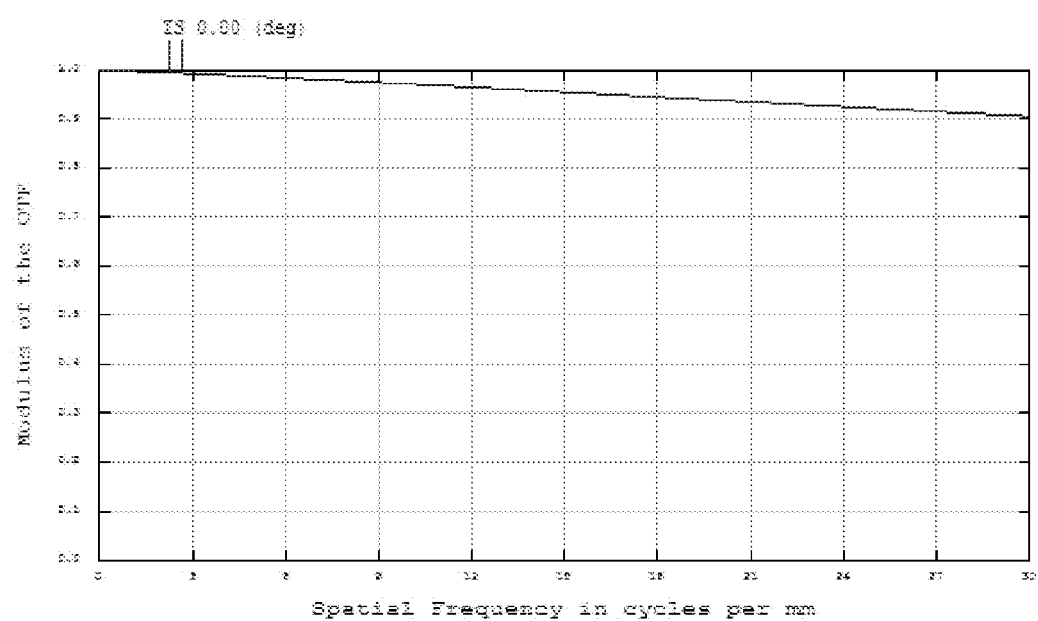
FIG. 6E shows the modulation transfer function provided by the optic illustrated in FIG. 5A at the fovea.

As discussed above, the an implementation of an optic similar to the implementation of optic 500 discussed above having surfaces described by equation (1) above can provide better image quality at the fovea 260 as well as at a peripheral retinal location as compared to another implementation of an optic that is configured to provide good image quality at a peripheral retinal location. FIG. 6D illustrates the MTF at the fovea for different spatial frequencies between 0 cycles/mm and 100 cycles/mm for both tangential and sagittal foci provided by an implementation of a standard toric IOL (e.g., TECNIS®) with optical power optimized for a PRL. FIG. 6E illustrates the MTF at the fovea for different spatial frequencies between 0 cycles/mm and 100 cycles/mm for both tangential and sagittal foci provided by an implementation of an optic similar to the optic 500. It is noted from FIG. 6D the implementation of a standard toric IOL (e.g., TECNIS®) with optical power optimized for a PRL has MTF less than 0.5 for spatial frequencies greater than 30 cycles/mm which indicates degraded contrast sensitivity for image formed at the fovea. In contrast, an optic similar to the optic 500 has a MTF greater than 0.9 for spatial frequencies upto 100 cycles/mm which indicates that an image formed at the fovea has good contrast sensitivity in addition to an image formed at a peripheral retinal location having good contrast sensitivity.

It is conceived that the implementations of optic 500 having two aspheric surfaces that are configured to improve image quality at a peripheral retinal location by correcting optical errors arising from oblique incidence of light (e.g., oblique astigmatism and coma) can improve the MTF by at least 5% (e.g., at least 10% improvement, at least 15% improvement, at least 20% improvement, at least 30% improvement, etc.) at a spatial frequency of 30 cycles/mm for both tangential and sagittal foci at a peripheral retinal location at an eccentricity between about 1 degree and about 25 degrees with respect to the fovea as compared to the MTF at a spatial frequency of 30 cycles/mm provided by an IOL that is configured to improve image quality at the fovea at the same peripheral retinal location.

It is conceived that the implementations of optic 500 having two aspheric surfaces that are configured to improve image quality at a peripheral retinal location by correcting optical errors arising from oblique incidence of light (e.g., oblique astigmatism and coma) can provide a MTF greater than 0.2 at a spatial frequency of 30 cycles/mm for both tangential and sagittal foci, greater than 0.3 at a spatial frequency of 30 cycles/mm for both tangential and sagittal foci, greater than 0.4 at a spatial frequency of 30 cycles/mm for both tangential and sagittal foci, greater than 0.5 at a spatial frequency of 30 cycles/mm for both tangential and sagittal foci, greater than 0.6 at a spatial frequency of 30 cycles/mm for both tangential and sagittal foci, greater than 0.7 at a spatial frequency of 30 cycles/mm for both tangential and sagittal foci, greater than 0.8 at a spatial frequency of 30 cycles/mm for both tangential and sagittal foci or greater than 0.9 at a spatial frequency of 30 cycles/mm for both tangential and sagittal foci at a peripheral retinal location between about 1 degree and about 25 degrees with respect to the fovea.

The optic 500 can be configured to provide one of distance vision, near vision, or intermediate distance vision, distance vision and near vision, distance vision and intermediate distance vision, near vision and intermediate distance vision or all. Various implementations of the optic 500 include spherical aberrations to correct for corneal spherical aberrations. As discussed above, diffractive optical elements can be provided on one of the surfaces (e.g., the spherical surface) of the optic 500 to provide near reading zone or to provide depth of focus. The optic 500 can be configured as an add-on lens that is provided in addition to an existing lens (e.g., a natural lens or another IOL) in the eye. The one or more surfaces of the optic 500 can be designed for different types of patch configurations.

In various implementations, if a patient's cornea is astigmatic (e.g., toric), then the optic 500 described above can be configured as a toric, such that the image quality around the optical axis 515 is uniform. Although, only aspheric coefficients of first to fourth order are included in equation (1) above, the first and second surfaces of the optic 500 can be described aspheric coefficients of higher orders. For example, the first and second surfaces of the optic 500 can be described by an equation including aspheric coefficients of orders upto 14. In other implementations, the first and second surfaces of the optic 500 can be described by aspheric coefficients having order less than 4 (e.g., 1, 2 or 3).

The optic 500 can have a clear aperture. As used herein, the term "clear aperture" means the opening of a lens or optic that restricts the extent of a bundle of light rays from a distant source that can imaged or focused by the lens or optic. The clear aperture can be circular and specified by its diameter. Thus, the clear aperture represents the full extent of the lens or optic usable for forming the conjugate image of an object or for focusing light from a distant point source to a single focus or to a plurality of predetermined foci, in the case of a multifocal optic or lens. It will be appreciated that the term clear aperture does not limit the transmittance of the lens or optic to be at or near 100%, but also includes lenses or optics having a lower transmittance at particular wavelengths or bands of wavelengths at or near the visible range of the electromagnetic radiation spectrum. In some embodiments, the clear aperture has the same or substantially the same diameter as the optic 500. Alternatively, the diameter of the clear aperture may be smaller than the diameter of the optic 500. In various implementations of the optic 500 described herein the clear aperture of the optic 500 can have a dimension between about 3.0 mm and about 7.0 mm. For example, the clear aperture of the optic 500 can be circular having a diameter of about 5.0 mm.

The optic 500 can include prismatic, diffractive elements, echelletes or optical elements with a gradient refractive index (GRIN) profile to provide a larger depth of field or near vision capability. The optic 500 can include one or more apertures in addition to the clear aperture to further enhance peripheral image quality.

The implementations of optic 500 described herein can use additional techniques to extend the depth of focus. For example, the optic 500 can include diffractive features (e.g., optical elements with a GRIN profile, echelletes, etc.) to increase depth of focus. As another example, in some embodiments, a refractive power and/or base curvature profile(s) of an intraocular lens surface(s) may contain additional aspheric terms or an additional conic constant, which may generate a deliberate amount of spherical aberration, rather than correct for spherical aberration. In this manner, light from an object that passes through the cornea and the lens may have a non-zero spherical aberration. Because spherical aberration and defocus are related aberrations, having fourth-order and second-order dependence on radial pupil coordinate, respectively, introduction of one may be used to affect the other. Such aspheric surface may be used to allow the separation between diffraction orders to be modified as compared to when only spherical refractive surfaces and/or spherical diffractive base curvatures are used. An additional number of techniques that increase the depth of focus are described in detail in U.S. patent application. Ser. No. 12/971,506, titled "SINGLE MICROSTRUCTURE LENS, SYSTEMS AND METHODS," filed on Dec. 17, 2010, and incorporated by reference in its entirety herein. In some embodiments, a refractive lens may include one or more surfaces having a pattern of surface deviations that are superimposed on a base curvature (either spherical or aspheric). Examples of such lenses, which may be adapted to provide lenses according to embodiments of the present invention, are disclosed in U.S. Pat. No. 6,126,286, U.S. Pat. No. 6,923,539 and U.S. Patent Application No. 2006/0116763, all of which are herein incorporated by reference in their entirety.

Lens Designs to Improve Peripheral Vision

The lenses described below include implementations of standard lenses, multi-refractive lenses, lenses with asymmetric Zernike surfaces, dual optic lenses, piggyback lenses, etc. that can be configured to focus obliquely incident light at a location on the peripheral retina away from the fovea.

Embodiments of the lenses discussed herein are configured to redirect light incident at angles in a range of angle between about ±30 degrees with respect to the optical axis 280 of the eye at a location on the peripheral retina away from the fovea. For example, the implementations of the lenses discussed herein can be configured to focus light incident at an angle between ±10 degrees with respect to the optical axis 280 in a vertical plane with a contrast sensitivity of at least 0.5 for a spatial frequency of 30 cycles/mm. As another example, the implementations of the lenses discussed herein can be configured to focus light incident at an angle between ±25 degrees with respect to the optical axis 280 in a horizontal plane with a contrast sensitivity of at least 0.5 for a spatial frequency of 30 cycles/mm. As discussed above, the MTF refers to how much of the contrast ratio in the object is preserved when the object is imaged by the lens. A modulus of the OTF of 1.0 indicates that the IOL does not degrade the contrast ratio of the object and modulus of the OTF of 0 indicates that the contrast ratio is degraded such that adjacent lines in the object cannot be resolved when the object is imaged by the lens. Accordingly, the MTF is a measure of contrast sensitivity or sharpness.

Figure 5F:
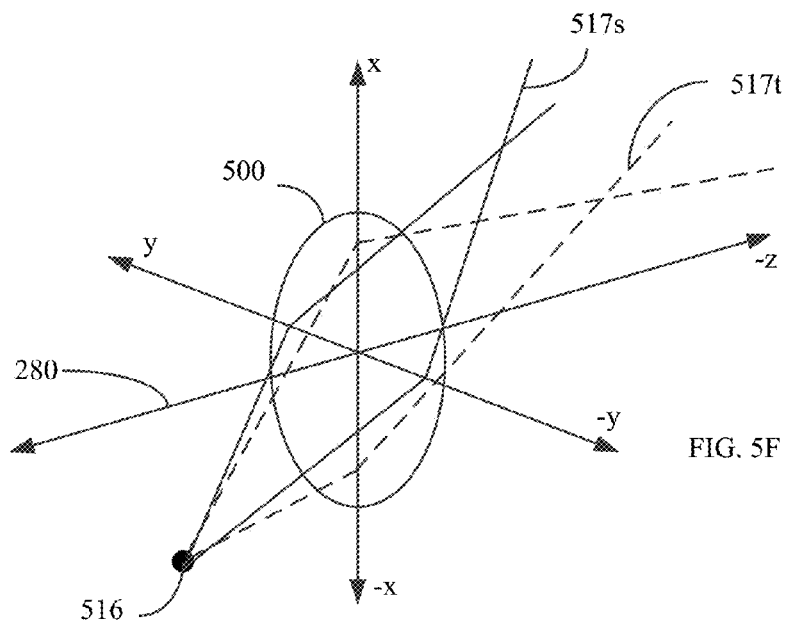
FIG. 5F shows a perspective view of the IOL 500 and the optical rays incident on the IOL from an off-axis object.

The MTF for the various embodiments of IOLs described below is calculated for both sagittal rays (e.g., 517s) and tangential rays (e.g., 517t) originating from an object 516 disposed with respect to the point of intersection of the lens (e.g. lens 500) and the optical axis 280. The MTF is calculated for various off-axis positions of the object 516 represented by coordinates along the x-direction and the y-direction in a Cartesian coordinate system in which the point of intersection of the lens (e.g. lens 500) and the optical axis 280 is disposed at the origin of the Cartesian coordinate system and the optical axis (e.g. optical axis 280) is along the z-direction, as shown in FIG. 5F. In various implementations, the point of intersection of the lens (e.g. lens 500) and the optical axis 280 can coincide with the geometric of the IOL and/or the geometric center of a surface of the IOL.

Embodiment 1

A patient implanted with a standard IOL having a tonic surface (such as TECNIS® toric IOL) that is configured to correct for corneal astigmatism may be able to view objects with some contrast sensitivity in the absence of central vision. FIG. 7A shows a cross-section view of an embodiment of a standard intraocular lens (IOL) configured to provide improved vision at a location of the peripheral retina. However, since the standard toric IOL is optimized for foveal vision (or central vision), the contrast sensitivity for light incident at oblique angles (e.g. between about ±10 degrees with respect to the optical axis 2501 in the tangential plane and/or between about ±30 degrees with respect to the optical axis 2501 in the sagittal plane) may not be high. For example, a standard IOL can provide an average MTF of about 0.7 for an eccentricity between 7-13 degrees for spatial frequency of 30 cycles/mm. Generally, an improvement in the MTF from 0.7 to 0.8 can provide a substantial visual benefit for a patient with AMD. For example, without any loss of generality, an increase in MTF from 0.7 to 0.8 corresponds to about 15% contrast sensitivity improvement, or 1 line of visual acuity (VA). Various implementations described herein can provide 2 lines VA and 30% contrast sensitivity more. The improvement in the VA and contrast sensitivity can be more if the peripheral power errors are larger. Accordingly, a patient with AMD can benefit from an increase in MTF at a peripheral retinal location. In various implementations, the spherical power of the implementation of the standard toric IOL described above in Embodiment 1 can be optimized to provide increased contrast sensitivity at a PRL away from the fovea. For example, the spherical power can be optimized by selecting the design that will provide the highest MTF values at the spatial frequency range of relevance for the patient through evaluation in an eye model using the patient's biometric data.

Embodiment 2

FIG. 7B shows a cross-section view of an embodiment of an enhanced toric IOL configured to provide improved vision at a location of the peripheral retina. Such lenses are also described in U.S. application Ser. No. 14/644,110 filed concurrently herewith on Mar. 10, 2015, titled "ENHANCED TORIC LENS THAT IMPROVES OVERALL VISION WHERE THERE IS A LOCAL LOSS OF RETINAL FUNCTION,", which is incorporated herein by reference in its entirety. The enhanced toric lens can include a toric surface and a spherical surface opposite the toric surface. The sagittal depth or the distance from the center of the toric surface to an imaginary flat plane joining the ends of the anterior toric surface, z, can be given by equation (3) below:

As another example, the enhanced toric surface can be described mathematically by equation (2) below:

$$z = \frac{cr^2}{1 + \sqrt{1 - (1+k)c^2 r^2}} + \sum_{i=1}^{4} \alpha_i r^{2i} + \sum_{i=1}^{N} A_i Z_i(\rho, \phi) \quad (2)$$

where z is the sag of the surface, c is the curvature of the surface, r the radial distance from the optical axis 515, k the conic constant, a the aspheric coefficients, A are the Zernike coefficients and Z are the Zernike polynomials. The fifth and the sixth Zernike coefficients correspond to the astigmatic terms and the seventh and the eighth Zernike coefficients correspond to the coma term. The aspheric coefficients α are rotationally symmetric. In various implementations, the surface sag (z) of the toric surface can include upto eighth order aspheric terms. In some implementations, the surface sag (z) of the toric surface can include less than eighth order (e.g., 0, 2, 4, 6) or greater than eighth order (e.g., 10 or 12) aspheric terms. Alternately, the toric surface can be described by up to 34 Zernike coefficients. In some implementations, the toric surface can be described by less than 34 Zernike coefficients. In some implementations, the toric surface can be described by more than 34 Zernike coefficients. Additionally, the first/and or second surface can be described as a combination of the aspheric and Zernike coefficients. The toric surface that reduces peripheral errors can be determined by optimizing the Zernike coefficients for the astigmatic and the coma terms. The toric IOL can include redirecting elements similar to the prismatic features and/or diffractive features described herein. The redirecting elements can be configured to redirect light incident on the eye along the optical axis and/or at an angle to the optical axis to one or more locations on the retina.

Optical simulations indicate that the average MTF for the implementation of a lens with an enhanced toric surface as described above at a peripheral retinal location at an eccentricity between about 7-degrees and about 13-degrees can be greater than 0.8 at a spatial frequency of 30 cycles/mm for light incident in the tangential as well as the sagittal planes. Although, the implementation of the IOL with an enhanced toric surface has good contrast sensitivity for a large field of view along the horizontal angle, the contrast sensitivity could reduce if IOL is tilted during or after implantation or the angle of fixation changes. Additionally, the foveal image quality provided by a lens with an enhanced toric surface may be degraded.

Embodiment 3

FIG. 7C shows a cross-section view of an embodiment of a symmetric single optic IOL configured to provide improved vision at a location of the peripheral retina. The symmetric single optic lens can be symmetric about the optical axis such that the image quality in a region around the optical axis is uniform. The symmetric single optic lens illustrated in FIG. 7C can have surfaces that are described by equation (1) above. In various implementations, the surfaces of the symmetric single optic lens can be spherical, aspheric, a biconic Zernike surface, conic, etc. The symmetric single optic lens can be configured to provide an average MTF greater than about 0.7 at spatial frequency of 30 cycles/mm for eccentricity at a peripheral retinal location at an eccentricity between about 7-degrees and about 13-degrees for light incident obliquely with respect to the optical axis and focused at a peripheral retinal location as well as a contrast sensitivity greater than about 0.7 for spatial frequency of 30 cycles/mm for light incident parallel to the optical axis and focused at the fovea 260.

Embodiment 4

FIG. 7D shows a cross-section view of an embodiment of an asymmetric single optic IOL configured to provide improved vision at a location of the peripheral retina. The embodiment illustrated in FIG. 7D can include one surface that is spherical and another surface that is aspheric. For example, in various implementations, one surface of the lens can be a biconic Zernike surface. The lens can have a central thickness $t_{cen}$ along the optical axis. The surfaces of the lens can be configured such that the thickness $t_1$ of an edge of the lens can be greater than the thickness $t_2$ of the other edge of the lens. Accordingly, the IOL can appear wedge shaped. In various implementations, the central thickness $t_{cen}$ can be less than, greater than or equal to either of the edge thicknesses $t_1$ or $t_2$.

The sagittal depth or the distance from the center of the aspheric surface to an imaginary flat plane joining the ends of the aspheric surface, z, can be given by the following equation:

$$z = \frac{c_x x^2 + c_y y^2}{1 + \sqrt{1 - (1+k_x)c_x^2 x^2 - (1+k_y)c_y^2 y^2}} +$$

-continued $$\sum_{i=1}^{16} \alpha_i x^i + \sum_{i=1}^{16} \beta_i y^i + \sum_{i=1}^{16} A_i Z_i(\rho, \varphi),$$

where x and y are distances in the Cartesian coordinate system from the center of the curvature of the surface, $c_x$ and $c_y$ are the curvatures along the x and the y axes, $k_x$ and $k_y$ are the conic constants along the x and the y axes, $A_i$ are the Zernike coefficients and $Z_i$ are the standard Zernike polynomials. The implementation of the lens illustrated in FIG. 7D can advantageously provide the same contrast sensitivity at the peripheral retinal location regardless of the tilt of the lens and/or the angle of fixation. In various implementations, the lens illustrated in FIG. 7D could provide an average MTF greater than about 0.8 at a spatial frequency of 30 cycles/mm at a peripheral retinal location at an eccentricity between about 7-degrees and about 13-degrees.

Embodiment 5

FIG. 7E shows a cross-section view of an embodiment of a thick symmetric IOL configured to provide improved vision at a location of the peripheral retina. The lens illustrated in FIG. 7E can be similar to the optic 500 illustrated in FIG. 5A. In various implementations of the lens illustrated in FIG. 7E, the surfaces of the can be aspheric and have a profile described by equation (1) above. In various implementations of the lens illustrated in FIG. 7E, the surfaces can include higher order aspheric terms such as upto $8^{th}$ order Zernike coefficients or higher. Various implementations of the lens illustrated in FIG. 7E can have a thickness between about 1 mm and about 1.6 mm. The average MTF for the implementation of a lens illustrated in FIG. 7E at a peripheral retinal location at an eccentricity between about 7-degrees and about 13-degrees can be greater than 0.8 at a spatial frequency of 30 cycles/mm for both tangential and sagittal foci.

Embodiments 6 & 7

The implementations of lenses discussed above can be implanted in the eye such that the distance between the pupil and the anterior surface of the lens is small. For example, the implementation of lenses disclosed above can be implanted such that the distance between the pupil and the anterior surface of the lens is between 0.9 mm and 1.5 mm. However, it is also conceived that the implementations of the lens discussed above can be implanted as far back in the eye as possible. For example, in some implementations, the lens can be implanted such that it is still in the capsular bag but the distance closer to the retina. In such implementations, the distance between the pupil and the anterior surface of the lens can be between distance between 1.5 mm and 3.2 mm. The profiles of the various surfaces would change as the distance between the pupil and the lens changes. This is illustrated in FIGS. 7F and 7G and discussed below. FIG. 7F shows a cross-section view of an embodiment of a moved symmetric IOL configured to provide improved vision at a location of the peripheral retina and FIG. 7G shows a cross-section view of an embodiment of a moved asymmetric IOL configured to provide improved vision at a location of the peripheral retina.

A comparison of FIGS. 7C and 7F and a comparison of FIGS. 7D and 7G illustrates that the curvatures of the surfaces change as the distance between the pupil and the retina is varied. The lens illustrated in FIG. 7F has an average MTF greater than about 0.8 at a spatial frequency of 30 cycles/mm at a peripheral retinal location at an eccentricity between about 7-degrees and about 13-degrees for both tangential and sagittal foci. The lens illustrated in FIG. 7G also has an average MTF greater than about 0.8 at a spatial frequency of 30 cycles/mm at a peripheral retinal location at an eccentricity between about 7-degrees and about 13-degrees for both tangential and sagittal foci.

Embodiments 8-11

The implementations of lenses illustrated in FIGS. 7H-7K illustrate implementations of a dual optic IOL whose surfaces are configured such that the light incident obliquely with respect to the optical axis is focused at a peripheral retinal location with reduced errors. Such lenses are also described in U.S. application Ser. No. 14/644,101, filed concurrently herewith on Mar. 10, 2015, titled "DUAL-OPTIC INTRAOCULAR LENS THAT IMPROVES OVERALL VISION WHERE THERE IS A LOCAL LOSS OF RETINAL FUNCTION,", which is incorporated herein by reference in its entirety. FIG. 7H shows a cross-section view of an embodiment of a dual optic IOL configured to provide improved vision at a location of the peripheral retina. FIG. 7I shows a cross-section view of an embodiment of a dual optic IOL configured to provide improved vision at a location of the peripheral retina and at the fovea. FIG. 7J shows a cross-section view of an embodiment of an accommodating dual optic IOL configured to provide improved vision at a location of the peripheral retina. FIG. 7K shows a cross-section view of an embodiment of an accommodating dual optic IOL configured to provide improved vision at a location of the peripheral retina and at the fovea. The surfaces of the lenses illustrated in FIGS. 7H-7K can be aspheric or spherical. The lens illustrated in FIGS. 7H-7K have an average MTF greater than about 0.8 at a spatial frequency of 30 cycles/mm at a peripheral retinal location at an eccentricity between about 7-degrees and about 13-degrees for both tangential and sagittal foci. One or both of the viewing elements of the dual optic IOL can include redirecting elements similar to the prismatic features and/or diffractive features described herein. The redirecting elements can be configured to redirect light incident on the eye along the optical axis and/or at an angle to the optical axis to one or more locations on the retina.

Embodiments 12 & 13

The implementations of lenses illustrated in FIGS. 7M and 7N illustrate implementations of a piggyback IOL that can be provided in addition to an existing lens (natural lens or a standard IOL) for patients with AMD. Such lenses are also described in U.S. application Ser. No. 14/644,107, filed concurrently herewith on Mar. 10, 2015, titled "PIGGY-BACK INTRAOCULAR LENS THAT IMPROVES OVERALL VISION WHERE THERE IS A LOCAL LOSS OF RETINAL FUNCTION,", which is incorporated herein by reference in its entirety. FIG. 7L shows a cross-section view of an embodiment of a symmetric piggyback IOL configured to provide improved vision at a location of the peripheral retina and at the fovea. FIG. 7M shows a cross-section view of an embodiment of an asymmetric piggyback IOL configured to provide improved vision at a location of the peripheral retina and at the fovea. The piggyback IOLs can be configured to provide optical power in the range between about −10.0 Diopter and +10.0 Diopter. The piggyback IOLs can have a thickness between about 0.3 mm and about 1.0 mm such that they can be inserted between the iris and an existing lens.

The surfaces of the lenses illustrated in FIGS. 7M and 7N can be aspheric or spherical. The lens illustrated in FIGS. 7M & 7N have an average MTF greater than about 0.7 at a spatial frequency of 30 cycles/mm at a peripheral retinal location at an eccentricity between about 7-degrees and about 13-degrees for both tangential and sagittal foci. The implementation of piggyback lenses disclosed herein can include redirecting elements similar to the prismatic features and/or diffractive features described herein. The redirecting elements can be configured to redirect light incident on the eye along the optical axis and/or at an angle to the optical axis to one or more locations on the retina.

The tables below summarize the optical performance of various embodiments of lenses discussed above. The optical performance is characterized using a figure of merit such as an average MTF at a spatial frequency of 30 cycles/mm at different locations in the peripheral retina at an eccentricity between 7-13 degrees. Table 1 provides the optical performance of the different lenses for a large patch configuration. Without any loss of generality, a large patch configuration refers to configuration when the isoplantic patch is large. In other words, there are a large range of angles (patch) of incidence that are focused at corresponding retinal locations in a small area such that any individual point of the image is sharply focused. Table 2 provides the optical performance of the different lenses for reading.

TABLE 1

Optical performance for a large patch configuration

| Design | Figure of merit large patch | Acceptable foveal | Foveal MTF at 100 cyces/mm | Symmetrical | Symmetrical figure of merit | MTF at 30 cycles/mm, eccentricity 5/15 deg |
|---|---|---|---|---|---|---|
| Standard | 0.70 | X | 0.76 | X | 0.67 | 0.86/0.42 |
| Toric (1 D) | 0.80 | | 0.24 | | 0.58 | 0.68/0.60 |
| Enhanced Toric | 0.90 | | 0.25 | | 0.58 | 0.63/0.36 |
| Double asphere | 0.87 | X | 0.74 | X | 0.75 | 0.87/0.45 |
| Zernike anterior, standard posterior | 0.90 | | 0.19 | | 0.55 | 0.66/0.54 |
| Thick asphere | 0.89 | X | 0.56 | X | 0.91 | 0.89/0.59 |
| Moved asphere | 0.87 | X | 0.73 | X | 0.88 | 0.91/0.49 |
| Moved asymmetric Zernike | 0.94 | | 0.19 | | 0.74 | 0.82/0.74 |
| Dual optics | 0.92 | | 0.07 | X | 0.94 | 0.81/0.65 |
| Dual optics with good foveal | 0.89 | X | 0.77 | X | 0.90 | 0.92/0.55 |
| Dual optics accommodating | 0.89 | X | 0.61 | X | 0.90 | 0.88/0.55 |
| Dual optics accommodating with good foveal | 0.88 | X | 0.77 | X | 0.89 | 0.92/0.55 |
| Piggyback asymmetric | 0.90 | | 0.19 | | 0.63 | 0.76/0.58 |
| Piggyback symmetric | 0.74 | | 0.39 | X | 0.71 | 0.83/0.31 |

TABLE 2

Optical performance for lenses configured for reading

| Design | Figure of merit reading | Acceptable foveal | Foveal MTF at 100 cyces/mm | Symmetrical | Figure of merit for large patch |
|---|---|---|---|---|---|
| Standard | 0.41 | x | 0.76 | X | 0.70 |
| Toric (1 D) | 0.43 | | 0.34 | | 0.79 |
| Enhanced Toric | 0.44 | | 0.22 | | 0.83 |

TABLE 2-continued

Optical performance for lenses configured for reading

| Design | Figure of merit reading | Acceptable foveal | Foveal MTF at 100 cyces/mm | Symmetrical | Figure of merit for large patch |
|---|---|---|---|---|---|
| Double asphere | 0.58 | X | 0.44 | x | 0.82 |
| Zernike anterior, standard posterior | 0.54 | | 0.14 | | 0.81 |
| Thick asphere | 0.86 | | 0 | X | 0.83 |
| Moved asphere | 0.74 | | 0.30 | X | 0.82 |
| Moved asymmetric Zernike | 0.84 | | 0.30 | | 0.87 |
| Dual optics | 0.87 | x | 0.73 | X | 0.84 |
| Dual optics with good foveal | 0.75 | | 0.76 | X | 0.88 |
| Dual optics accommodating | 0.81 | | 0.14 | | 0.82 |

Intraocular Lens with Two Zones

As discussed above, patients suffering from loss of central vision due to AMD or retinal scotoma can benefit from ophthalmic solutions that deflect incident light to a preferred peripheral retinal location away from the fovea. Embodiments discussed herein can deflect incident light to a preferred peripheral retinal location away from the fovea and additionally correct optical errors at the preferred retinal location. Various embodiments described herein include ophthalmic solutions that are configured to focus a first portion of the incident light at a first preferred location of the retina (e.g., fovea 260) and a second portion of the incident light at a second preferred location of the retina (e.g., PRL 290). Such ophthalmic solutions are described below with reference to FIG. 8.

Figure 8:
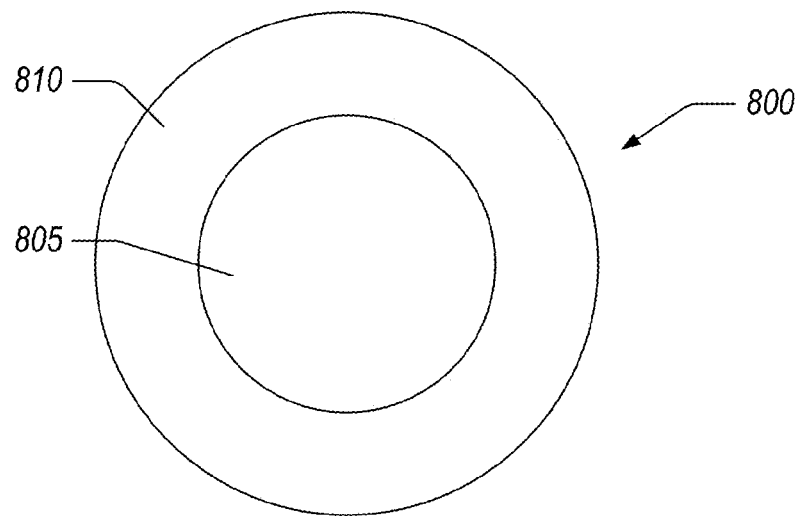
FIG. 8 illustrates an example intraocular lens having two zones.

FIG. 8 illustrates an example intraocular lens 800 having two zones 805, 810 with different optical properties. The IOL 800 can be configured to improve or optimize both far vision and near vision, and to do so in different ways. The IOL 800 advantageously can improve overall vision where there is a loss of central vision by providing a magnified image at the PRL for near vision and an image at the retina that is substantially undeflected and unmagnified for far vision. In some embodiments, the near vision improving zone can redirect an image to the PRL without providing any additional magnification. In some embodiments, the far vision zone can redirect an image to a far-vision PRL, where the far-vision PRL may be different from the near-vision PRL. It is to be understood, then, that the intraocular lens 800 may have more than two zones where each zone redirects images to a different PRL. In such cases, the zones of the intraocular lens can have different, similar, or identical optical powers, and the added magnification of one or more of the zones can be 0. This multi-zone IOL may be advantageous where a patient uses different PRLs for different vision tasks or where the patient lacks a stable PRL.

In some embodiments, the first zone 805 is configured to improve or optimize near vision. The first zone 805 can be configured to redirect an optical axis to a PRL within an eye of a patient to improve near vision which is adversely affected by a loss of central vision. In some embodiments, in addition to redirecting incident light to the PRL, the first zone 805 can have an optical power configured to magnify the image at the PRL and to correct for the peripheral errors arising at the eccentricity of the PRL, where the magnification is relative to the magnification provided by the eye without the IOL 800. In some embodiments, the magnification of the image at the PRL can be accomplished through a combination of the magnification of the first zone 805 and a magnification provided by a spectacle lens or contact lens. The spectacle lens or contact lens may be used to magnify and focus on the retina relatively distant objects. For example, the IOL 800 with additional optical power may result in a patient holding objects relatively close to the eye so the image of the object is magnified and focused on the retina. By accounting for the use of a spectacle lens or contact lens, the IOL 800 with a magnifying zone can be configured to magnify and focus on the retina objects that are relatively further from the patient.

The first zone 805 can be configured to deflect incident light onto the PRL using a number of techniques including, for example and without limitation, prisms, diffraction gratings, tailored refractive surfaces, materials with varying indices of refraction, or any of the other techniques, systems, and/or methods disclosed herein. For example, the first zone 805 can include a redirection element configured in accordance with the description provided herein with reference to FIGS. 11-22. As another example, the first zone 805 can include a diffraction grating configured in accordance with the description provided herein with reference to FIG. 26. As another example, the first zone 805 can include a decentered GRIN lens configured in accordance with the description provided herein with reference to FIG. 23.

In some embodiments, the optical diameter of the first zone 805 is small relative to the diameter of the IOL 800 (e.g., at least about 1.5 mm and/or less than about 4.5 mm, or at least about 2 mm and/or less than about 3 mm, or less than about 2.5 mm). This advantageously can ease design constraints of the IOL lens 400 because it can reduce the thickness of the lens. A thinner lens can be easier to implant and can have less risk of complications. The small optical diameter may also limit the central thickness of the IOL 400 such that a solution utilizing a prism may be appropriate.

In some embodiments, the second zone 810 is configured to improve or optimize far vision. The second zone 810 can be configured to improve a user's contrast sensitivity here there is a loss of central vision by maintaining or approximating the optical axis and magnification of the natural lens. This may allow the user to utilize all 4 quadrants of the visual field for far vision which is beneficial for orientation and moving around. For instance, the second zone 810 can be configured to not significantly deflect the optical axis of incident light and to not significantly magnify the image on the retina. Doing so may allow a user to process the visual context of a scene which reduces disorientation and reduces difficulty in moving around and identifying moving objects.

In FIG. 8, the first and second zones 805, 810 are respectively illustrated as circular and annular. However, the shapes of the first and second zones 805, 810 can be any regular or irregular closed shape configured to provide the visual characteristics to improve overall vision or contrast sensitivity where there is a loss of central vision. The second zone 810 can be configured to surround the first zone 805, and, in some embodiments, the second zone 810 can be configured to extend from the periphery of the first zone 805 to the periphery of the IOL 800. In some embodiments, the IOL 800 can include more than two zones. For example, a third zone can be included in the IOL 800 which can be configured to deflect incident light along a deflected optical axis (e.g., to the PRL or to another location on the retina such as a secondary PRL), to magnify the image on the retina, to correct aberrations, etc. In some embodiments, the first and second zones 805, 810 can be adjacent to one another or separate regions on the IOL 800, where neither zone surrounds the other zone.

Figure 9:
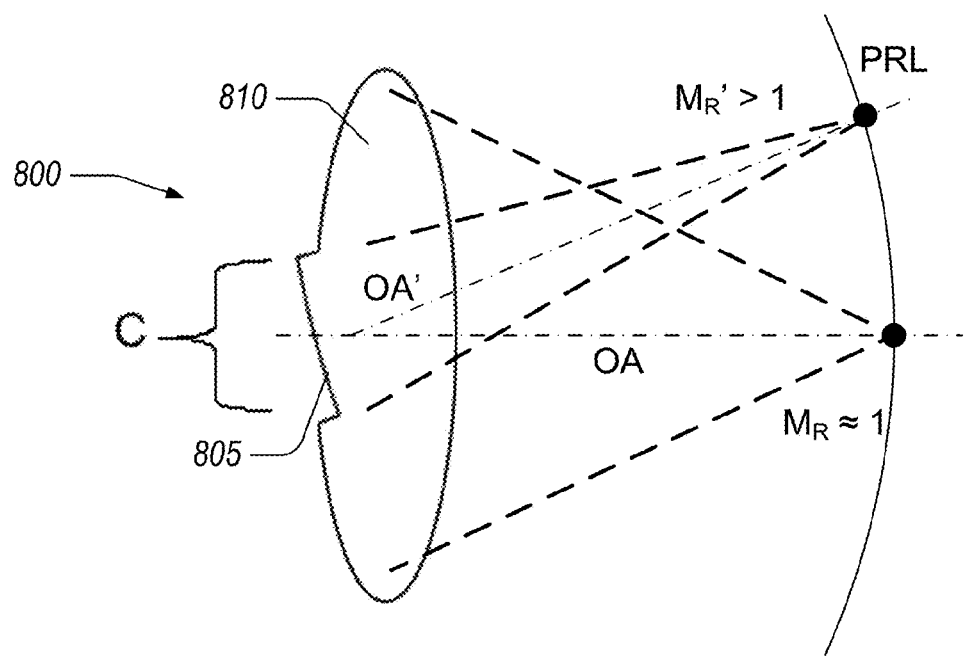
FIG. 9 illustrates an example intraocular lens having two zones with different optical powers and different deflection angles.

The separation or boundary between the first zone 805 and the second zone 810 of the IOL 800 can be a physical discontinuity (e.g., as illustrated in FIG. 9), an optical discontinuity (e.g., different indices of refraction), or both. In some embodiments, the first zone 805 and second zone 810 are not separated by a discontinuity, physical and/or optical, but are defined in terms of functionality where one of the zones deflects incident light and magnifies the image on the retina whereas the other zone does not substantially deflect incident light or magnify the image on the retina. In such cases, the transition between the zones can be a smooth or substantially continuous change of physical and/or optical properties.

The IOL 800 can be modified to provide the two zones 805, 810 and their associated properties, as set forth herein. An unmodified IOL can be provided and altered so as to include the first and second zones 805, 810. For example, a redirection element can be added to a portion of the IOL 800 to direct light along a deflected optical axis. As another example, a portion of the anterior surface of the IOL 800, the posterior surface of the IOL 800, or both can be modified to provide the two zones 805, 810. As another example, the refractive index of the first zone 805, of the second zone 810, or of both zones can be modified using a laser treatment.

The IOL 800 with at least two zones can also be further modified to provide additional benefits. For example, one or both zones 805, 810 can be tailored to reduce or eliminate optical aberrations (e.g., spherical aberration, astigmatism, coma, field distortion, chromatic aberration, etc.). As another example, the first zone 805 may be modified to include a bifocal lens to improve accommodation for a user.

The IOL 800 described herein with reference to FIG. 8 includes the first zone 805 configured to improve or optimize near vision and the second zone 810 configured to provide vision in all four quadrants of the visual field to aid in orientation and moving around when using far vision. In some embodiments, the IOL 800 can be configured such that the roles of the first and second zones 805, 810 are reversed, e.g., the first zone 805 provides vision in all four quadrants of the visual field and the second zone 810 is configured to improve or optimize near vision.

FIG. 9 illustrates an example intraocular lens 800 having two zones 805, 810 with different optical powers. As illustrated, the first zone 805, or central zone "C", has a physical discontinuity from the second zone 810, or peripheral zone, which surrounds the central zone 805. The central zone 805 is used for near vision and focuses incident light on the PRL (e.g., along a deflected optical axis OA') and magnifies the image at the PRL (e.g., the magnification of the eye with the IOL 800 relative to the magnification of the eye with its natural lens is greater than 1, or $M_R'>1$). The peripheral zone 810 is used for far vision and directs incident light to the retina without substantial deflection (e.g., maintains the optical axis OA of the eye with its natural lens) and without substantial magnification (e.g., the magnification of the eye with the IOL 800 relative to the magnification of the eye with its natural lens is about 1, or $M_R \approx 1$).

The deflected optical axis OA' can be configured to deviate from the optical axis of the eye with its natural lens to intersect the retina at the PRL. The undeflected optical axis OA can be configured to substantially align with the optical axis of the natural lens (e.g., the optical axis that intersects the fovea at the retina or which represents an eccentricity of about 0 degrees). The relative magnification of the central zone $M_R'$ can be configured to magnify the image at the PRL relative to a magnification of the eye with its natural lens M or the relative magnification of the peripheral zone, $M_R$. The relative magnification of the peripheral zone $M_R$ can be configured to be substantially the same as the magnification provided by the natural lens. In some embodiments, both $M_R$ and $M_R'$ can be greater than 1. In some embodiments, $M_R'$ can be greater than about 1.75 and/or less than or equal to about 6 (e.g., where $M_R'=1+F/4$ and F is the added power in diopters).

In some embodiments, the power of the central zone 805 can be greater than an optical power of the peripheral zone 810. For example, the optical power of the central zone 805 can be about 10 diopters higher or at least 3 diopters higher and/or less than 20 diopters higher than the optical power of the peripheral zone 810. In such a configuration, the near image is blurred for far vision such that the blurred near image is a limited impediment to far vision. In addition, the higher power for near vision can enable the user to see a sharper image up close (e.g., improving a user's ability to read).

Figure 10:
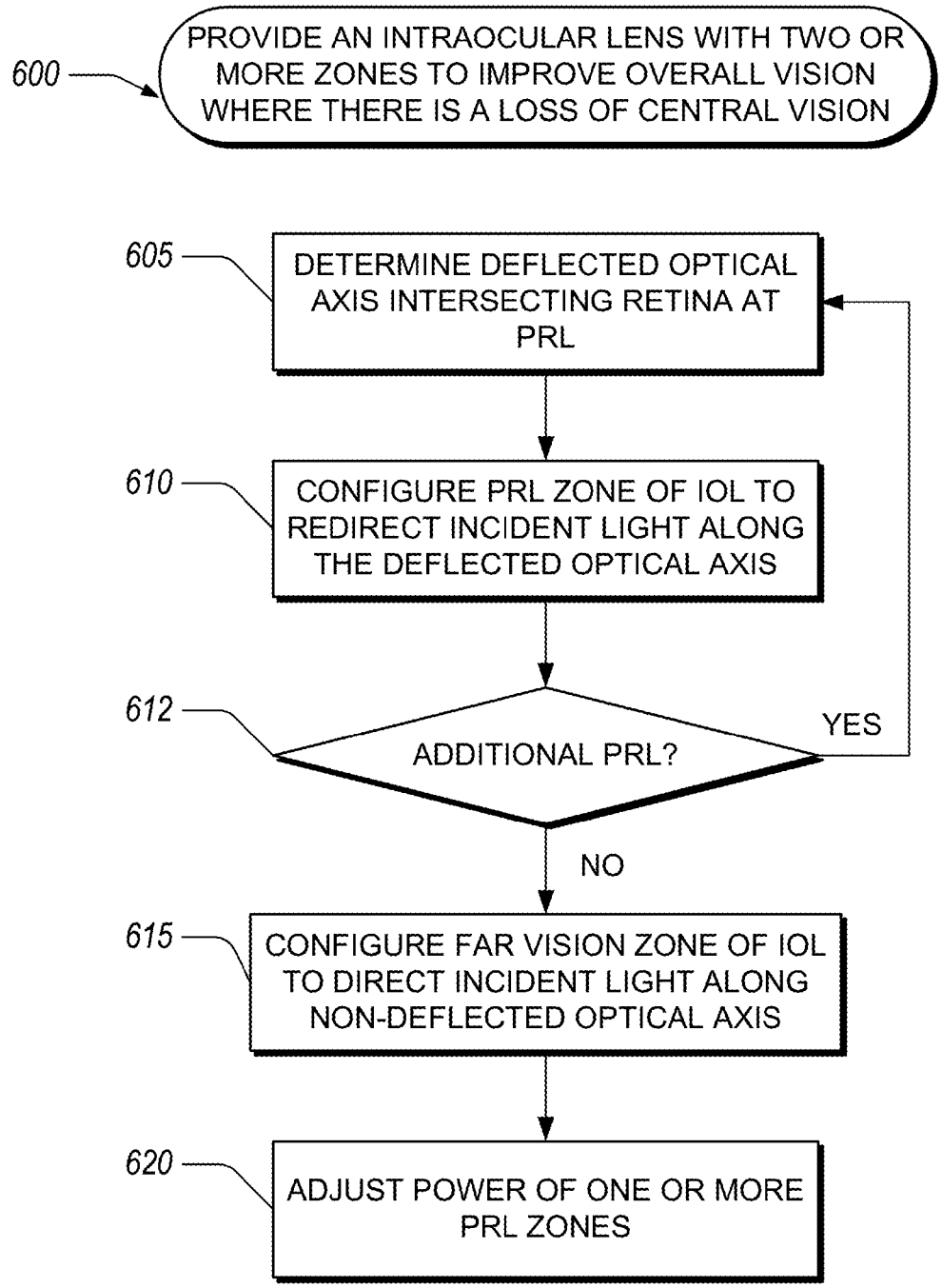
FIG. 10 illustrates an example method for providing an intraocular lens with two or more zones to improve overall vision where there is a loss of central vision.

FIG. 10 illustrates an example method 600 for improving contrast sensitivity or overall vision where there is a loss of central vision using an intraocular lens with two zones. The IOL can be similar to the IOL described herein with reference to FIGS. 8 and 9, where there is a first zone configured for near vision and a second zone configured for far vision.

In block 605, a deflected optical axis is determined which intersects a PRL of a patient at the retina. The deflected optical axis can be considered to be deflected from the natural optical axis 280 of the eye, as illustrated in FIG. 1. The deflected optical axis can be configured to intersect the patient's retina at the PRL such that light directed along the deflected optical axis and focused onto the patient's PRL can be resolved by the patient instead of being directed along the natural optical axis and focused onto a damaged portion of the retina. The PRL can be one of a plurality of potential PRLs, some or all of which may be advantageously used by a patient.

In some embodiments, block 605 includes determining the PRL (or plurality of candidate PRLs) for a patient. The PRL can be determined using analytical systems and methods designed to assess retinal sensitivity and/or retinal areas for fixation. Such systems and methods can include, for example and without limitation, providing a patient with stimuli and imaging the patient's retina to assess topographic retinal sensitivity and locations of preferred retinal loci. For example, a microperimeter can be used to determine a patient's PRL by presenting a dynamic stimulus on a screen and imaging the retina with an infrared camera. As another example, a retinal area used for fixation can be assessed using a laser ophthalmoscope (e.g., an infrared eye tracker) which can be used to determine discrete retinal areas for fixation for various positions of gaze.

In some embodiments, a diagnostics system can be used to determine the PRL. The system can be configured to bypass the optics of the patient. In some instances, optical errors induced by a patient's optics can cause the patient to select a non-optimal PRL or a PRL which does not exhibit benefits of another PRL, e.g., where a patient selects an optically superior but neurally inferior region for the PRL. This can be advantageous because this would allow the identification of a PRL which, after application of corrective optics (e.g. the IOLs described herein), would provide superior performance compared to a PRL selected utilizing a method which includes using the patient's optics because the corrective optics reduce or eliminate the optical errors which are at least a partial cause for a patient selecting a sub-optimal PRL.

In some embodiments, multiple candidate locations for the PRL can be determined. The preferred or optimal PRL, or the preferred or optimal set of PRLs, can be based at least upon several factors including, for example and without limitation, a patient's ability to fixate a point target, distinguish detail, and/or read; aberrations arising from redirecting images to the candidate PRL; proximity to the damaged portion of the retina; retinal sensitivity at the candidate location; and the like. The preferred or optimal PRL can depend on the visual task being performed. For example, a patient can have a first PRL for reading, a second PRL when navigating, and a third PRL when talking and doing facial recognition, etc. Accordingly, multiple PRLs may be appropriate and an IOL can be configured to redirect incident light to the appropriate PRLs using multiple zones, as described herein. For example, although the method 600 describes providing an IOL with two zones, the method 600 can be expanded to include providing an IOL with greater than two zones, with one or more zones redirecting light to a designated PRL, where the zone can be configured to have additional optical power or no additional optical power. In some embodiments, a plurality of PRLs can be selected or used for a patient to accomplish one or more visual tasks.

In block 610, the IOL is configured to include a PRL zone which redirects incident light along the deflected optical axis determined in block 605. The PRL zone can be used to improve near vision for the patient suffering from central vision loss, e.g., to improve vision associated with one or more visual tasks. The IOL can be configured to include an optical and/or physical discontinuity such that the first zone deflects incident light along the deflected optical axis. The IOL can be configured to include a redirection element (e.g., prisms, diffraction gratings, and/or any other system or method disclosed or described herein) on an anterior surface of the IOL, on a posterior surface of the IOL, and/or the anterior and/or posterior surfaces of the IOL can be modified to deflect the optical axis. In some embodiments, the deflecting element can be designed to correct for the peripheral refractive errors at the PRL location. These errors can be determined at the time of PRL determination. The IOL can be configured to redirect the incident light by altering the index of refraction of the first zone (e.g., using a laser treatment) so that light incident on the first zone is deflected along the deflected optical axis. The IOL can be configured to include a combination of features (e.g., redirection elements, tailored indices of refraction, etc.) to achieve the result of deflecting the optical axis.

In block 612, the procedure is repeated if there are multiple PRLs to be used in the IOL. For each PRL, a deflected optical axis is determined in block 605 and a PRL zone in the IOL is configured to direct images to the corresponding PRL. In this way, the IOL can be configured to improve overall vision by directing images to a plurality of PRL locations.

In block 615, the IOL is configured to include a far vision zone which directs incident light along an undeflected optical axis (e.g., the optical axis of the patient's eye with its natural lens). The far vision zone can be configured to provide far vision for the patient. The undeflected optical axis can be advantageous for far vision because it can direct light from a scene to all four quadrants of the patient's retina, providing context for the patient useful for orientation and moving around. Substantially deflecting the light may comprise vision in the part of the visual field opposite the deflection, reducing a patient's far-vision capabilities.

The far vision zone can be configured to surround one or more of the PRL zones where the PRL zones are located in a central portion of the IOL (e.g., as concentric rings or adjacent regions). The far vision zone can be configured to be located in a central portion of the IOL, in which case the PRL zones can be configured to surround the far vision zone (e.g., as concentric rings, segmented regions around the far vision zone, or a combination of these configurations).

In block 620, an optical power of one or more of the PRL zones is adjusted to be greater than a power of the far vision zone. The optical power of at least one PRL zone can be configured to provide a relative magnification of an image at the corresponding PRL, where the magnification of the image is relative to the magnification provided by the natural lens of the patient. In some embodiments, the depth of focus of the far vision zone can be extended through, for example and without limitation, refractive or diffractive principles generally applicable for IOL design. This may be advantageous because the extended depth of focus in the on-axis image may provide a greater tolerance to refractive errors (e.g., relative to deflected images) and allow for intermediate vision for the patient. Examples of such techniques are disclosed in U.S. patent application Ser. No. 12/771,550 filed Apr. 30, 2010, which is incorporated herein by reference in its entirety. The optical power of the second zone can be configured to provide little or no magnification relative to the natural lens of the patient. In some embodiments, the optical power of the first zone can be about 10 diopters or at least about 3 diopters and/or less than or equal to about 20 diopters greater than the optical power of the second zone. The magnification provided by the first zone can advantageously improve near vision without significantly compromising far vision because for far vision the near image is blurred, and for near vision the near image is magnified to compensate for reduced retinal sensitivity at the PRL.

Intraocular Lens with Tailored Redirection Element

When using a PRL to compensate for central vision loss, a patient may redirect their eyes or head so that the object to be imaged is in a location that is imaged onto the PRL. The oblique incidence of the light from the object on the eye can induce optical aberrations such as coma or astigmatism at the PRL. Similarly, some optical elements which simply redirect light from an oblique incidence to the PRL may induce equivalent or similar aberrations, even where the patient no longer redirects their eyes and/or head. It would be advantageous, then, for a patient suffering from central vision loss to incorporate into the patient's eye an optical element configured to deflect incident rays so that they form a sharp image on the PRL instead of at the fovea.

In some embodiments, an IOL can be configured to include a redirection element (e.g., a prism-like shape or other optical element with a tailored slope profile) at a surface of the IOL (or elsewhere in the eye) to shift the position of an image from the fovea to the PRL, as described herein with reference to FIG. 4A-2. When using a typical prism to perform this redirection, optical aberrations may arise due at least in part to the high vergence of the incident rays (which occur due to the focusing power of the cornea). A Fresnel prism may be used to shift the image positions and to reduce the thickness of the prism used in the IOL. However, even a very thin Fresnel prism, in combination with the incoming rays having a high vergence, will still induce optical aberrations of a magnitude that is similar to what a patient will get when fixating to the PRL by themselves. Accordingly, some embodiments provide for a redirection element with a tailored slope profile, or a tailored redirection element, which can be configured to achieve the desired shift in image position while providing good optical quality (e.g., without losing the optical quality of the unshifted image, reducing or eliminating aberrations, etc.). The tailored redirection element can include a surface with a slope which varies as a function of surface position, wherein the slope profile is calculated numerically or analytically based at least in part on the desired shift in image position and the slope profile is configured to reduce or eliminate aberrations arising from the shift in image position.

To illustrate effects of shifting an image from the fovea, simulations have been performed on an eye including various redirection elements. In the following figures, the PRL has been simulated as being 10 degrees from the fovea inside the eye. Other angles are possible, and results would be similar for other such angles. For each of FIGS. 11-13 and 18-22, the left plot shows ray convergence (rays 705) before hitting the last surface of the IOL 725, ray convergence (rays 710) after the last surface of the redirection element 720, and the focus at the PRL (the spoked circle 715), and the right plot shows the area around the PRL 715, which represents a zoomed-in view of the left plot. The axes respectively represent the surface profile of the lens in millimeters (x-axis 702) and the pupil position at the lens in millimeters (y-axis 704), that is the axes represent the position in the eye with the origin being the vertex of the posterior lens surface, and moving along the x-axis represents moving along the optical axis from the pupil to the retina. Listed above each zoomed-in view (the plot on the right in the figures) is the mean absolute transversal error at the focus and the mean ray distance to the PRL (both given in millimeters). The mean absolute transversal error is defined as the average absolute transversal distance (e.g., the absolute value of the distance along the y-axis) from the rays to the PRL at the x position corresponding to the PRL location, and smaller values are better because it indicates the resulting image is of a higher optical quality (e.g., it is less blurry) and smaller objects can be resolved. For example, if all rays intersected the PRL then the mean absolute transversal error would be 0 because at the x position, all rays would be 0 mm from the PRL along the y-axis. The mean ray distance to the PRL is defined as the average distance to the PRL (e.g., the distance from a ray to the PRL along the y-axis at the x position of the PRL) for all of the rays, and smaller values are better because it indicates a smaller systematic misplacement of the intended focal position or that, on average, the center of the point spread function is closer to the PRL. For example, if the rays are evenly spread about the PRL, then the mean ray distance would be 0 mm, indicating no misplacement of the focal position.

Figures 11, 12:
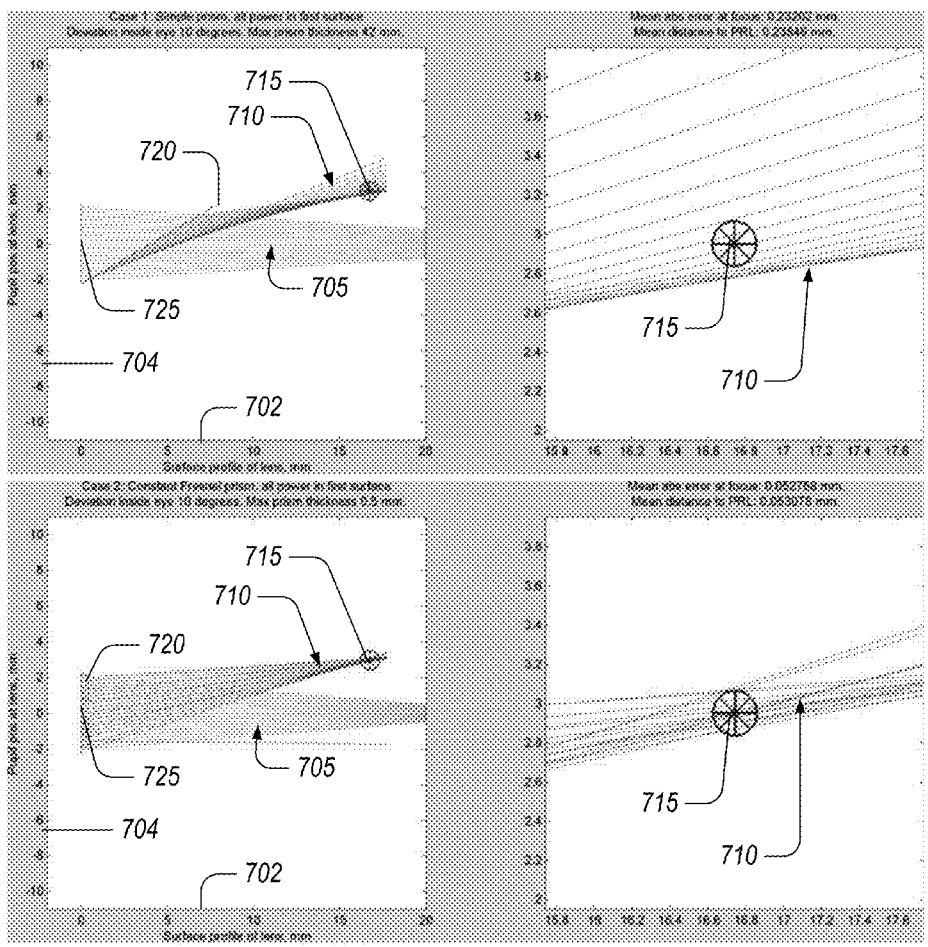
FIG. 11 illustrates a plot and a zoomed-in version of the plot showing ray convergence and image focus at a PRL when redirecting incident light using a simple prism.
FIG. 12 illustrates a plot and a zoomed-in version of the plot showing ray convergence and image focus at a PRL when redirecting incident light using a flat Fresnel prism.

The first plot, illustrated in FIG. 11, shows the effects of using a simple prism with a maximum thickness of 42 mm. The profile of the prism is shown as line 720, whereas the posterior surface of the IOL is shown as line 725. In FIG. 11, all of the optical power of the IOL is in the first, anterior surface (e.g., the posterior surface is flat, as shown). In this case, the mean absolute transversal error at the focus is about 0.23 mm and the mean ray distance to the PRL is about 0.24 mm.

Switching to a Fresnel prism 720 with a maximum height of 0.5 mm improves the optical quality at the PRL 715, as illustrated in the plots shown in FIG. 12. As in FIG. 11, the optical power of the IOL is configured to be in the first, anterior surface. In this case, the mean absolute transversal error at the focus is about 0.053 mm and the mean ray distance to the PRL 715 is about 0.053 mm, representing a significant improvement over the simple prism implementation of FIG. 11. However, these errors may still be unacceptably high due to the induced optical aberrations. For example, a mean error of about 0.05 mm represents a blurring equivalent with log MAR of about 1.0.

It may be advantageous, instead, to provide a general analytical method which produces a slope profile tailored to produce a sharp image (e.g., with limited optical aberrations) at the PRL and which accepts as input, for example and without limitation, the PRL location, retinal shape, axial length, corneal power, predicted IOL position, and power of posterior lens surface. In some embodiments, a tailored redirection element can be designed having a tailored slope profile based at least in part on such a general analytical method.

The general analytical method can provide a tailored or customized slope profile of a redirection element which achieves the desired shift in image position while maintaining good optical quality. The general analytical method can be used to generate an IOL with a redirection element tailored to redirect an image to the PRL and to reduce optical aberrations (e.g., coma) associated with such a shift in image position. The inputs of the general analytical method can include the distance from the lens vertex to the original focus (l), the index of refraction of the IOL ($n_l$), the index of refraction of the aqueous environment ($n_{aq}$), the angle inside the eye to the PRL relative to the back vertex of the IOL ($a_p$), the radial position of the IOL (x), and/or the posterior radius of curvature of the IOL (r). A first step in the general analytical method can include analytically calculating the slope at each point on the posterior surface of the IOL which would direct incident light rays to the PRL. Using Snell's law, an analytical expression can be found for the slope as a function of radial position, x, is given by Equation (3) below:

$$\text{slope}(x) = -\cos^{-1}\left(\frac{n_{aq}\cos\alpha - n_l\cos\beta}{\sqrt{n_{aq}^2 + n_l^2 - 2n_{aq}n_l\sin\alpha\sin\beta - 2n_{aq}n_l\cos\alpha\cos\beta}}\right) \quad (3)$$

-continued
where $$\alpha = \tan^{-1}\left(\frac{l\sin a_p - x}{l\cos a_p - r - \sqrt{r^2 - x^2}}\right)$$

and $$\beta = \sin^{-1}\left(\frac{n_{aq}}{n_l}\sin\left(\tan^{-1}\left(\frac{-x}{l - r - \sqrt{r^2 - x^2}}\right) + \sin^{-1}\left(\frac{x}{r}\right)\right)\right)$$

The analytical solution given as Equation (3) represents the slope as a function of position for a redirection element which can be included as an additional refractive surface positioned on or after a posterior IOL surface where the posterior IOL surface refracts the light before the redirection element. To derive the analytical solution, the initial ray is treated as converging toward the retina where the initial ray, I, is given by the equation $\tan^{-1}(-x/l)$. Then it is recalculated how it would be if the power of the back optical surface were not used (as the slope is being changed), giving the angle of the ray at every point inside the IOL. The slope of the surface of the IOL, s, is given by $\tan^{-1}(x/r)$ and the refraction at the first surface is given by $\sin^{-1}((n_l/n_{aq})\sin [l+s])$ The angle of the ray is recalculated so that it is towards the optical axis of the eye, where the angle relative to the optical axis, o, is given by r+s. The desired slope for every ray inside the IOL is calculated to hit the PRL where the desired slope, d, is given by $\tan^{-1}((l \sin a_p - x)/(l \cos a_p + r - \text{sqrt}(r^2 - x^2)))$. Snell's law is then used with the slope profile, p, as the unknown with the incident and desired ray slopes known. A solution is found for p in the equation $\sin(d-p) = n_l \sin(o-p)$. The solution, p, can be given as:

$$-\cos^{-1}\left(\frac{n_l\cos o - n_{aq}\cos d}{\sqrt{n_{aq}^2 + n_l^2 - 2n_{aq}n_l\sin d\sin o - 2n_{aq}n_l\cos d\cos o}}\right).$$

Figure 13:
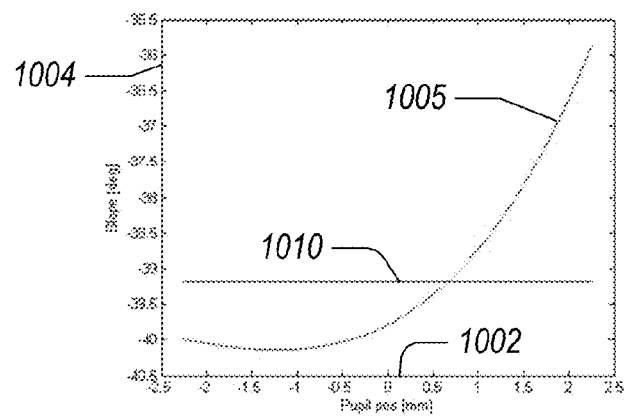
FIGS. 13-15 illustrate slope profiles of posterior surfaces of example intraocular lenses, the slope profiles based on analytical computations.
Figure 14:
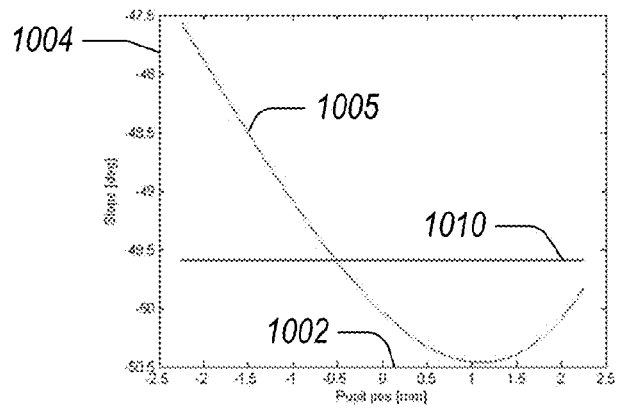
Figure 15:
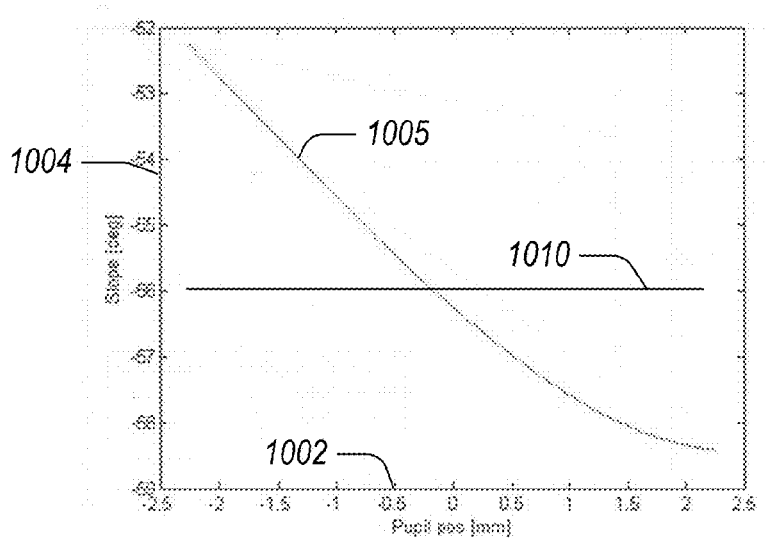
Figure 16:
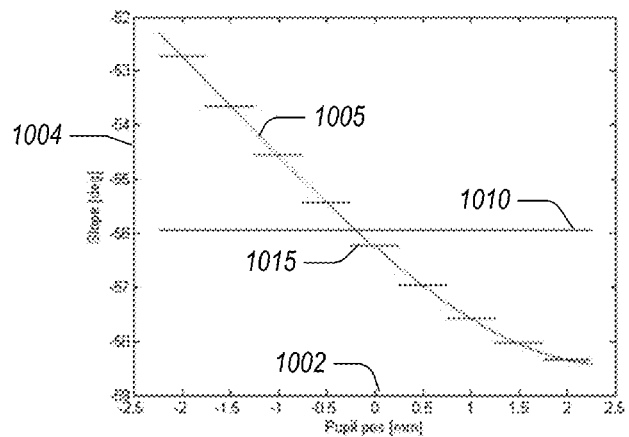
FIG. 16 illustrates a slope profile of a posterior surface of an example intraocular lens and a slope profile of a redirection element including a plurality of zones of constant slope, the slope in each zone based on analytical computations.

FIGS. 13-15 illustrate examples of slope profiles 1005 calculated using the above expression, where the PRL is located respectively at 5 degrees, 7.5 degrees, and 10 degrees from the fovea. The x-axis 1002 represents the pupil position in millimeters and the y-axis 1002 represents the slope of the redirection element in degrees. A simple prism 1010 with a constant slope is illustrated in each figure for comparison. FIG. 16 is equivalent to FIG. 15 except that it adds a slope profile 0715 for a segmented redirection element where the slope in a segment is constant across that zone and where the slope in that zone is based on the tailored slope profile 1005. At every location in the segmented redirection element, the slope is constant (e.g., within a zone, the slope is constant), but the slope is different from zone to zone. As is evident from the slope profiles in FIGS. 14-17, the slope profile does not necessarily monotonically increase or decrease as it depends on multiple factors. In addition, the difference in slope from one portion of the redirection element to another can be substantial (e.g., 10 degrees) for typical PRL locations, indices of refraction, and/or incident vergence profiles.

Figure 17:
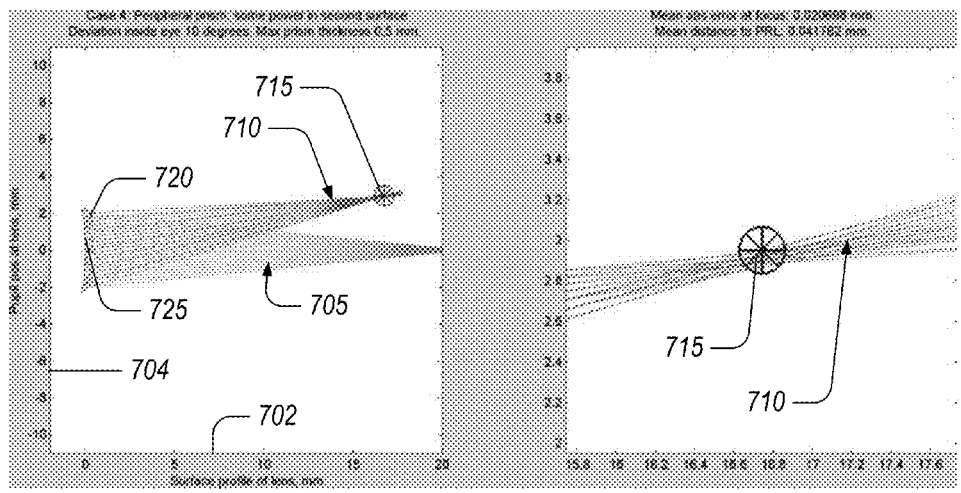
FIG. 17 illustrates a plot and a zoomed-in version of the plot showing ray convergence and image focus at a PRL when redirecting incident light using the redirection element of FIG. 16.

Applying the slope profile from FIG. 16 to a redirection element can improve the image quality at the PRL 715, as shown in FIG. 17. The analytically tailored redirection element of FIG. 17 can have different zones, wherein the slope within each zone varies according to the slope profile calculated using the analytical expression above. The redirection element with the tailored slope profile is incorporated onto the posterior surface 725 of the IOL, the posterior surface 725 having some optical power. In this case, the mean absolute transversal error at the focus is about 0.020 mm and the mean ray distance to the PRL 715 is about 0.042 mm, representing an improvement over the Fresnel prism implementation of FIG. 12. However, the first step of the general analytical method did not take the thickness of the redirection element into account. The results can be improved where these factors are accounted for in the design of the slope profile.

Figure 18:
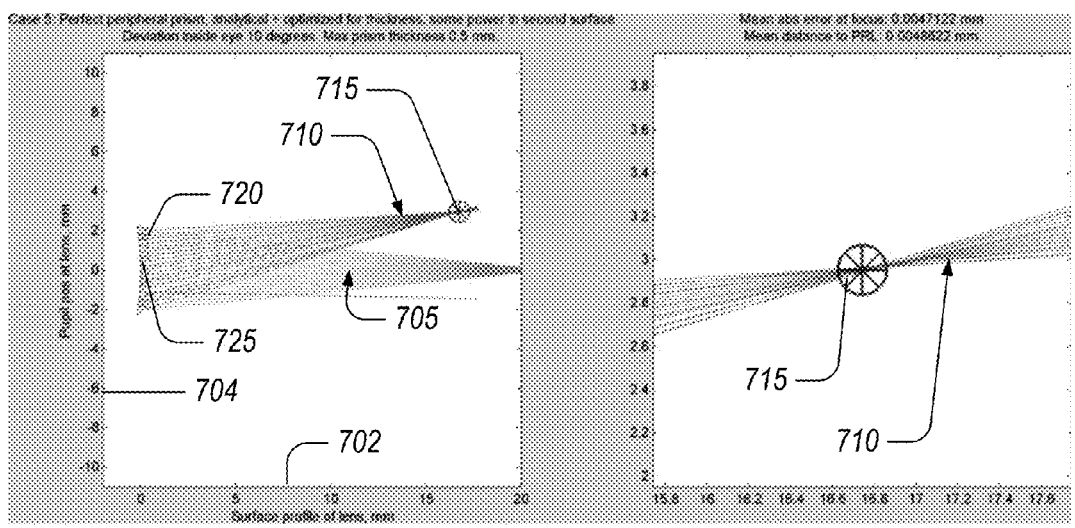
FIG. 18 illustrates a plot and a zoomed-in version of the plot showing ray convergence and image focus at a PRL when redirecting incident light using a tailored redirection element having an iteratively tuned slope profile.

Accordingly, the second step of the general analytical method is to perform an iterative procedure to adjust the slope profile of the surface of the redirection element. This can be accomplished by beginning at an initial point in a Fresnel zone, updating the slope profile, and then integrating to get the surface shape. Beginning with the analytical expression for the slope profile (e.g., Equation (3)), the height is calculated at each part on the IOL. This can be done in a single dimension, the dimension of redirection. For each part of the IOL, the actual ray is calculated and compared to the desired ray (e.g., the ray that would exactly intersect the PRL). Where there is a difference between the actual ray and the desired ray, the slope is adjusted to get the desired ray. Next, the slope profile is recalculated. The recalculated slope profile provides a better image which may be improved with additional iterations. The iterative procedure can be stopped when one or more parameters indicative of image quality are within a designated, targeted, or desired range. This iterative procedure is referred to in FIG. 21, and specifically referred to in block 1920. In this way, image quality at the PRL can be improved or optimized via a gradual adjustment of the slopes provided by the analytical expression described herein above. FIG. 18 illustrates image quality at the PRL when the iterative procedure is performed on the redirection element of FIG. 17. In this case, the mean absolute transversal error at the focus is about 0.0047 mm and the mean ray distance to the PRL 715 is about 0.0048 mm, far superior to the optical quality provided by Fresnel prisms with a constant slope, as exemplified in FIG. 12.

Figure 19:
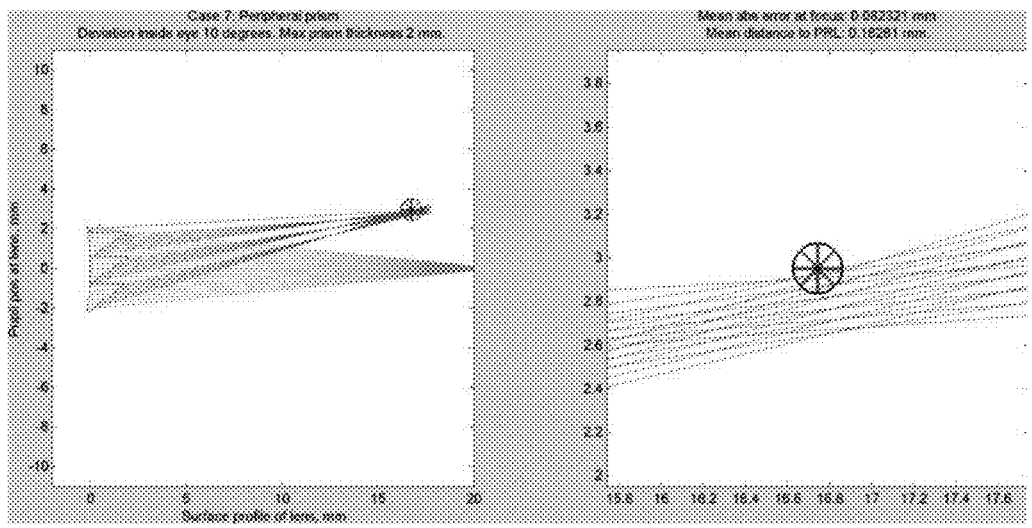
FIG. 19 illustrates a plot and a zoomed-in version of the plot showing ray convergence and image focus at a PRL when redirecting incident light using a Fresnel prism having an increased thickness and fewer Fresnel zones, a redirection element including zones of constant slope, the slope profiles based on analytical computations.
Figure 20:
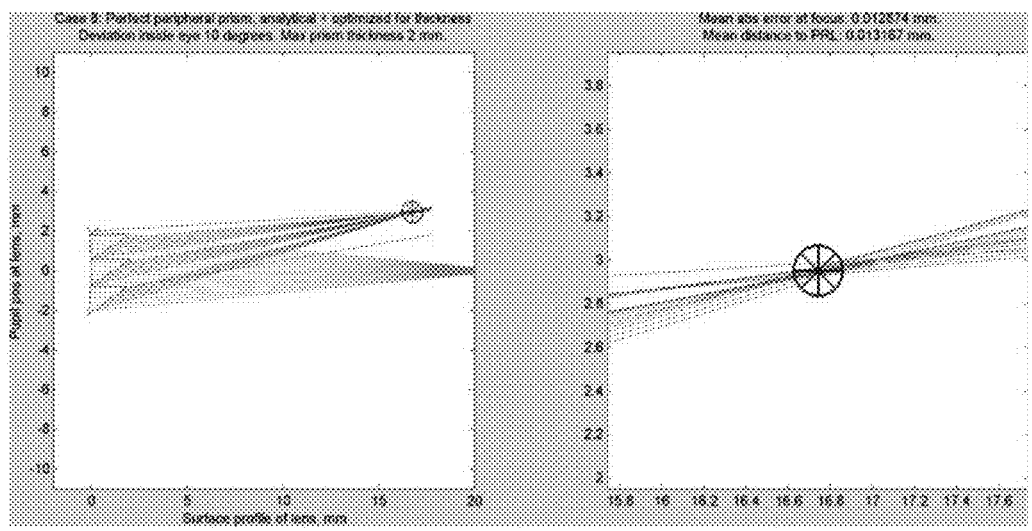
FIG. 20 illustrates a plot and a zoomed-in version of the plot showing ray convergence and image focus at a PRL when redirecting incident light using a redirection element having an increased thickness and fewer Fresnel zones, the redirection element having an iteratively tuned slope profile.
Figure 21:
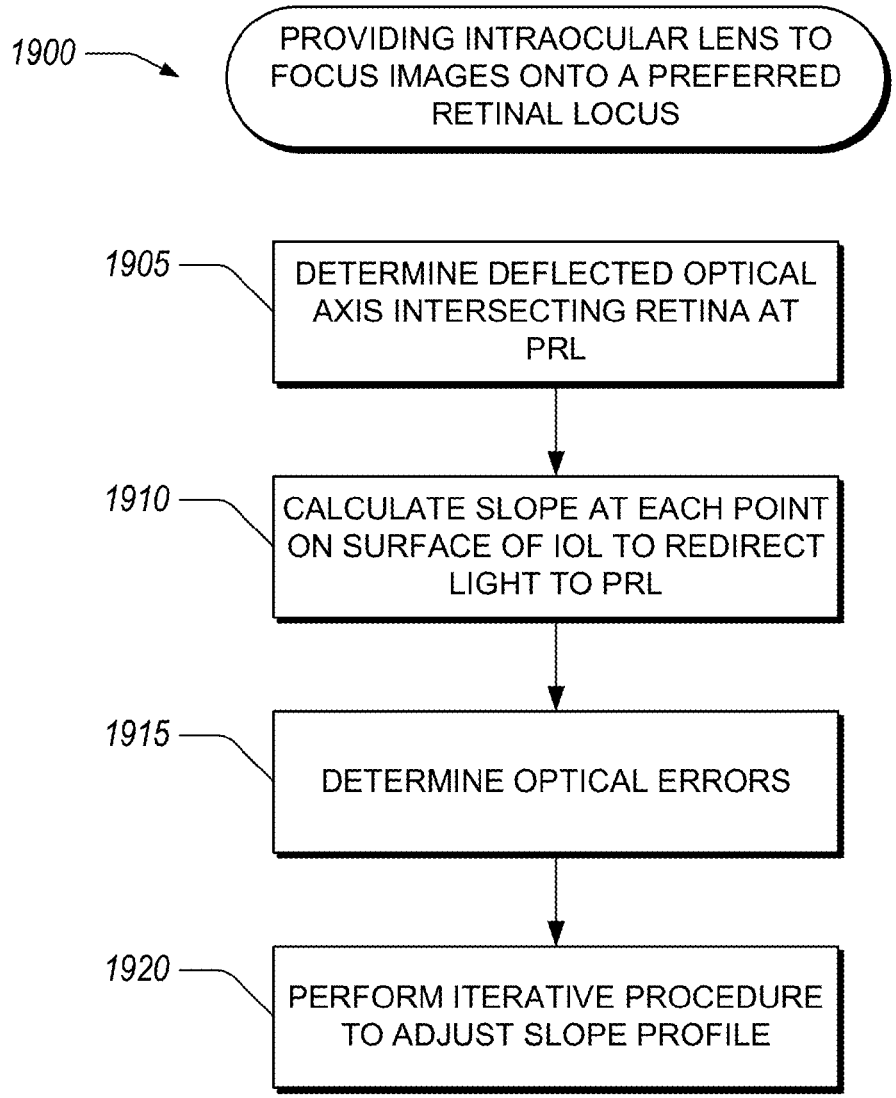
FIG. 21 illustrates an example method for providing an intraocular lens to focus images onto a peripheral retina locus.
Figure 22:
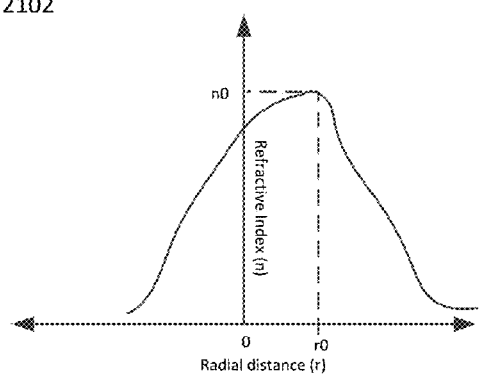
FIG. 22 illustrates an example of an asymmetric refractive index profile for an optical component that can be included in an ophthalmic device that is capable of deflecting light away from the fovea to the PRL.

In some embodiments, the general analytical method can be applied to a Fresnel prism that is thicker and that has fewer Fresnel zones than the previously shown prisms. One such example is illustrated in FIGS. 21 and 22, which shows Fresnel prisms with a maximum thickness of 2 mm and slope profiles respectively configured as those in FIGS. 18, and 19. In particular, the redirection element in FIG. 19 represents a tailored redirection element with a slope that varies according to the analytical expression described herein above. The redirection element in FIG. 20 represents a redirection element with a tailored slope profile that has been modified according to the iterative procedure of the second operation of the general analytical method, described herein above. The mean absolute transversal errors at the focus of FIGS. 21-22 are respectively about 0.082 mm, and 0.013 mm. The mean ray distance to the PRL 715 of FIGS. 21-22 are respectively about 0.16 mm, and 0.013 mm.

The tailored redirection elements incorporating the slope profiles determined using the above described general analytical method demonstrate improved image quality at large and small eccentricities, when compared to simple prisms and simple Fresnel prisms. Based at least in part on the density of retinal ganglion cells being higher at more central parts of the retina, the improved image quality provided by the tailored redirection elements can be useful at substantially all eccentricities within the eye (e.g., from a few degrees to about 30 degrees).

In some embodiments, the general analytical method can be based on an absolute value of the deflection angle requested or desired. When incorporated into a patient's eye, then, the IOL can be rotated so that the deflected optical axis intersects the retina at the PRL (e.g., where the relative position of the PRL is nasal, temporal, inferior, superior, or a combination of these). In some embodiments, the general analytical method can be applied to correcting small deflections or eccentricities in LASIK nomograms directed to treating patients with central vision loss (e.g, due to AMD).

FIG. 21 illustrates an example method 1900 for providing an IOL to focus images onto a PRL. The IOL can be configured to include a redirection element that redirects incident light to the PRL. The redirection element can be incorporated onto the IOL or at any other suitable location to accomplish the redirection in cooperation with the IOL. The method 1900 can be configured to provide focused light at the PRL while reducing or minimizing aberrations at the PRL relative to simply redirecting light to the PRL using a typical prism or equivalent design. The method 1900 can include performing the operations of the general analytical method described herein above.

In block 1905, a deflected optical axis is determined which intersects a PRL of a patient at the retina. The deflected optical axis can be considered to be deflected from the natural optical axis 280 of the eye, as illustrated in FIG. 1. The deflected optical axis can be configured to intersect the patient's retina at the PRL such that light directed along the deflected optical axis and focused onto the patient's PRL can be resolved by the patient instead of being directed along the natural optical axis and focused onto a damaged portion of the retina.

As described herein with reference to FIG. 10, and particularly with reference to block 605, block 1905 can include determining the PRL of a patient. The techniques, systems, methods, and considerations described herein above also apply here.

In operational block 1910, a slope is determined for points on a surface of the IOL, wherein the slope at each of these points is configured to redirect light to the PRL and/or along the deflected optical axis determined in block 1905. The determined slope can be applied to a redirection element that is incorporated onto the IOL or implanted at any other suitable location in the eye. Based at least in part on Snell's law, the location of the PRL, and properties of the patient's eye, an analytical expression can be found for the slope as a function of radial position. In some embodiments, the analytical expression is equivalent to the formula presented in Equation (3) above. Examples of slope profiles 1005 calculated with Equation (3) are shown and described herein above with reference to FIGS. 14-16. In some embodiments, the slope can be determined using a variety of input parameters including, for example and without limitation, the eccentricity (e.g., angle), the axial eye length and the radius of curvature of the retina (e.g., the eye length to the PRL), the IOL position, the power of the cornea, or the like. These and like input parameters can be used to determine optical errors, e.g., in block 1915, and/or in the iterative procedure to reduce the optical errors in block 1920.

Returning to FIG. 21, in operational block 1915, optical errors are determined based on the slope profiles calculated in block 1910. The optical errors can include, for example and without limitation, astigmatism, coma, spherical aberrations, field curvature, etc. The optical errors can include the mean absolute transversal errors at the focus and/or the mean ray distance to the PRL.

In operational block 1920, an iterative procedure is performed to adjust the slope profile. In some embodiments, the slope profile can be applied to a segmented redirection element, where the slope in each segment corresponds to the slope profile calculated for that surface position. The iterative procedure can be configured to account for the effects of the thickness of the redirection element incorporating the determined slope profile. The iterative procedure can be configured to reduce the optical errors determined in block 1915. The iterative procedure includes beginning at an initial point in a zone, updating the slope profile, and then integrating to get the surface shape. Beginning with the analytical expression for the slope profile (e.g., Equation (3) which assumes a thickness of 0 for the redirection element), the height is calculated at each part on the IOL. This represents a height relative to the surface of the IOL, for example. To simplify this procedure, this can be done in the dimension of redirection (e.g., a single dimension). For each part of the IOL, the actual ray is calculated and compared to the desired ray (e.g., the ray that would exactly intersect the PRL). The two rays may differ based at least in part on the thickness of the redirection element (which may be not initially accounted for in the solution to the analytical problem described herein). Where there is a difference between the actual ray and the desired ray, the slope is adjusted to get the desired ray. Next, the slope profile is recalculated (e.g., the height above the surface of the IOL, or the thickness of the redirection element). The recalculated slope profile provides a better image which may be improved with additional iterations. The iterative procedure can be repeated until one or more parameters indicative of image quality are within a designated, targeted, or desired range. Simulated results of applying this iterative procedure to a tailored redirection element incorporated onto a posterior surface of an IOL are shown in FIG. 18, demonstrating a significant improvement in focus at the PRL relative to a redirection element which has not been tailored according to the method 1900.

Ophthalmic Device with Decentered Gradient Refractive Index (GRIN)

As discussed above, patients suffering from AMD can benefit from ophthalmic solutions (e.g., IOLs, contact lenses, spectacles, etc.) that can deflect and focus light away from the fovea 260 at a PRL. Patients suffering from retinal scotoma or at risk for retinal scotoma also have regions of decreased visual acuity and/or contrast sensitivity in the central visual field and can also benefit from such ophthalmic solutions. Ophthalmic devices including an optical component whose refractive index varies gradually can be employed to deflect light away from the fovea 260 to the PRL 290 and improve vision in patients with AMD or retinal scotoma. The refractive index can vary axially, radially, angular or spherically. In order to deflect incident light such that it is focused at the PRL 290 instead of the fovea 260, the variation of the refractive index profile of the optical component is asymmetric about an axis of rotational symmetry of the ophthalmic device. FIG. 22 illustrates an example of an asymmetric refractive index profile along one meridian for an optical component that can be included in an ophthalmic device that is capable of deflecting light away from the fovea 260 to the PRL 290. In FIG. 22, the axis of rotational symmetry passes through the origin at r=0. The optical component has the maximum refractive index n0 in a region that is offset from the origin r=0. Accordingly, the refractive index profile is decentered (or asymmetric) with respect to the axis of rotational symmetry. In various embodiments, the optical component can be a Gradient refractive-index (GRIN) optic having a gradual variation of the refractive index of a material.

Figure 23:
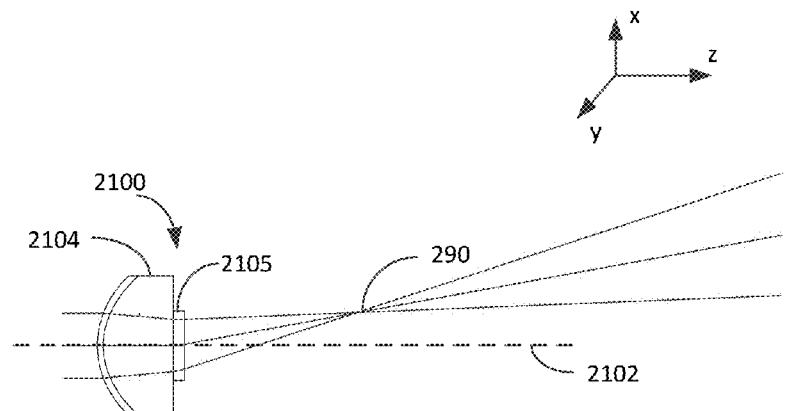
FIG. 23 illustrates an embodiment of an ophthalmic device including an optical component with a gradient refractive index (GRIN) profile.

FIG. 23 illustrates an embodiment of an ophthalmic device 2100 including an optical lens 2104 and an optical component 2105 with a GRIN profile. The optical component 2105 has a GRIN profile that is decentered about an axis 2102 of the ophthalmic device 2100. The GRIN profile can be decentered perpendicular to (e.g., along the x-axis and/or along the y-axis) the axis 2102. The axis 2102 can represent the axis along which the lens 2104 is rotationally symmetric. Accordingly, the optical component 2105 is capable of deflecting and focusing incident light away from the fovea 260 at the PRL 290. The optical component 2105 can be a flat lens as shown in FIG. 23. In some embodiments, the optical component 2105 can include a SELFOC™ lens wherein the refractive index varies radially (e.g., in the x-y plane) and is offset and/or decentered from the axis 2102. In certain embodiments, the optical component 2105 is disposed on a proximal surface of the lens 2104, and more generally can be the proximal-most focusing element in the eye. In various embodiments, the GRIN profile can vary axially (e.g., along the z-axis) and be decentered with respect to the axis 2102. In various embodiments, the GRIN profile can vary radially (e.g., in the x-y plane) and be decentered with respect to the axis 2102. In some embodiments, the refractive index profile can vary elliptically or sinusoidally along the axis 2102. In some embodiments, the refractive index profile can tapered gradient along the axis 2102.

In some embodiments, the optical component 2105 can have a refractive index profile as given by the equation (4) below:

$$n(r')=n_0\sqrt{2-(r'/nr_1)^2} \qquad (4)$$

In various embodiments, the variable r' can be given by the equation (5) below:

$$r'(z)=\sqrt{x^2+y^2+(z-sgc)^2} \qquad (5)$$

The terms $nr_1$ and sgc are constants that can be selected to obtain a desired refractive index profile. The term sgc is a measure of the focal length of the ophthalmic device 2100.

Figure 24:
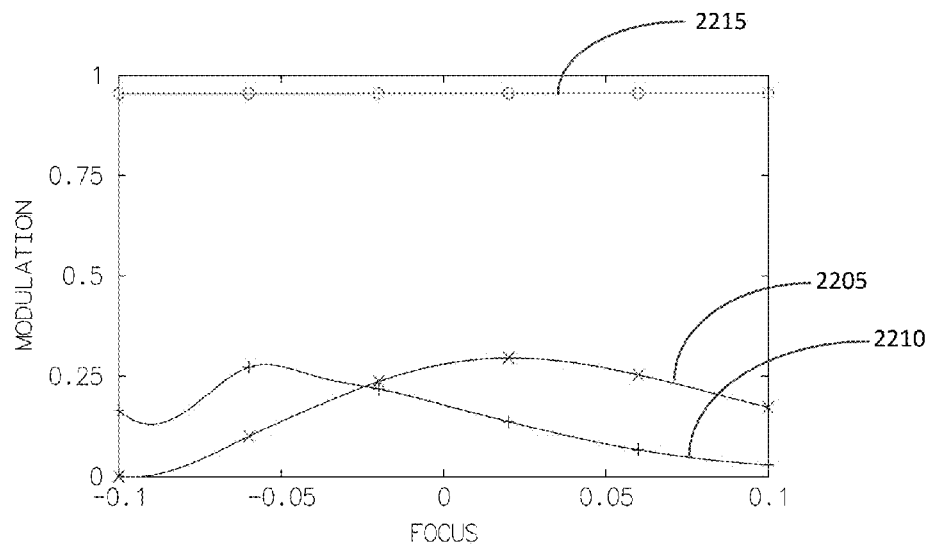
FIG. 24 shows the optical output from the ophthalmic device depicted in FIG. 19.

FIG. 24 shows the optical output from the ophthalmic device 2100. In particular, FIG. 24 illustrates the calculated through focus modulation transfer function (MTF) along the line of deflection for the ophthalmic device 2100 as a function of the focal position. The MTF can be calculated (or simulated) using an optical simulation program such as, for example, OSLO, ZEMAX, CODE V, etc. Curve 2205 shows the variation of the MTF with respect to the focal position for sagittal rays. Curve 2210 shows the variation of the MTF with respect to the focal position for tangential rays. Curve 2215 is the maximum MTF achievable by the ophthalmic device 2100. The theoretical maximum MTF can be calculated by ray trace analysis using an optical simulation program such as, for example, OSLO, ZEMAX, CODE V, etc. Curves 2205 and 2210 are obtained by setting the value of $nr_1$ to 2 in equation (4) and the value of sgc to 17 mm in equation (5), and decenter the GRIN profile by about 3 mm perpendicular to the optical axis 2102. In various implementations, the GRIN profile can be decentered such that the center of the GRIN profile is located towards an edge of the ophthalmic device 2100 along the radial direction. As observed from FIG. 24, the maximum MTF for both sagittal and tangential rays occurs at a non-zero focal position indicating that both for sagittal and tangential rays the MTF may be further optimized. The optical output from the ophthalmic device 2100 can be modified by selecting other values for the variables $nr_1$ and sgc in combination with selecting different parameters for the optical lens 2404 and/or the optical component 2105 such as, for example, curvature of the anterior and posterior surfaces of the lens 2404 and/or the optical component 2105, spherical aberration, amount of and direction along which the refractive index is decentered (e.g. along the x-direction or the y-direction or both), etc.

In some embodiments, the optical component 2105 can have a refractive index profile as given by the equation (6) below:

$$n^2(r) = n_0^2[1 - (nr_1 r)^2 + nr_2(nr_1 r)^4 + nr_3(nr_1 r)^6 + nr_4(nr_1 r)^8] \quad (6)$$

In various embodiments, the variable r can be given by the equation (7) below:

$$r = \sqrt{x^2 + y^2} \quad (7)$$

The terms $nr_1$, $nr_2$, $nr_3$, and $nr_4$ are constants that can be selected to obtain a desired refractive index profile. For example, in some embodiments, the term $nr_1$ can be equal to 0.12, the term $nr_2$ can be equal to 0.24 and the term $nr_3$ can be equal to −0.2, and nr4 can be equal to zero and the GRIN profile can be decentered perpendicular to the axis 2102 by about 3 mm. The optical output may be further optimized by modifying the values of nr1, nr2, nr3 and nr4 and the amount of decentration.

The ophthalmic device 2100 including the optical component 2105 with a GRIN profile can include a marking to indicate an orientation of the ophthalmic device 2100 or a direction of the gradient of the refractive index of optical component 2105. The ophthalmic device 2100 can be rotated to achieve a desired orientation and position of the marking when disposed with respect to the structures of the eye to ensure that incident light is focused at the PRL 290.

In various embodiments, the optical lens 2104 can be an intraocular lens that can provide base optical power and/or add power. The optical lens 2104 can be an intraocular lens implanted in the eye, a spectacle lens or a contact lens. In such embodiments, the optical component 2105 can be configured as a piggyback lens or as an add-on to the optical lens 2104.

Ophthalmic Device with Diffraction Grating and Achromatic Diffractive Surface

Figure 25:
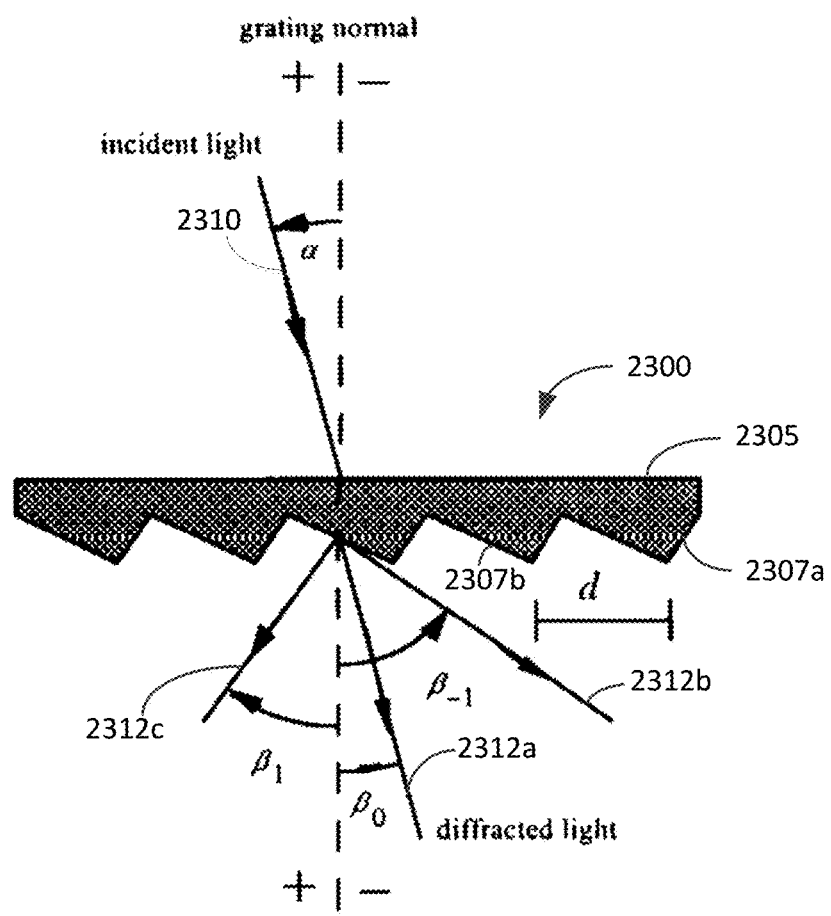
FIG. 25 illustrates an example implementation of a linear grating.

A diffraction grating can be used to direct light incident from a first direction along a second direction different from the first direction. A diffraction grating includes a plurality of diffracting structures such as a groove, a slit, a lenslet, etc. The second direction along which the incident light is diffracted depends on the spacing between the plurality of diffractive structures and the wavelength of light. FIG. 25 illustrates an example implementation of a linear grating 2300. The grating 2300 comprises a substrate 2305 including a plurality of diffracting structures (e.g., 2307a and 2307b). The distance, 'd', between consecutive diffracting structures 2307a and 2307b is referred to as the grating period. Incident light beam represented by ray 2310 that is incident from a direction that is at an angle α from a normal to the substrate 2305 is diffracted into several outgoing light beams 2312a, 2312b and 2312c traveling in different directions that make an angle $\beta_0$, $\beta_1$, and $\theta_{-1}$ respectively with the normal to the substrate 2305. The different directions $\beta_0$, $\beta_1$, and $\beta_{-1}$ are determined from the grating equation $m\lambda = d(\sin \alpha + \sin \beta_m)$, where m is an integer and is referred to as the diffraction order. Accordingly, an ophthalmic device including a grating (e.g., grating 2300) can be used to deflect incident light away from the fovea 260 and focus it at the PRL 290. For example, light incident at normal incidence making an angle close to or equal to zero degrees with a normal to the substrate 2305 can be deflected by an angle between about 5-10 degrees, for example, an angle of 7.3 degrees or an angle of about 8.3 degrees by a diffraction grating having a grating period d between about 3 and 10 microns, for example, 4 micron or 6 micron, for diffraction order m=2.

Figure 26:
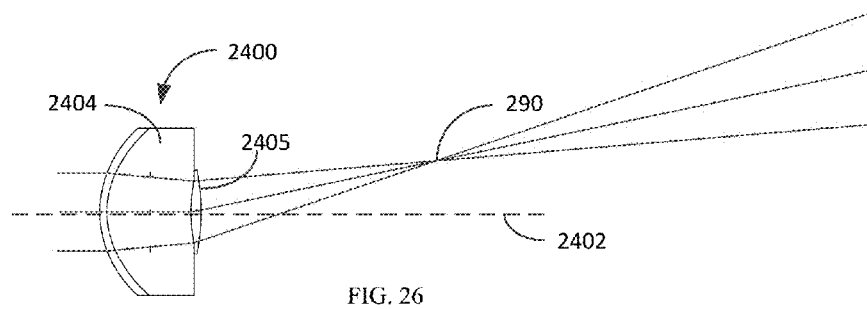
FIG. 26 illustrates an embodiment of an ophthalmic device including an embodiment of a diffraction grating.

FIG. 26 illustrates an embodiment of an ophthalmic device 2400 including an optical lens 2404 and an embodiment of a diffraction grating 2405. In various embodiments, the diffraction grating 2405 can be a linear grating. The diffraction grating 2405 preferably is configured to be disposed as close to the retina as possible, e.g., on the posterior surface of the lens 2404 or adjacent to an anterior surface of the inside posterior layers of an evacuated capsular bag. The diffraction grating 2405 includes a plurality of diffracting structures having a grating period, d, between about 1 micron and about 20 microns, for example, the grating period, d, can be 4 micron or 6 micron. The ophthalmic device 2400 including the diffraction grating 2405 can deflect incident light by about 4-10 degrees, for example, 5.3 degrees, 7.9 degrees or 8.3 degrees such that incident light is deflected away from the fovea and focused at the PRL 290.

The ophthalmic device 2400 including the diffraction grating 2405 can include a marking to indicate an orientation of the ophthalmic device 2400. The ophthalmic device 2400 can be rotated to achieve a desired orientation and position of the marking when disposed with respect to the structures of the eye to ensure that incident light is focused at the PRL 290.

Figure 27:
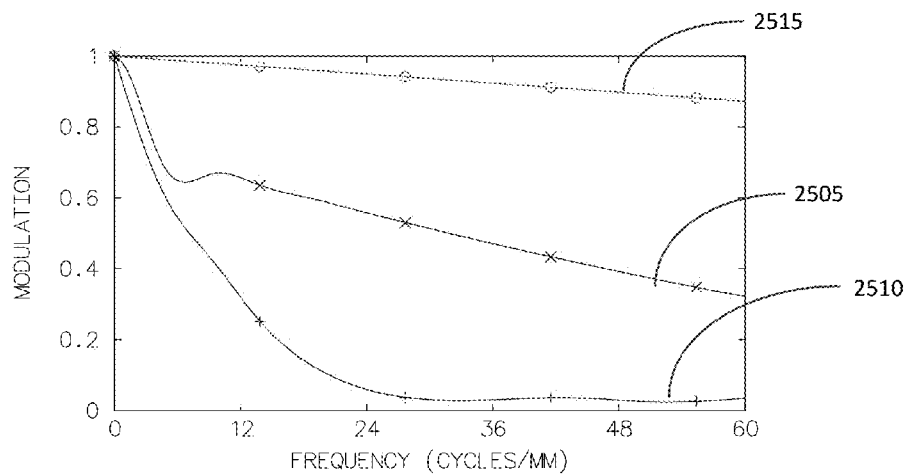
FIG. 27 shows the optical output from an embodiment of an ophthalmic device including a polychromatic diffraction grating.

FIG. 27 shows the polychromatic optical output from an embodiment of the ophthalmic device 2400 including a linear diffraction grating having grating period of 6 microns. The linear grating includes a diffracting structure designed for a central wavelength (e.g., 550 nm) to deflect light to the second diffraction order. In particular, FIG. 27 illustrates the calculated modulation transfer function (MTF) for the ophthalmic device 2400 as a function of spatial frequency at a preferred location of the peripheral retina. In various implementations, the PRL can correspond to the position on the peripheral retina where incident ambient light is best focused by the ophthalmic device 2400. Curves 2505 and 2510 shows the variation of the MTF for polychromatic light (e.g., white light) incident at normal incidence making an angle close to or equal to zero degrees with a normal to the substrate 2305 that is diffracted into the second order (m=2) for sagittal rays and tangential rays. Curve 2515 is the theoretical maximum MTF (as calculated by ray trace analysis using an optical simulation program) achievable by the embodiment of the ophthalmic device 2400. When calculating curves 2505 and 2510, the grating is configured to have a tilt of about 3 degrees.

The angle at which light is diffracted by a diffraction grating (e.g., diffraction grating 2300) depends on the wavelength of incident light, diffraction order and grating period. Moreover, the fraction of light diffracted into any order, which is the efficiency of the grating in that order, is not same for all wavelengths. Generally, the efficiency of a grating can be adjusted by changing the geometry (e.g., facet angles, shape and/or depth) of the diffracting features 2312a, 2312b and 2312c. The operation of optimizing the grating efficiency by changing the shape of the diffracting features is referred to as blazing. As observed from FIG. 27, different wavelengths of light are diffracted into the second order with different efficiencies such that the MTF for tangential rays drops below 0.2 as the spatial frequency increases beyond 12 cycles/mm. Since, the ophthalmic device 2400 is configured to be disposed with respect to the structures of the eye and used to view illuminated by or emitting light in the visible spectral, it is advantageous if all wavelengths in white light are diffracted in a grating order with substantially the same efficiency. In other words, it would be advantageous if the MTF for both sagittal and tangential rays when deflected to the PRL 290 had a MTF above a threshold (e.g., MTF greater than 0.2) for all wavelengths of light in the visible spectrum.

Including an achromatic optical component can advantageously increase the efficiency for different wavelengths diffracted into a grating order. The achromatic optical component is designed to reduce the effects of chromatic aberration. The achromatic optical component is configured such that the focal points for two different wavelengths (e.g., red and blue) are in the same plane. For instance, the achromatic optical component is configured such that the focal points for two different wavelengths (e.g., red and blue) coincide at the PRL 290. The achromatic optical component can include an achromatic diffractive surface, an achromatic lens, such as, for example, a Littrow doublet, a Fraunhofer doublet, a Clark doublet, etc.

Figure 28:
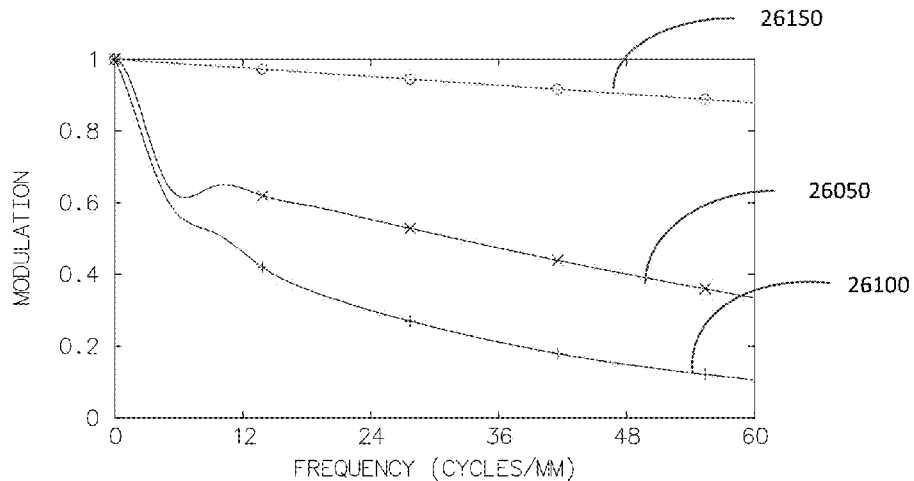
FIG. 28 shows the optical output from an embodiment of an ophthalmic device including a polychromatic diffraction grating and an achromatic optical component.

FIG. 28 shows the optical output from an embodiment of ophthalmic device 2400 including a linear diffraction grating having grating period of 6 microns and an achromatic diffractive surface. In particular, FIG. 28 illustrates the calculated modulation transfer function (MTF) for the ophthalmic device 2400 including a linear diffraction grating and an achromatic diffractive surface as a function of spatial frequency at best focus position, i.e. at the location of the PRL. Curves 26050 and 26100 shows the variation of the MTF for polychromatic light (e.g., white light) incident at normal incidence making an angle close to or equal to zero degrees with a normal to the substrate 2305 that is diffracted into the second order (m=2) for sagittal rays and tangential rays. Curve 26150 is the theoretical maximum MTF (as calculated by ray trace analysis using an optical simulation program) achievable by the embodiment of the ophthalmic device 2400 including a linear diffraction grating and an achromatic diffractive surface When calculating curves 26050 and 26100, the grating is configured to have a tilt of about 3 degrees.

A comparison of FIGS. 27 and 28 shows that the inclusion of the achromatic optical component can increase the efficiency with which different wavelengths are focused at the PRL 290 such that the MTF for tangential rays is greater than 0.2 for spatial frequencies up to 36 cycles/mm indicating improved image quality at the PRL. The efficiency with which different wavelengths are focused at the PRL 290 can be further increased by including additional optical component such as filters, by changing the shape of the diffracting features and/or by changing other features of the ophthalmic device 2400 such as refractive index of the materials of the lens 2404 and/or the optical component 2405, radius of curvatures for the anterior and posterior surfaces of the lens 2404 and/or the optical component 2405, shape factor of the lens 2404, asphericity of the lens 2404, etc.

In various embodiments, the optical lens 2104 can be an intraocular lens that can provide base optical power and/or add power. The optical lens 2104 can be an intraocular lens implanted in the eye, a spectacle lens or a contact lens. In such embodiments, the optical component 2105 can be configured as a piggyback lens or as an add-on to the optical lens 2104.

Example IOLs with Redirection Elements

In some embodiments, the redirection elements described herein (e.g., tailored redirection elements, diffraction gratings, decentered GRIN etc.) can be applied on top of an existing IOL, where it can be added, for example and without limitation, using a ring structure; as a separate, additional surface; put directly on top of a previous IOL; or the like. Such a configuration could allow a person who had previously undergone cataract surgery to benefit from the redirection element if the person later loses central vision capabilities (e.g., due to AMD).

In some embodiments, the redirection elements described herein (e.g., tailored redirection elements, diffraction gratings, decentered GRIN lenses, etc.) can utilize materials of a higher index of refraction than the IOL into which they are incorporated. This may enable the redirection elements to be made even smaller (e.g., having a smaller thickness) which can reduce optical aberrations.

In some embodiments, the redirection elements described herein (e.g., tailored redirection elements, diffraction gratings, decentered GRIN lenses, etc.) can cover a portion of the IOL (e.g., at least about 1.5 mm and/or less than about 4.5 mm in diameter, or at least about 2 mm and/or less than about 3 mm, or about 2.5 mm). Such a configuration can be advantageous for haptics, insertion, manufacturing, leaving parts of the visual field undeflected (e.g., as with the dual-zone IOL described herein), allowing use of retinal locations that are not at the PRL, etc.

In some embodiments, the redirection elements described herein (e.g., tailored redirection elements, diffraction gratings, decentered GRIN lenses, etc.) can be incorporated into the IOL on multiple surfaces (e.g., the anterior and/or posterior surfaces). It may be advantageous to position the redirection element on the posterior surface of the IOL to improve or optimize image quality. However, if physical constraints limit placement options, the redirection element can be placed at all other available locations where implants can typically be positioned.

In some embodiments, an IOL can be configured to include a plurality of redirection elements, such as the tailored redirection elements or any of the other described redirection elements described herein, to redirect light to a corresponding plurality of PRLs. For example, a first redirection element can be configured to redirect incident light to a first PRL and a second redirection element can be configured to redirect incident light to a second PRL.

In some embodiments, the redirection elements described herein, e.g., the tailored redirection element, can be implanted bilaterally to restore binocular vision. The redirection of each eye can be calculated (e.g., by finding a PRL for each eye) and tailored redirection elements can be implanted in each eye to shift the positions of the images of each eye to their respective PRLs. This can allow a patient to look straight ahead and have the image at the PRL of both eyes, allowing the patient to utilize binocular vision which is typically lost in patients suffering from central vision loss.

Example IOL Design System

Figure 29:
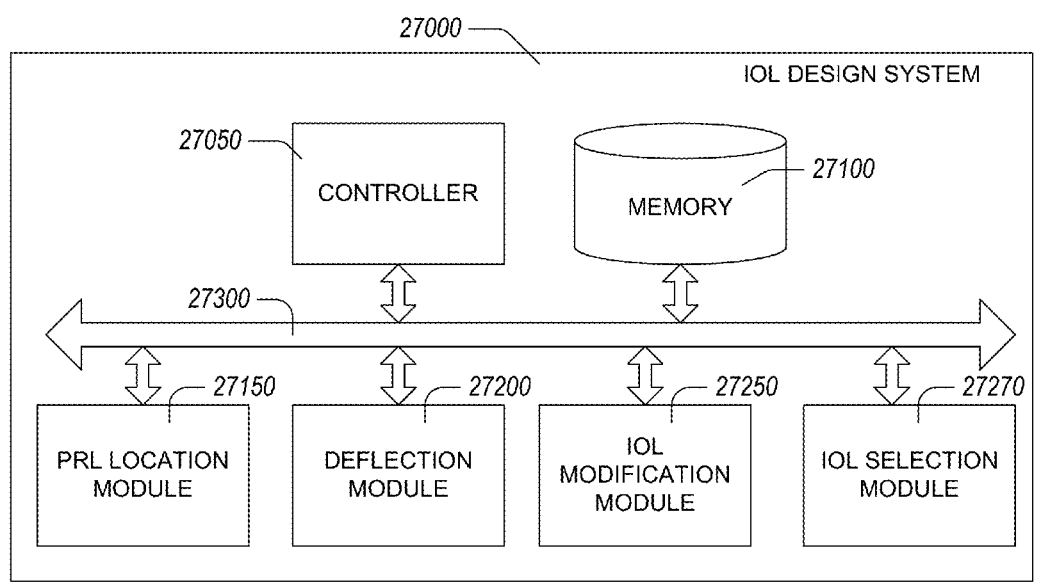
FIG. 29 illustrates a block diagram of an example IOL design system for determining properties of an intraocular lens configured to improve overall vision where there is a loss of central vision.

FIG. 29 illustrates a block diagram of an example IOL design system 27000 for determining properties of an intraocular lens configured to improve vision at a peripheral retinal location. The IOL design system 27000 includes a controller 27050 and a computer readable memory 27100 coupled to the controller 27050. The computer readable memory 27100 can include stored sequences of instructions which, when executed by the controller 27050, cause the IOL design system 27000 to perform certain functions or execute certain modules. For example, a PRL location module 27150 can be executed that is configured to determine a location of one or more PRLs for a particular patient. As another example, a deflection module 27200 can be executed that is configured to determine a deflected optical axis which intersects the determined PRL location at the retina. As another example, an IOL modification module 27250 can be executed that is configured to determine properties of the IOL which would deflect at least a portion of incident light along the determined deflected optical axis to the determined PRL. As another example, an IOL selection module 27270 can be executed that is configured to select an appropriate or candidate IOL provided one or more selection parameters including, for example and without limitation, PRL location and a patient's biometric data.

The PRL location module 27150 can be configured to determine one or more candidate PRL locations using analytical systems and methods designed to assess retinal sensitivity and/or retinal areas for fixation. For example, the PRL location module 27150 can provide or interface with a system configured to provide a patient with stimuli and to image the patient's retina to assess topographic retinal sensitivity and locations of preferred retinal loci. An example of such a system is a microperimeter which can be used to determine a patient's PRL by presenting a dynamic stimulus on a screen and imaging the retina with an infrared camera. Another example of such a system, a laser ophthalmoscope can be used to assess a retinal area used for fixation (e.g., using an infrared eye tracker) which can be used to determine discrete retinal areas for fixation for various positions of gaze.

The PRL location module 27150 can be configured to bypass the optics of the patient. In some instances, optical errors induced by a patient's optics can cause the patient to select a non-optimal PRL or a PRL which does not exhibit benefits of another PRL, e.g., where a patient selects an optically superior but neurally inferior region for the PRL. Accordingly, the PRL location module 27150 can advantageously allow the identification of a PRL which, after application of corrective optics (e.g. the IOLs described herein), would provide superior performance compared to a PRL selected utilizing a method which includes using the patient's optics. This may arise where the corrective optics reduce or eliminate the optical errors which are at least a partial cause for a patient selecting a sub-optimal PRL.

The PRL location module 27150 can be configured to determine multiple candidate locations for the PRL. The preferred or optimal PRL can be based at least upon several factors including, for example and without limitation, a patient's ability to fixate a point target, distinguish detail, and/or read; aberrations arising from redirecting images to the candidate PRL; proximity to the damaged portion of the retina; retinal sensitivity at the candidate location; and the like. The preferred or optimal PRL can depend on the visual task being performed. For example, a patient can have a first PRL for reading, a second PRL when navigating, and a third PRL when talking and doing facial recognition, etc. Accordingly, multiple PRLs may be appropriate and an IOL can be configured to redirect incident light to the appropriate PRLs using multiple zones and/or multiple redirection elements, as described herein. For example, an IOL can be provided with two or more zones, with one or more zones redirecting light to a designated PRL, where the zone can be configured to have additional optical power or no additional optical power.

The deflection module 27200 can be configured to assess the properties of the eye and to determine a deflected optical axis which intersects the patient's retina at a PRL. The deflection module 27200 can be configured to account for the removal of the natural lens, the optical properties of the cornea, the shape of the retina, the location of the PRL, axial distance from the cornea to the PRL and the like to determine the angle of deflection from the eye's natural optical axis (e.g., the optical axis of the natural lens, the optical axis of the eye without an IOL, etc.). In some embodiments, the deflection module 27200 can be configured to determine aberrations arising from deflecting incident light along the deflected optical axis. The aberrations can include astigmatism, coma, field curvature, etc. The determined aberrations can be used in the process of refining or tailoring the design of the IOL, where the IOL is configured to at least partially correct or reduce the determined aberrations.

The IOL modification module 27250 can be configured to determine adjustments, modifications, or additions to the IOL to deflect light along the deflected optical axis and focus images on the PRL. Examples of adjustments, modifications, or additions to the IOL include, without limitation, the optical systems and methods described herein. For example, the IOL can be modified through the introduction of a physical and/or optical discontinuity to deflect and focus light onto the PRL. As another example, one or more redirection elements can be added to one or more surfaces of the IOL to redirect at least a portion of the light incident on the eye to the PRL. The redirection elements can include, for example and without limitation, a simple prism, a Fresnel prism, a redirection element with a tailored slope profile, redirection element with a tailored slope profile tuned to reduce optical aberrations, a diffraction grating, a diffraction grating with an achromatic coating, a decentered GRIN lens, etc. In some embodiments, multiple redirection elements and/or multiple modifications can be made to the IOL, as determined by the IOL modification module 27250, such that the combination of modifications and/or additions to the IOL can be configured to redirect incident light to different PRLs, to direct incident light to different portions of the retina, to provide an optical power which magnifies an image at the retina, or any combination of these functions.

The IOL selection module 27270 can be configured to select the IOL design, power, deflection, orientation, and the like that would provide acceptable or optimal results for a particular patient. The IOL selection can be based at least in part on the patient's biometric inputs. The IOL selection can incorporate multiple considerations. For example, typical IOL power calculation procedures can be used to select the spherical IOL power which can be modified to consider the axial distance from the cornea to the PRL. As another example, customized or additional constants can be developed for AMD patients which provide better results for the patients. The deflection and orientation of the IOL during implantation would be given by the PRL location.

The IOL selection can be based at least in part on ray tracing which can enable a computational eye model of the patient to be generated where the inputs can be the patient's own biometric data. The optical quality can be evaluated considering different IOL deigns and powers, being selected that which optimizes the optical quality of the patient. The optical quality can be evaluated at the PRL or at the PRL and on-axis, for example.

In some embodiments, the IOL selection module 27270 can also comprise a refractive planner which shows patients the expected outcome with different IOL designs and options. This can enable the patient to aid in the decision as to the appropriate IOL design and to come to a quick and satisfactory solution.

The IOL design system 27000 can include a communication bus 27300 configured to allow the various components and modules of the IOL design system 27000 to communicate with one another and exchange information. In some embodiments, the communication bus 27300 can include wired and wireless communication within a computing system or across computing systems, as in a distributed computing environment. In some embodiments, the communication bus 27300 can at least partially use the Internet to communicate with the various modules, such as where a module (e.g., any one of modules 27150, 27200, or 27250) incorporated into an external computing device and the IOL design system 27000 are communicably coupled to one another through the communication bus 27300 which includes a local area network or the Internet.

The IOL design system 27000 may be a tablet, a general purpose desktop or laptop computer or may comprise hardware specifically configured for performing the programmed calculations. In some embodiments, the IOL design system 27000 is configured to be electronically coupled to another device such as a phacoemulsification console or one or more instruments for obtaining measurements of an eye or a plurality of eyes. In certain embodiments, the IOL design system 27000 is a handheld device that may be adapted to be electronically coupled to one of the devices just listed. In some embodiments, the IOL design system 27000 is, or is part of, a refractive planner configured to provide one or more suitable intraocular lenses for implantation based on physical, structural, and/or geometric characteristics of an eye, and based on other characteristics of a patient or patient history, such as the age of a patient, medical history, history of ocular procedures, life preferences, and the like.

Generally, the instructions stored on the IOL design system 27000 will include elements of the methods 2900, and/or parameters and routines for solving the analytical equations discussed herein as well as iteratively refining optical properties of redirection elements.

In certain embodiments, the IOL design system 27000 includes or is a part of a phacoemulsification system, laser treatment system, optical diagnostic instrument (e.g, autorefractor, aberrometer, and/or corneal topographer, or the like). For example, the computer readable memory 27100 may additionally contain instructions for controlling the handpiece of a phacoemulsification system or similar surgical system. Additionally or alternatively, the computer readable memory 27100 may contain instructions for controlling or exchanging data with one or more of an autorefractor, aberrometer, tomographer, microperimeter, laser ophthalmoscope, topographer, or the like.

In some embodiments, the IOL design system 27000 includes or is part of a refractive planner. The refractive planner may be a system for determining one or more treatment options for a subject based on such parameters as patient age, family history, vision preferences (e.g., near, intermediate, distant vision), activity type/level, past surgical procedures.

Additionally, the solution can be combined with a diagnostics system that identifies the best potential PRL after correction of optical errors. Normally, optical errors can restrict the patient from employing the best PRL, making them prefer neurally worse but optically better region. Since this solution would correct the optical errors, it is important to find the best PRL of the patient with a method that is not degraded by optical errors (e.g. adaptive optics). Finally, the solution can be utilized to take advantage of the symmetries that exists with regards to peripheral optical errors in many patients.

Prior to replacing a natural crystalline lens with an IOL, an optical power of the IOL is typically determined. Generally, the on-axis axial length, corneal power of the eye, and/or additional parameters can be used to determine the optical power of the IOL to achieve a targeted refraction with a goal of providing good or optimal optical quality for central/foveal vision. However, where there is a loss of central vision an IOL configured to provide good or optimal optical quality for central vision may result in relatively high peripheral refraction and reduced or unacceptable optical quality at a peripheral location on the retina. Accordingly, systems and methods provided herein can be used to tailor the optical power of an IOL to provide good or optimal optical quality at a targeted peripheral location such as a patient's PRL. The improvement in optical quality at the peripheral retinal location may reduce the optical quality at the fovea, but this may be acceptable where the patient is suffering from a loss in central vision.

Figure 30:
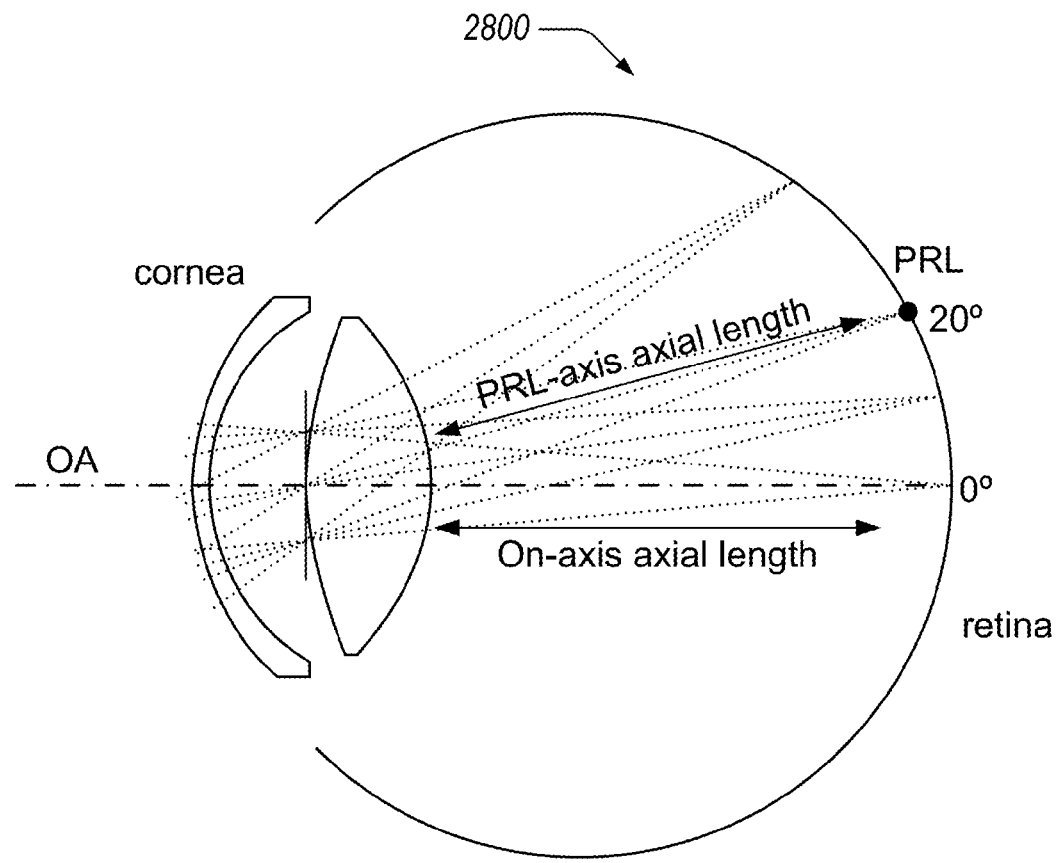
FIG. 30 illustrates parameters used to determine an optical power of an IOL based at least in part on a location of a PRL in a patient.

FIG. 30 illustrates parameters used to determine an optical power of an IOL based at least in part at a peripheral retinal location in an eye 2800. The eye 2800 is illustrated with a PRL location at 20 degrees with respect to the optical axis OA. This can represent an intended post-operative PRL location, where the PRL location is determined as described elsewhere herein. The on-axis axial length (e.g., axial length along optical axis OA) and PRL-axis axial length (e.g., axial length along a deflected optical axis intersecting the retina at the PRL) can be measured for the eye 2800 having the indicated PRL location. In some patients, the axial length in the direction of the PRL can be estimated from the measured on-axis axial length and population averages of ocular characteristics measured using a diagnostic instrument. The ocular characteristics measured using the diagnostic instrument can include pre-operative refraction, corneal power or other parameters. The corneal topography can also be measured (e.g., measurements of the anterior and posterior surfaces of the cornea, thickness of the cornea, etc.) and these measurements can be used, at least in part, to determine the corneal power.

Figure 31A:
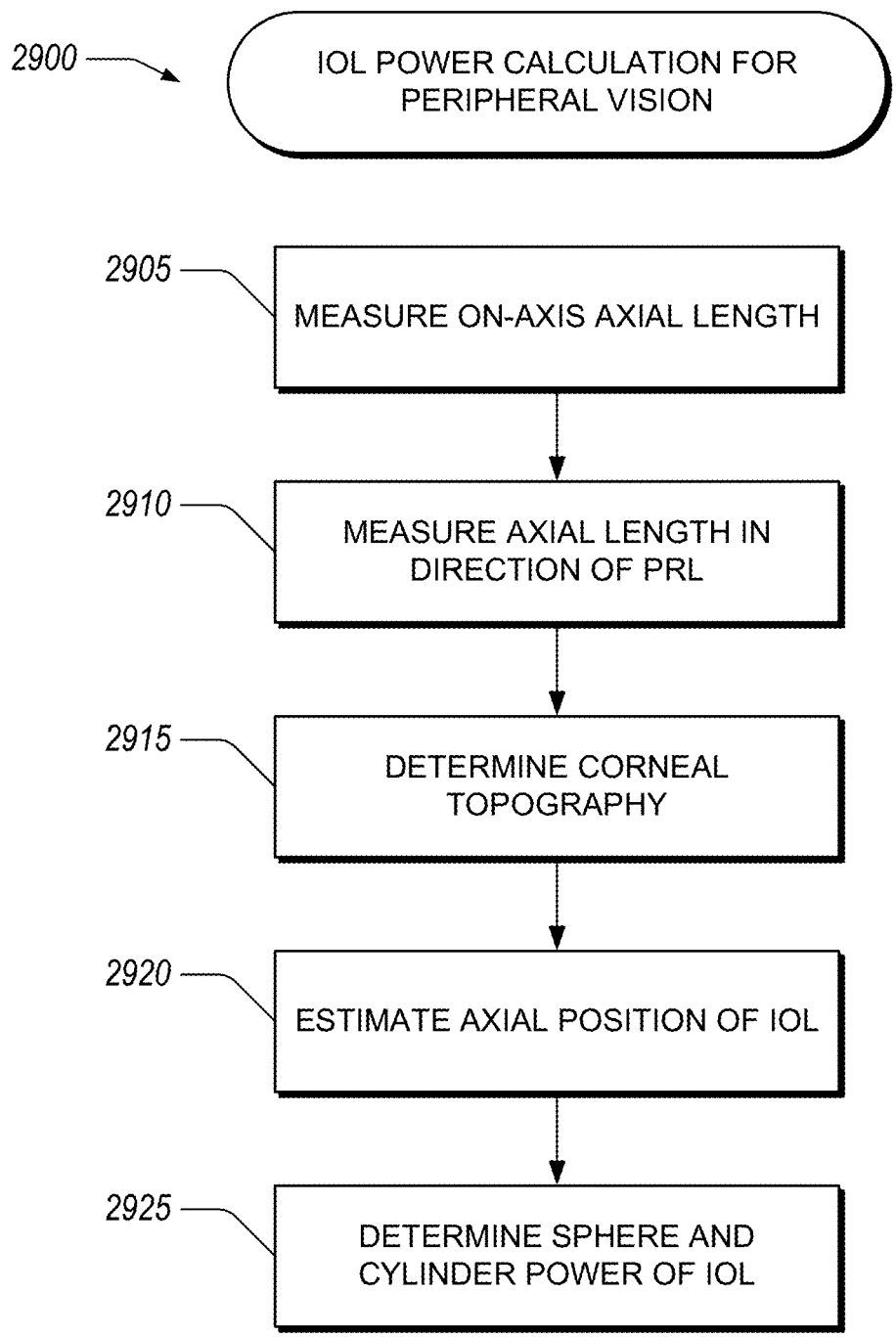
FIG. 31A and FIG. 31B illustrate implementations of a method for determining an optical power of an IOL tailored to improve peripheral vision.
Figure 31B:
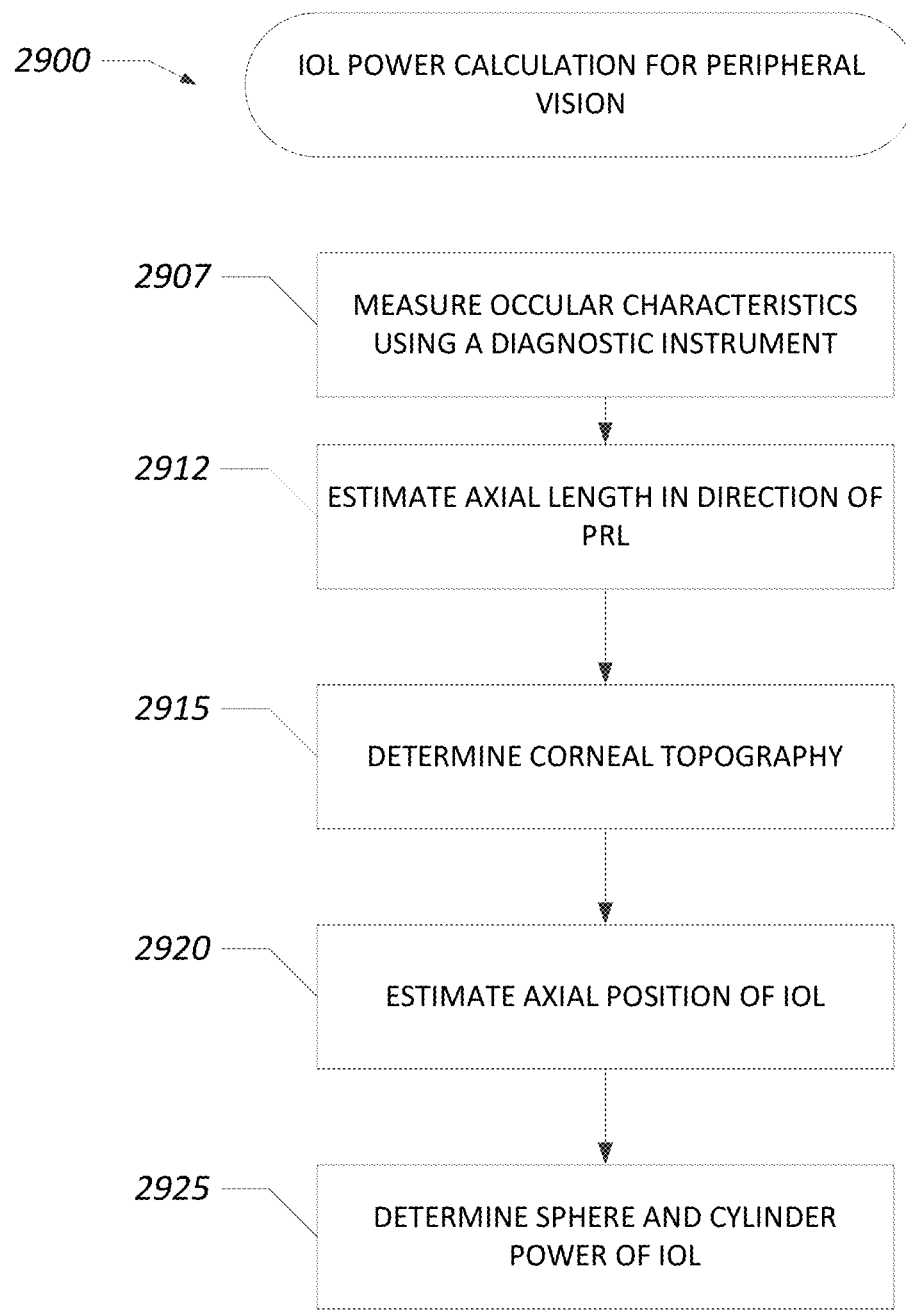

FIGS. 31A and 31B illustrate implementations of a method 2900 for determining an optical power of an IOL tailored to improve peripheral vision. For reference, FIG. 30 provides an illustration of an eye 2800 for which the method 2900 can be applied. In addition, FIG. 29 provides a block diagram of the IOL design system 27000 which can perform one or more operations of the method 2900. The method 2900 can be used to determine the optical power of the IOL which improves or optimizes optical quality at a PRL location. However, the method 2900 can be used to determine the optical power of an IOL to be used in any suitable procedure, such as where there is a loss of central vision, where the PRL is outside the fovea, where the PRL is within the fovea, where there are multiple PRLs, where the PRL is at a relatively large or small eccentricity, or the like.

With reference to FIGS. 31A and 31B, in block 2905, the on-axis axial length is measured. The on-axis axial length can be measured, for example, from the anterior surface of the cornea to the retina. The length can be determined using any number of standard techniques for making measurements of the eye. In some embodiments, instead of measuring the on-axis axial length, it is estimated based on computer models of eyes, statistical data (e.g., average on-axis distance for eyes with similar characteristics), or a combination of these. In some embodiments, the on-axis axial length is determined using a combination of measurement techniques and estimation techniques.

With reference to FIG. 31A, in block 2910, the PRL-axis axial length is measured. The PRL-axis axial length can be taken as the length along a deflected optical axis to the PRL location at the retina. The length can be measured from the anterior surface of the cornea, from the point of deflection from the optical axis, or any other suitable location. In some embodiments, the PRL-axis axial length can be estimated based on a combination of the eccentricity of the PRL, the PRL location, the retinal shape, the on-axis axial length, the distance from a proposed IOL location to the PRL, or any combination of these. In some embodiments, instead of measuring the PRL-axis axial length, it is estimated based on computer models of eyes, statistical data (e.g., average PRL-axis axial length for eyes with similar PRL locations and characteristics), or a combination of these. In some embodiments, the PRL-axis axial length is determined using a combination of measurement techniques and estimation techniques. In some embodiments, the PRL-axis axial length can be estimated based on population averages of ocular characteristics measured using a diagnostic instrument, as shown in block 2907 and 2912 of FIG. 31B. The measured ocular characteristics can include on-axis axial length, preoperative refraction power, corneal power or other measured parameters.

In block 2915, the corneal shape is determined. The anterior and/or posterior surfaces of the cornea can be determined using measurements, estimations, simulations, or any combination of these. The corneal power can be derived or determined based at least in part on the corneal shape, that can be measured with tomography or topographic techniques. In some embodiments, the corneal power is determined based on measurements of optical properties of the cornea.

In block 2920, the position of the IOL is estimated. The position of the IOL can be estimated based at least in part on an estimation of a location which would provide good optical quality at the fovea. The location can be one that takes into account the corneal power or topography and the on-axis axial length. Some other inputs that can be taken into consideration to predict the postoperative IOL position are the axial position of the crystalline lens from the anterior cornea, which is defined as anterior chamber depth, crystalline lens thickness, vitreous length on axis combinations of thereof. In some embodiments, the estimated position of the IOL can be refined by taking into account the PRL-axis axial length and/or eccentricity of the PRL. In some embodiments, the estimated IOL location can take into account data from previous procedures, with or without including the same IOL design. For example, historic data from cataract surgeries can be used as that data may indicate a good estimate of the IOL position.

In some embodiments, rather than determining an estimated initial position of the IOL configured to provide good optical quality for central/foveal vision, the estimated position can be configured to provide good optical quality for peripheral vision. Similar procedures as described for determining the IOL position that provides with good optical quality on axis can be applied in this case. Therefore, the location of the IOL can be predicted from biometric measurements, including corneal shape or power, axial length, either on axis or to the PRL, anterior chamber depth, crystalline lens thickens and/or vitreous length, either defined on axis or to the PRL. Retrospective data from previous cataract procedures aimed to restore vision on axis or at the PRL can also been taken into consideration to optimize the prediction of the IOL position that provide with good optical quality at the PRL. In addition to that, the estimated position can be based at least in part on procedures, for example, where the patient was suffering from central vision loss (e.g., due to AMD). Similarly, data can be used where the positions of IOLs have been tabulated and recorded as a function of the properties of the IOLs (e.g., sphere power, cylinder power, cylinder axis, redirection angle, etc.) and such properties were tailored using the systems and methods described herein. Data from such procedures can be subjected to further selection criteria based on the location of the PRLs of the patients, where the locations were, for example and without limitation, outside a determined angular range of the fovea, at an eccentric angle greater and/or less than a threshold eccentricity, at an eccentricity within a provided range of the PRL of the patient, or any combination of these. The data can be selected based on these criteria or other similar criteria which may improve the estimated IOL position for patients suffering from a loss of central vision.

In block 2925, the sphere and cylinder power of the IOL is determined using an IOL power calculation. The IOL power calculation can be configured to provide a spherical power for the IOL, a cylinder power for the IOL, and/or the cylinder axis, wherein the combination of one or more of these parameters is configured to provide good or optimal optical quality at the PRL location when the IOL is implanted at the estimated location.

The IOL power calculation can use as input data, for example and without limitation, on-axis axial length (e.g., the measurement or value provided in block 2905), corneal power (e.g., the value determined from measurements acquired in block 2915), fixation angle(s) (e.g., horizontal and vertical angles of fixation), intended post-operative refraction, eccentricity of the PRL, eccentric axial length (e.g., from the anterior cornea to the location of the PRL on the retina, such as the measurement or value provided in block 2910), predicted future movement of the PRL (e.g., due to progression of a disease such as AMD), a partial or full map of the retinal shape, a partial or full map of the retinal health, corneal topography, or the like. In some embodiments, the IOL power calculation is a regression formula, a theoretical formula (e.g., based on paraxial optical equations, ray tracing, etc.), or a combination of both of these. In some embodiments, current IOL power calculation procedures can be used while considering the eccentric axial length together with the corneal power. In those cases, A constants for either lenses to restore vision on axis after cataract surgery can be used. In certain embodiments, specific A constants can be determined depending on the design and/or eccentricity.

In some embodiments, ray tracing can be used to determine properties of the IOL which improve or reduce peripheral errors at the PRL based at least in part on the estimated IOL position. The ray tracing can incorporate relevant measurements and data including, for example and without limitation, the measurements of the eye (e.g., the measurements or values determined in blocks 2905, 2910, and 2915), the position of the PRL, the estimated position of the IOL (e.g., as provided in block 2920), and the like. This information can be used as input in a computer executable module or program stored in non-transitory computer memory, the module or program configured to cause a computer processor to execute instructions configured to perform ray tracing which can be accomplished, for example, by the IOL design system 27000 described herein with reference to FIG. 8. The ray tracing system can be used to find the sphere power, cylinder power, and/or cylinder axis of the IOL to be implanted in the eye 2800, wherein these parameters are tailored to improve or optimize for peripheral aberrations at the PRL location. Any standard ray tracing system or scheme can be used to accomplish the goal of tailoring the sphere power, cylinder power, and/or cylinder axis.

In some embodiments, the output of the IOL power calculation can be used for selecting an appropriate or suitable IOL where the output of the IOL power calculation includes, for example and without limitation, dioptric power, cylinder power, cylinder axis, deflection angle, and the like. These output values can be used in the selection of the IOL wherein the selected IOL has one or more properties within an acceptable range of the output values. In some embodiments, the IOL power calculation can be used to define or select IOL design parameters that improve or optimize optical quality as a function of retinal location(s) or retinal area(s).

In some embodiments, the IOL power calculation can be similar or equivalent to a power calculation configured to provide good or optimal on-axis optical quality (e.g., for central/foveal vision) where the axial length used is the PRL-axis axial length rather than the on-axis axial length. In some embodiments, the PRL-axis axial length can be determined based at least in part on the eccentricity of the PRL, the PRL location, the retinal shape, the length from the IOL to the PRL, or any combination of these. These and other input values can be determined based on measurements of a particular patient (e.g., the patient to receive the IOL), a group of patients, from computer models or simulations, or a combination of these sources. In an alternative embodiment, both, the axial length on axis and to the PRL can be considered, so that the IOL selected is that which maximizes the optical quality at the PRL and at, to some extended, at the fovea. In another embodiment, the axial length to several PRL can be considered, so that the IOL selected is that which has the characteristics that optimize the optical quality at each PRL.

In some embodiments, the IOL power calculation can be used for multifocal IOLs for patients suffering from a loss of central vision. The IOL power calculation can be configured to provide valid and acceptable results where the PRL lies within the fovea. In an alternative embodiment the add power of the multifocal IOL can be selected as that which maximizes the optical quality either at the PRL and/or the fovea.

In some embodiments, the IOL power calculation can be used in conjunction with the other systems and methods described herein configured to redirect and focus images to the PRL. The power calculations can be used to tailor the properties of the IOL, the IOL being used in combination with one or more redirection elements to reduce peripheral aberrations and/or improve peripheral image quality for patients suffering from a loss of central vision.

Additional Embodiments for Selecting IOL Sphere and Cylinder

As detailed above, IOL power is typically selected based primarily on axial length and corneal power, and any toric parts mostly depend on the toricity of the cornea. However, any spherical surface for which the light is obliquely incident will exhibit a large degree of astigmatism. The embodiments below detail additional ways to properly select sphere and cylinder of the IOL for the AMD patient.

In one embodiment, sphere selection is based on population data. Here, no new biometry readings are needed. Instead, the patients are classified depending on foveal refraction, from which the average peripheral spherical profile for that refractive group is selected. From the profile, spherical refraction at the PRL can be determined.

As seen above, sphere selection may also be based on individual data. The peripheral sphere can be determined through an axial length measurement to the PRL. This requires the modification of current axial length methods, since the oblique incidence on the crystalline lens will mean a longer than average passage through the lens, which has a higher index of refraction, increasing the difference between the optical path length and the physical length. The increased contribution can be predicted based on PRL location.

In one embodiment, astigmatism determination is based on population data. The inter-subject variation in astigmatism for a given angle is relatively modest. Therefore, the contribution of the oblique incidence at any given eccentricity can be predicted based on PRL location. For these calculations, PRL location should be determined based on the optical axis, which is on average between about 1-10 degrees horizontally and between about 1-5 degrees vertically from the fovea. The axis of the astigmatism can also be determined from the location, e.g. for a horizontal PRL the axis is 180 and for a vertical PRL the axis is 90, for a negative cylinder convention. Additionally, the astigmatism contribution of the IOL selected can be incorporated, in an iterative selection procedure. To this astigmatism, the corneal astigmatism from the cornea can also be added.

In another embodiment, astigmatism determination is based on individual data. Even for persons that are foveally emmetropic, the oblique astigmatism at e.g. 20 degrees can vary between 0.75 D and 2 D. There are several possible reasons for this: 1) The individual differences in angle between fovea and optical axis; 2) Individual differences in corneal power means the oblique astigmatism has different values; 3) Pupil position relative lens and cornea can be different leading to variation in the IOL position for different individuals. Biometry reading for any or all of these parameters can then be incorporated into an individual eye model, to select the best IOL cylinder power for the patient.

CONCLUSION

The above presents a description of systems and methods contemplated for carrying out the concepts disclosed herein, and of the manner and process of making and using it, in such full, clear, concise, and exact terms as to enable any person skilled in the art to which it pertains to make and use this invention. The systems and methods disclosed herein, however, are susceptible to modifications and alternate constructions from that discussed above which are within the scope of the present disclosure. Consequently, it is not the intention to limit this disclosure to the particular embodiments disclosed. On the contrary, the intention is to cover modifications and alternate constructions coming within the spirit and scope of the disclosure as generally expressed by the following claims, which particularly point out and distinctly claim the subject matter of embodiments disclosed herein.

Although embodiments have been described and pictured in an exemplary form with a certain degree of particularity, it should be understood that the present disclosure has been made by way of example, and that numerous changes in the details of construction and combination and arrangement of parts and steps may be made without departing from the spirit and scope of the disclosure as set forth in the claims hereinafter.

As used herein, the term "controller" or "processor" refers broadly to any suitable device, logical block, module, circuit, or combination of elements for executing instructions. For example, the controller 27050 can include any conventional general purpose single- or multi-chip microprocessor such as a Pentium® processor, a MIPS® processor, a Power PC® processor, AMD® processor, ARM processor, or an ALPHA® processor. In addition, the controller 27050 can include any conventional special purpose microprocessor such as a digital signal processor. The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. Controller 27050 can be implemented as a combination of computing devices, e.g., a combination of a DSP and a microprocessor, a plurality of microprocessors, one or more microprocessors in conjunction with a DSP core, or any other such configuration.

Computer readable memory 27100 can refer to electronic circuitry that allows information, typically computer or digital data, to be stored and retrieved. Computer readable memory 27100 can refer to external devices or systems, for example, disk drives or solid state drives. Computer readable memory 27100 can also refer to fast semiconductor storage (chips), for example, Random Access Memory (RAM) or various forms of Read Only Memory (ROM), which are directly connected to the communication bus or the controller 27050. Other types of memory include bubble memory and core memory. Computer readable memory 27100 can be physical hardware configured to store information in a non-transitory medium.

Methods and processes described herein may be embodied in, and partially or fully automated via, software code modules executed by one or more general and/or special purpose computers. The word "module" can refer to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may comprise connected logic units, such as gates and flip-flops, and/or may comprised programmable units, such as programmable gate arrays, application specific integrated circuits, and/or processors. The modules described herein can be implemented as software modules, but also may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with users, operators, other systems, components, programs, and so forth.

What is claimed is:

1. An intraocular lens configured to improve vision for a patient's eye, the intraocular lens comprising:
   an optic comprising a first surface and a second surface opposite the first surface, the first surface and the second surface intersected by an optical axis, the optic being symmetric about the optical axis, wherein the first and the second surface of the optic are aspheric,
   wherein the optic is configured to improve image quality of an image produced by light incident on the patient's eye at an oblique angle with respect to the optical axis and focused at a peripheral retinal location disposed at a distance from the fovea,
   wherein the image quality is improved by reducing oblique astigmatism at the peripheral retinal location, and
   wherein a shape factor of the intraocular lens is configured such that the intraocular lens has a modulation transfer function (MTF) of at least 0.3 for a spatial frequency of 30 cycles/mm for both the tangential and the sagittal foci at the peripheral retinal location.

2. The intraocular lens of claim 1, wherein the image quality is improved by reducing coma at the peripheral retinal location.

3. The intraocular lens of claim 1, wherein the oblique angle is between about 1 degree and about 25 degrees.

4. The intraocular lens of claim 1, wherein the modulation transfer function (MTF) of the intraocular lens is at least 0.2 for a spatial frequency of 100 cycles/mm for both the tangential and the sagittal foci at the fovea.

5. The intraocular lens of claim 1, wherein the optic is a meniscus lens with a vertex curving inwards from edges of the optic.

6. The intraocular lens of claim 1, wherein one of the first or second surface comprises one or more diffractive elements.

7. The intraocular lens of claim 1, wherein the optic element includes prismatic features.

8. The intraocular lens of claim 1, wherein the peripheral retinal location is disposed at a distance less than 3.0 mm from the fovea.

9. The intraocular lens of claim 1, wherein the peripheral retinal location is disposed at an eccentricity between about 1 degree and about 25 degrees.

10. The intraocular lens of claim 1, wherein the optic has a thickness less than 1.5 mm.

* * * * *